US010800812B2

(12) United States Patent
Lambris

(10) Patent No.: US 10,800,812 B2
(45) Date of Patent: Oct. 13, 2020

(54) COMPSTATIN ANALOGS WITH INCREASED SOLUBILITY AND IMPROVED PHARMACOKINETIC PROPERTIES

(71) Applicant: The Trustees of the University of Pennsylvania, Philadelphia, PA (US)

(72) Inventor: John D. Lambris, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/774,934

(22) Filed: Jan. 28, 2020

(65) Prior Publication Data

US 2020/0181199 A1    Jun. 11, 2020

Related U.S. Application Data

(63) Continuation of application No. PCT/US2019/026040, filed on Apr. 5, 2019.

(60) Provisional application No. 62/654,055, filed on Apr. 6, 2018.

(51) Int. Cl.
*C07K 7/08* (2006.01)
*A61K 47/60* (2017.01)
*A61K 9/00* (2006.01)
*C08G 65/48* (2006.01)
*A61K 38/00* (2006.01)

(52) U.S. Cl.
CPC .............. *C07K 7/08* (2013.01); *A61K 9/0019* (2013.01); *A61K 9/0048* (2013.01); *A61K 47/60* (2017.08); *C08G 65/48* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,299,838 A | 11/1981 | Durlach | |
| 4,576,750 A | 3/1986 | Pitzenberger | |
| 4,870,097 A | 9/1989 | Makovec et al. | |
| 4,969,912 A | 11/1990 | Kelman et al. | |
| 5,167,960 A | 12/1992 | Ito et al. | |
| 5,201,764 A | 4/1993 | Kelman et al. | |
| 5,256,642 A | 10/1993 | Fearon et al. | |
| 5,322,802 A | 6/1994 | Baliga et al. | |
| 5,492,135 A | 2/1996 | Devore et al. | |
| 5,593,854 A | 1/1997 | Berndt | |
| 5,632,984 A | 5/1997 | Wong et al. | |
| 5,667,839 A | 9/1997 | Berg | |
| 5,770,589 A | 6/1998 | Billson et al. | |
| 5,775,970 A | 7/1998 | Shechter et al. | |
| 5,861,486 A | 1/1999 | Devore et al. | |
| 6,129,761 A | 10/2000 | Hubbell | |
| 6,169,057 B1 | 1/2001 | Lovatt | |
| 6,197,934 B1 | 3/2001 | Devore et al. | |
| 6,204,365 B1 | 3/2001 | Devore et al. | |
| 6,214,790 B1 | 4/2001 | Richelson et al. | |
| 6,319,897 B1 | 11/2001 | Lambris et al. | |
| 6,378,526 B1 | 4/2002 | Bowman et al. | |
| 6,436,427 B1 | 8/2002 | Hammang et al. | |
| 6,692,759 B1 | 2/2004 | Wong et al. | |
| 6,800,481 B1 | 10/2004 | Holmes et al. | |
| 7,888,323 B2 * | 2/2011 | Lambris | A61P 43/00 514/20.6 |
| 7,989,589 B2 * | 8/2011 | Lambris | A61P 37/06 530/327 |
| 8,946,145 B2 * | 2/2015 | Lambris | A61P 11/08 514/2.9 |
| 9,169,307 B2 * | 10/2015 | Lambris | A61P 37/06 |
| 9,371,365 B2 * | 6/2016 | Lambris | A61P 37/08 |
| 9,579,360 B2 | 2/2017 | Lambris et al. | |
| 9,630,992 B2 * | 4/2017 | Lambris | A61P 11/02 |
| 10,174,079 B2 * | 1/2019 | Lambris | A61P 27/02 |
| 2001/0023066 A1 | 9/2001 | Kinders et al. | |
| 2007/0238654 A1 * | 10/2007 | Deschatelets | G01N 33/6872 514/13.3 |
| 2009/0220572 A1 | 9/2009 | Deschatelets et al. | |
| 2010/0041872 A1 * | 2/2010 | DeFrees | C12N 9/6437 530/381 |
| 2013/0344082 A1 | 12/2013 | Lambris | |
| 2014/0323407 A1 * | 10/2014 | Francois | A61K 38/00 514/15.2 |
| 2014/0371133 A1 | 12/2014 | Francois | |
| 2015/0110766 A1 | 4/2015 | Lambris | |
| 2016/0060297 A1 | 3/2016 | Deschatelets et al. | |
| 2016/0067357 A1 | 3/2016 | Francois | |

FOREIGN PATENT DOCUMENTS

| | | | |
|---|---|---|---|
| EP | 18158834.4 | † | 2/2018 |
| WO | WO 93/17669 A1 | | 9/1993 |

(Continued)

OTHER PUBLICATIONS

Cytochrome P450 [*Amycolatopsis methanolica*] NCBI Reference Sequence: WP_038531862.1 (Year: 2014).*
Protein Jingubang-like [*Tanacetum cinerariifolium*] GenBank: GEX34302.1; (Year: 2019).*
Maekawa et al. "Genetic and Intervention Studies Implicating Complement C3 as a Major Target for the Treatment of Periodontitis", The Journal of Immunology, 2014, pp. 6020-6027 (Year: 2014).*

(Continued)

*Primary Examiner* — Lianko G Garyu
(74) *Attorney, Agent, or Firm* — Potter Anderson and Corroon LLP

(57) ABSTRACT

Compounds comprising peptides capable of binding C3 protein and inhibiting complement activation are disclosed. The compounds comprise compstatin analogs in which the N-terminus and/or C-terminus contains an added component that improves (1) the peptide's solubility at physiological pH; (2) the peptide's plasma half-life; (3) the peptide's intraocular retention; and/or (4) the peptide's binding affinity to C3 or its fragments as compared to an unmodified compstatin peptide under equivalent conditions. Pharmaceutical compositions and methods of using the compounds are also disclosed.

15 Claims, 18 Drawing Sheets

Specification includes a Sequence Listing.

(56) References Cited

FOREIGN PATENT DOCUMENTS

| | | |
|---|---|---|
| WO | WO 99/13899 A1 | 3/1999 |
| WO | WO 00/47130 A1 | 8/2000 |
| WO | WO 2004/026328 A1 | 4/2004 |
| WO | WO 2007/062249 A2 | 5/2007 |
| WO | WO 2008/153963 A1 | 12/2008 |
| WO | WO 2010/127336 A1 | 11/2010 |
| WO | WO 2010/135717 A2 | 11/2010 |
| WO | WO 2012/040259 A2 | 3/2012 |
| WO | WO 2012/155107 A1 | 11/2012 |
| WO | WO 2013/036778 A2 | 3/2013 |
| WO | WO 2014/078731 A2 | 5/2014 |
| WO | WO 2014/078734 A2 | 5/2014 |
| WO | WO 2014/152391 A1 | 9/2014 |
| WO | WO 2017/062879 A2 | 4/2017 |
| WO | WO2019/166411 A1 † | 9/2019 |

OTHER PUBLICATIONS

Kato et al., Mutational Analysis of Protein Solubility Enhancement Using Short Peptide Tags, Published online Aug. 31, 2006 in Wiley InterScience, pp. 12-18 (Year: 2006).*
Bellows et al., "New Compstatin Variants Through Two De Novo Protein Design Frameworks" Biophysical J. 98:2337-2346 (2010).
Berger et al., "New Analogs of the Complement C3 Inhibitor Compstatin with Increased Solubility and Improved Pharmacokinetic Profile" J Med Chem 61(14):6153-6162 (2018).
Bourges et al., "Ocular Drug Delivery Targeting the Retina and Retinal Pigment Epithelium Using Polylactide Nanoparticles" Invest. Ophthalmol. Vis. Sci. 44(8):3562-3569 (2003).
Chiu et al., "Development of a New Pharmacophore Model that Discriminates Active Compstatin Analogs" Chem. Biol. Drug Des. 72:249-256 (2008).
Dennis et al., "Albumin binding as a general strategy for improving the pharmacokinetics of proteins" J. Biol. Chem., 277:35035-35043 (2002).
Einmahl et al., "Evaluation of a Novel Biomaterial in the Suprachoroidal Space of the Rabbit Eye" Invest. Ophthalmol. Vis. Sci. 43(5):1533-1539 (2002).
Gupta et al., "Oral delivery of therapeutic proteins and peptides: a review on recent developments" Drug Deliv. 20(6):237-246 (2013).
Holers, "The Spectrum of Complement Alternative Pathway-Mediated Diseases" Immunol. Rev. 223:300-316 (2008).
Huang et al., "Conjugation to Albumin—Binding Molecule Tags as a Strategy to Improve Both Efficacy and Pharmacokinetic Properties of the Complement Inhibitor Compstatin" ChemMedChem 9:2223-2226 (2014).
Jaffe, "Safety and pharmacokinetics of an intraocular fluocinolone acetonide sustained delivery device" Invest. Ophthalmol. Vis. Sci. 41 (11):3569-3575 (2000).
Katragadda & Lambris, "Expression of compstatain in *Escherichia coli*: Incorporation of unnatural amino acids enhances its activity" Protein Expression and Purification 47: 289-295 (2006).
Kozlowski et al., "Development of Pegylated Interferons for the Treatment of Chronic Hepatitis C" BioDrugs 15(7):419-29 (2001).
Lopez de Victoria et al., "A New Generation of Potent Complement Inhibitors of the Compstatin Family" Chem. Biol. Drug Design 77:431-440 (2011).
Loyet et al., "Activation of the alternative complement pathway in vitreous is controlled by genetics in age-related macular degeneration" Invest Ophthalmol Vis Sci. 53:6628-37 (2012).
Magotti et al., "Structure-kinetic relationship analysis of the therapeutic complement inhibitor compstatin" J Mol Recognit 22:495-505 (2009).

Maher et al., "Intestinal permeation enhancers for oral peptide delivery" Adv. Drug Deliv. Rev. 106:277-319 (2016).
Mallik et al., "Design and NMR Characterization of Active Analogues of Compstatin Containing Non-Natural Amino Acids" Journal of Medicinal Chemistry 48:274-286 (2005).
Matsuda et al., "Photoinduced Prevention of Tissue Adhesion" ASAIO J., 38:154-157 (1992).
Primikyri et al., "Method development and validation for the quantitation of the complement inhibitor Cp40 in human and cynomolgus monkey plasma by UPLC-ESI-MS2017" J Chromatogr B Analyt Technol Biomed Life Sci 1041-1042:19-26 (2017).
Risitano et al., "Peptide inhibitors of C3 activation as a novel strategy of complement inhibition for the treatment of paroxysmal nocturnal hemoglobinuria" Blood 123:2019-2101 (2014).
Robinson et al., "The design, structures and therapeutic potential of protein epitope mimetics" Drug Disc. Today 13: 944-951 (2008).
Qu et al., "Development of Compstatin Derivative-Albumin Binding Peptide Chimeras for Prolonged Plasma Half Life" Breaking Away: Proceedings of the 21st American Peptide Symposium, pp. 219-220 (2009).
Qu et al., "Novel analogues of the therapeutic complement inhibitor compstatin with significantly improved affinity and potency" Mol Immunol 48:481-489 (2011).
Qu et al., "New analogs of the clinical complement inhibitor compstatin with subnanomolar affinity and enhanced pharmacokinetic properties" Immunobiology 218:496-505 (2013).
Sahu et al., "Inhibition of Human Complement by a C3-Binding Peptide Isolated from a Phage-Displayed Random Peptide Library" The Journal of Immunology 157:884-891 (1996).
Steinleitner et al., "Poloxamer 407 as an intraperitoneal barrier material for the prevention of postsurgical adhesion formation and reformation in rodent models for reproductive surgery" Obstetrics & Gynecology 77:48-52 (1991).
Steinleitner et al., "An evaluation of Flowgel as an intraperitoneal barrier for prevention of postsurgical adhesion reformation" Fertility and Sterility, 57:305-308 (1992).
Vagner et al., "Peptidomimetics, a synthetic tool of drug discovery" Curr. Opin. Chem. Biol. 12: 292-296 (2008).
Veronese, "Peptide and protein PEGylation: a review of problems and solutions" Biomaterials 22:405-417 (2001).
Webster et al., "PEGylated Proteins: Evaluation of Their Safety in the Absence of Definitive Metabolism Studies" Drug Metab & Dispos 35: 9-16 (2007).
Zhang et al., "Effects of pharmaceutical PEGylation on drug metabolism and its clinical concerns" Expert Opin Drug Metab Toxicol 10:1691-1702 (2014).
Huang, "Evolution of compstatin family as therapeutic complement inhibitors" Expert Opin Drug Discovery 13(5):435-444 (2018).
International Search Report and Written Opinion in International PCT Application No. PCT/US2019/026040 dated Nov. 13, 2019.
Kato et al., "Mutational Analysis of Protein Solubility Enhancement Using Short Peptide Tags," Biopolymers, 2007, 85(1):12-18.†
Yang et al.,"CDR Walking Mutagenesis for the Affinity Maturation of a Potent Human Anti-HIV-1 Antibody into the Picomolar Range," J. Mol. Biol., 1995, 254:392-403.†
Huang et al., "Conjunction to Albumin-Binding Molecule Tags as a Strategy to Improve Both Efficacy and Pharmacokinetic Properties of the Complement Inhibitor Compstatin," ChemMedChem., 2014, 9(10):2223-2226.†
Rist et al., "From Micromolar to Nanomolar Affinity: A Systematic Approach to Identify the Binding Site of CGRP at the Human Calcitonin Gene-Related Peptide 1 Receptor," J. Med. Chem., 1998, 41:117-123.†

\* cited by examiner
† cited by third party

R₁-DTyr-Ile-[Cys-Val-mTrp-Gln-Asp-Trp-Sar-His-Arg-Cys]-mIle-NH-R₂ b)
| | R₁: | R₂: |
|---|---|---|
| Cp40: | -H | -H |
| mPEG(3k)-Cp40* | -COCH₂-PEG(3000)-OMe | -H |
| mPEG(2k)-Cp40* | -COCH₂-PEG(2000)-OMe | -H |
| mPEG(1k)-Cp40* | -COCH₂-PEG(1000)-OMe | -H |
| mPEG(1056)-Cp40# | -COCH₂-PEG(1056)-OMe | -H |
| mPEG(528)-Cp40# | -COCH₂-PEG(528)-OMe | -H |
| Cp40-K | -H | -Lys-NH₂ |
| Cp40-KK | -H | -Lys-Lys-NH₂ |
| Cp40-KKK | -H | -Lys-Lys-Lys-NH₂ | monodisperse polymer
*polydisperse polymer

COMPSTATIN ANALOGS WITH INCREASED SOLUBILITY AND IMPROVED PHARMACOKINETIC PROPERTIES

CROSS-REFERENCE TO RELATED APPLICATIONS

Continuation of PCT/US2019/026040, filed Apr. 5, 2019, which claims benefit of the filing date of U.S. Provisional Application No. 62/654,055, filed Apr. 6, 2018, the entire contents of each of which are incorporated by reference herein.

GOVERNMENT SUPPORT

This invention was made with government support under grant numbers AI030040 and AI068730 awarded by the National Institutes of Health. The government has certain rights in the invention.

FIELD OF THE INVENTION

This invention relates to activation of the complement cascade in the body. In particular, this invention provides compstatin analogs that bind the C3 protein with nanomolar affinity and exhibit robust complement inhibitory activity, increased solubility at physiological pH, plasma stability and in vivo retention.

BACKGROUND OF THE INVENTION

Various publications, including patents, published applications, technical articles and scholarly articles are cited throughout the specification. Each of these cited publications is incorporated by reference herein, in its entirety.

The human complement system is a powerful player in the defense against pathogenic organisms and the mediation of immune responses. Complement can be activated through three different pathways: the classical, lectin, and alternative pathways. The major activation event that is shared by all three pathways is the proteolytic cleavage of the central protein of the complement system, C3, into its activation products C3a and C3b by C3 convertases. Generation of these fragments leads to the opsonization of pathogenic cells by C3b and iC3b, a process that renders them susceptible to phagocytosis or clearance, and to the activation of immune cells through an interaction with complement receptors. Deposition of C3b on target cells also induces the formation of new convertase complexes and thereby initiates a self-amplification loop.

An ensemble of plasma and cell surface-bound proteins carefully regulates complement activation to prevent host cells from self-attack by the complement cascade. However, excessive activation or inappropriate regulation of complement can lead to a number of pathologic conditions, ranging from autoimmune to inflammatory diseases. The development of therapeutic complement inhibitors is therefore highly desirable. In this context, C3 and C3b have emerged as promising targets because their central role in the cascade allows for the simultaneous inhibition of the initiation, amplification, and downstream activation of complement.

As the number of clinical conditions linked to aberrant activation of the complement system continues to grow, so must the field of complement therapeutics in order to meet the increasing demand for effective and disease-tailored treatments. Despite tremendous ongoing efforts in research and drug development in this field, the first complement-targeting drug, eculizumab (Soliris®, Alexion), remains the only therapeutic on the market more than a decade after its FDA approval for the treatment of paroxysmal nocturnal hemoglobinuria (PNH). Eculizumab is a humanized monoclonal antibody against C5 that prevents its cleavage into C5a and C5b, thus blocking activation of the terminal pathway of complement. Thus, there remains a need to identify additional complement-targeting compounds as potential therapeutics.

Upstream intervention at the level of C3, the central component of the complement cascade, has been explored as an intervention approach, given the involvement of C3 in a variety of pathogenic pathways. The compstatin family, a group of cyclic peptides consisting of about 13 amino acids, was initially introduced two decades ago and shows strong binding affinity toward C3 from humans and non-human primates (NHPs) (Sahu et al., 1996, *The Journal of Immunology* 157:884-891). Continuous research and further development of compstatin has resulted in a number of next-generation analogs with improved complement inhibitory activity and target affinity, including the most potent derivative, Cp40 (see Qu et al., 2011, *Mol Immunol* 48:481-489; Qu et al., 2013, *Immunobiology* 218:496-505). As described by Qu et al. (2013, supra), Cp40 has a subnanomolar binding affinity for C3, almost 6,000-fold higher than that of the parent peptide, and an extended plasma half-life. However, despite its high solubility in water, Cp40 shows less solubility at physiological pH, thus limiting the routes of administration that can be used to deliver effective amounts of Cp40 as well as potentially causing increased precipitation at the injection site resulting in local irritation or pain to the patient. Further, a compstatin analog with high solubility at physiological pH would improve its suitability for both intravenous and subcutaneous administration, the latter providing various benefits over intravenous injection, such as lowering the cost for health care systems, reducing the frequency of administration, increasing the convenience and compliance for patients, and providing more options for self-administration.

Peptide modifications have been used to enhance solubility and extend the half-life of compounds in vivo. However, such modifications can decrease compound activity and/or binding, which would reduce the compound's beneficial characteristics. PEGylation has been used to potentiate drugs with undesirable properties, and these PEGylated compounds tend to display enhanced solubility. However, the improved solubility conferred by PEGylation may come at a cost as preserving the pharmacological activity of these modified compounds remains a challenge in some cases, thereby limiting the therapeutic benefit of certain compounds (for example, see Zhang et al., 2014, *Expert Opin Drug Megab Toxicol* 10:1691-1702). Indeed while PEGylation has been successfully applied to extend the plasma half-life and solubility of Cp40, it has been reported that a Cp40 coupled to an mPEG(40k) exhibited more than a 100-fold decrease in binding affinity for C3 fragments and a drop in inhibitory activity (Risitano et al., 2014, Blood 123:2019-2101). Further, with respect to in vivo drug clearance, it has been reported that clearance of PEG from the body decreases proportionately to the size of the PEG (see, e.g., Webster et al., 2007, *Drug Megab & Dispos* 35: 9-16).

In view of the foregoing, it is clear that the development of modified compstatin peptides with greater activity, in vivo stability, plasma residence time, solubility and/or bioavailability would constitute a significant advance in the art.

SUMMARY OF THE INVENTION

The present invention provides analogs of the complement-inhibiting peptide, compstatin. In particular, a compstatin analog is provided with a C-terminal and/or N-terminal modification that improves the solubility of the peptide without causing significant reduction in its pharmacokinetic properties and, in some cases, unexpectedly conferring enhanced plasma and vitreous stability and/or binding affinity for C3 and its fragments.

One aspect of the invention features a compound comprising a compstatin or compstatin analog having an amino acid sequence represented by SEQ ID NO:1, SEQ ID NO:2, SEQ ID NO:3, SEQ ID NO:4, SEQ ID NO: 5, SEQ ID NO: 6, or SEQ ID NO:7; and a terminal modification comprising an added terminal component that improves (1) the peptide's C3, iC3b, C3b or C3c binding affinity, (2) the peptide's solubility at physiological pH, (3) the peptide's plasma stability and/or plasma residence time, and/or (4) the peptide's vitreous stability and/or vitreous residence time, as compared with an unmodified compstatin peptide under equivalent conditions.

The terminal modification can be a C-terminal component or an N-terminal component. In some embodiments, the added terminal component comprises one or more, two or more, or three or more hydrophilic/charged amino acid residues, such as lysine, arginine, ornithine, or any combination thereof. In a particular embodiment, the one or more hydrophilic/charged amino acid residues are lysines.

In some embodiments, the compound comprises a compstatin analog having an amino acid sequence represented by SEQ ID NO:7 (Cp40). In others, the compound has an amino acid sequence represented by SEQ ID NO:8, SEQ ID NO: 9, or SEQ ID NO: 10; preferably, the amino acid sequence is represented by SEQ ID NO: 9 (Cp40-KK) or SEQ ID NO: 10 (Cp40-KKK).

The compound can include, additionally or alternatively, a polymer component. Such a component is useful to increase the bioavailability or extend the in vivo retention of the compound. In particular, the additional component is a short polymer, typically a polyethylene glycol (PEG) having an average molecular weight of about 3 kDa or less. The PEG is bound to either the N- or C-terminus of the compstatin analog. In one embodiment, the PEG is covalently bonded to the N-terminus via an amide linkage. In the foregoing embodiments, the PEG can be either a monodisperse PEG having a molecular weight of about 0.5 kDa to about 3 kDa or a polydisperse PEG having an average molecular weight of about 0.5 kDa to about 3 kDa.

In another aspect, the compstatin peptide has the amino acid sequence Xaa1-Xaa2-Cys-Val-Xaa3-Gln-Xaa4-Xaa5-Gly-Xaa6-His-Xaa7-Cys-Xaa8 (SEQ ID NO:7), in which the Gly between Xaa5 and Xaa6 optionally is modified to constrain the backbone conformation; wherein:

Xaa1 is absent or is Tyr, D-Tyr or Sar;
Xaa2 is Ile, Gly or Ac-Trp;
Xaa3 is Trp or an analog of Trp, wherein the analog of Trp has increased hydrophobic character as compared with Trp;
Xaa4 is Asp or Asn;
Xaa5 is Trp or an analog of Trp comprising a chemical modification to its indole ring wherein the chemical modification increases the hydrogen bond potential of the indole ring;
Xaa6 is His, Ala, Phe or Trp;
Xaa7 is Arg or Orn; and
Xaa8 is Thr, Ile, Leu, Nle, N-methyl Thr or N-methyl Ile, wherein a carboxy terminal —OH of any of the Thr, Ile, Leu, Nle, N-methyl Thr or N-methyl Ile optionally is replaced by —NH$_2$; and
the peptide is cyclic via a Cys-Cys or thioether bond.

In such aspect, the compstatin peptide includes a terminal modification comprising an added terminal component that improves (1) the peptide's C3, iC3b, C3b or C3c binding affinity, (2) the peptide's solubility at physiological pH, and/or (3) the peptide's plasma stability and/or plasma residence time; and/or (4) the peptide's vitreous stability and/or vitreous residence time, as compared with an unmodified compstatin peptide under equivalent conditions.

In another aspect of the invention, a pharmaceutical composition is described that comprises any one of the foregoing compounds combined with a pharmaceutically acceptable carrier. The pharmaceutical composition can be formulated for a variety of administration routes, including, oral, topical, intraocular (including intravitreal or via an ocular implant), periodontal (including gingival or via intrapapillary infiltration), pulmonary, subcutaneous, intramuscular, or intravenous. In some embodiments, a method of inhibiting complement activation is described that includes the administration of any one of the foregoing pharmaceutical compositions.

In some embodiments, the compound is a compstatin or compstatin analog linked to a polymer having an average molecular weight of about 3 kDa or less. In a particular example, the polymer is polyethylene glycol (PEG) with an average molecular weight of about 3 kDa or less. In some aspects, the PEG is linked to the N- or C-terminus. The PEG may be monodisperse or polydisperse and may have an average molecular weight of between about 0.5 kDa and 3 kDa.

In another aspect, novel Cp40 analogs are described that comprise, consist of, or consist essentially of the amino acid sequences represented by SEQ ID NO:9 or SEQ ID NO:10. In some aspects, the novel Cp40 analogs include Cp40-KK, Cp40-KKK, mPEG(1K)-Cp40, and mPEG(3K)-Cp40.

Also described herein are methods of treating an individual having a pathological condition associated with complement activation that include the steps of providing an individual having a pathological condition associated with complement activation; administering to the individual a therapeutically effective amount of any one of the pharmaceutical compositions described herein; and measuring one or more parameters of the pathological condition. In these methods, administering of the pharmaceutical composition results in inhibition of complement. The pathological condition that can be treated by these methods includes, but is not limited to, atypical hemolytic uremic syndrome (aHUS); dense deposit disease (DDD); C3 glomerulonephritis (C3GN); C3 glomerulopathies; other complement-mediated nephropathies and glomerular inflammatory diseases; age-related macular degeneration (AMD); any eye disorder characterized by macular degeneration, choroidal neovascularization (CNV); retinal Neovascularization (RNV), proliferative vitreoretinopathy, glaucoma, uveitis, ocular inflammation, or any combination of these; paroxysmal nocturnal hemoglobinuria (PNH); cold agglutinin disease (CAD); warm antibody autoimmune hemolytic anemias (wAIHAs); sickle cell disease; transplant-associated thrombotic microangiopathies; rheumatoid arthritis (RA), systemic lupus erythematosus (SLE); several autoimmune and auto-inflammatory kidney diseases; autoimmune myocarditis; multiple sclerosis; traumatic brain and spinal cord injury; cerebral, intestinal and renal ischemia-reperfusion (IR) injury; spontaneous and recurrent pregnancy loss; antiphospholipid syndrome (APS); Parkinson's disease; Alzheimer's disease; other neurodegenerative inflammatory conditions underpinned by aberrant synaptic remodeling, excessive microglial activity and cognitive decline; asthma; anti-nuclear cytoplasmic antigen-associated pauci-immune vasculitis (Wegener's syndrome); non-lupus autoimmune skin diseases such as pemphigus, bullous pemphigoid, and epidermolysis bullosa; post-traumatic shock, cancer; periodontitis; gingivitis; and atherosclerosis.

In some embodiments, the method employs a pharmaceutical composition that is administered intravenously or subcutaneously at a therapeutically effective dose of between about 0.125 mg/kg and about 10 mg/kg, or between about 0.25 mg/kg and about 5 mg/kg, or between about 0.5 mg/kg and about 5 mg/kg, or between about 0.5 mg/kg and about 4 mg/kg, or about 3 mg/kg. In other embodiments, the pharmaceutical composition is administered intramuscularly at a therapeutically effective dose of between about 0.25 mg/kg and about 50 mg/kg, or between about 0.25 mg/kg and about 35 mg/kg, or between about 0.25 mg/kg and about 10 mg/kg, or between about 0.25 mg/kg and about 5 mg/kg, or about 2.5 mg/kg. In other embodiments, the pharmaceutical composition is administered orally at a therapeutically effective dose of between about 1 mg/kg and about 20 mg/kg, or between about 1 mg/kg and about 10 mg/kg, or between about 1 mg/kg and about 5 mg/kg. In yet other embodiments, the pharmaceutical composition is administered intravitreally at a therapeutically effective dose of between about 1 g and about 10 mg, or between about 1 g and about 2,000 g, or about 1 mg. In still others, the pharmaceutical composition is administered periodontally at a therapeutically effective dose of between about 1 g and about 1,000 g, or between about 10 g and about 200 g, or between about 20 g and about 100 g, or about 25 g or 50 g. In some aspects, the periodontal administration is by intragingival injection or intrapapillary infiltration. These pharmaceutical compositions may be administered as a single dose or at regular intervals ranging from once every 12 hours to once every 3 months (e.g., once every 2-3 days, once every 2 weeks, or once every 3 months).

Other aspects of the method envision a pharmaceutical composition administered intravenously or subcutaneously to the individual as a first therapeutically effective dose that is between about 0.125 mg/kg and about 10 mg/kg (or between about 0.5 mg/kg to about 3 mg/kg) and followed by further administration of the pharmaceutical composition in a second therapeutically effective maintenance dose of between about 0.25 mg/kg and about 50 mg/kg if administered intramuscularly or between about 1 mg/kg and about 20 mg/kg if administered orally. Moreover, the second therapeutically effective maintenance dose may be between about 0.25 mg/kg and about 10 mg/kg or between about 0.25 mg/kg and about 5 mg/kg when administered intramuscularly. Alternatively, the second therapeutically effective dose may be administered orally at a range of between about 1 mg/kg and about 10 mg/kg or about 1 mg/kg and about 5 mg/kg.

In another aspect of the invention, a method of inhibiting complement activation in an individual is provided that includes the steps of providing an individual; administering to the individual a therapeutically effective amount of a pharmaceutical composition comprising a pharmaceutically acceptable carrier and any one of the foregoing compounds; and measuring one or more parameters of complement activation in the individual. The pharmaceutical compositions employed in this method can include any of the formulations and dosage amounts described above, and can be administered as a single dose or at regular intervals ranging from once every 12 hours to once every 3 months (e.g., every 2-3 days, every 2 weeks, or every 3 months). The pharmaceutical composition can be administered as a first therapeutically effective dose (e.g., intravenously or subcutaneously) and then as a second therapeutically effective maintenance dose (e.g., intramuscularly or orally). The therapeutically effective doses that may be used with this method include, but are not limited to: intravenous or subcutaneous in the ranges of between about 0.125 and about 10 mg/kg, about 0.25 mg/kg and about 5 mg/kg, about 0.5 mg/kg and about 5 mg/kg, about 0.5 mg/kg and about 4 mg/kg, or about 0.5 mg/kg and about 3 mg/kg; intramuscularly in the ranges of between about 0.25 mg/kg and about 50 mg/kg, about 0.25 mg/kg and about 35 mg/kg, about 0.25 mg/kg and about 30 mg/kg, about 0.25 mg/kg and about 10 mg/kg, about 0.25 mg/kg and about 5 mg/kg; or orally in the ranges of between about 1 mg/kg and about 20 mg/kg, about 1 mg/kg and about 10 mg/kg, or about 1 mg/kg and about 5 mg/kg. In such embodiments, the second therapeutically effective maintenance dose is administered to the individual every 2-3 days or every 2 weeks. In some embodiments, the pharmaceutical composition is administered via ocular implants at a therapeutically effective dose of between about 100 g and about 50 mg (e.g., between about 100 g and about 10 mg, or between about 100 g and about 5 mg, or between about 100 g and about 500 g). The ocular implant may be maintained on or in the eye of the individual (e.g., a human) for a period of at least about 2 days. In other embodiments, the ocular implant may be maintained on or in the eye for a period of at least about 1 week. In yet others, the ocular implant is maintained on or in an eye for a period of at least about 1 month.

In another aspect, a method of detection of a compstatin analog in a biological sample is provided herein and includes the steps of (1) providing a biological sample that comprises a first plurality of compstatin analog molecules, wherein at least a portion of the compstatin analog molecules are bound to C3 and/or its fragments C3b, iC3b, and C3c to produce a plurality of C3-bound compstatin analog molecules; (2) heat-inactivating the biological sample to produce a heat-inactivated sample wherein compstatin molecules are dissociated from their target C3 molecules; (3) providing a CM5 sensor chip to which a second plurality of compstatin analog molecules are covalently attached; (4) mixing the heat-inactivated sample with a pre-determined amount of C3/C3b/iC3b/C3c or human plasma (as a source of C3) and contacting the mixture to the CM5 sensor chip whereby the heat-released compstatin analog molecules, present in the biological sample, compete with the immobilized compstatin analog molecules for binding to C3; and (5) detecting the binding of free C3/C3b/iC3b/C3c to compstatin analog molecules on the CM5 chip, whereby the reduction of bound C3/C3b/iC3b/C3c is proportional to the presence of compstatin analog molecules in the heat-inactivated biological sample.

In some embodiments, the method of detection utilizes surface plasmon resonance. In other embodiments, the biological sample is a vitreous sample or plasma sample extracted from a human or non-human primate. This method may be carried out using any of the analogs described above, such as Cp40-KK, Cp40-KKK, mPEG(1K)-Cp40, or mPEG (3K)-Cp40.

Also provided herein is a method of generating highly specific antibodies for the detection of Lysine-modified or unmodified compstatin analogs that includes the steps of: (a) immunizing a first mammal with a first compstatin or a compstatin analog; (b) immunizing a second mammal with a second compstatin or a compstatin analog, wherein the second compstatin or compstatin analog has the same amino acid sequence as the first compstatin or compstatin analog in (a) except with one or more lysine residues linked to the C-terminus; (c) injecting the first mammal with the first compstatin or compstatin analog, wherein the injecting is performed every at least two days for a period of at least 2 weeks, and wherein a first plurality of antibodies are generated; (d) injecting the second mammal with the second compstatin or compstatin analog, wherein the injecting is performed every at least two days for a period of at least 2 weeks, and wherein a second plurality of antibodies are generated; and (e) purifying the first plurality of antibodies and the second plurality of antibodies. The first and second antibodies produced by this method are capable of distinguishing an antigen of the first compstatin or compstatin analog from an antigen of the second compstatin or compstatin analog, respectively. In a preferred embodiment, the first and second antibodies produced by this method are monoclonal antibodies.

Other features and advantages of the present invention will be understood by reference to the detailed description, drawings, and examples that follow.

BRIEF DESCRIPTION OF THE DRAWINGS

FIG. 1, panel b) depicts a summary of various embodiments of the Cp40-based analogs described herein. FIG. 1, panel c) is an excerpt of the UV-HPLC-chromatograms of Cp40 and its analogs eluting between 13.9 and 18.7 min.

FIG. 7, panels c) and d) show the quantification of Cp40-KKK in the plasma samples of two cynomolgus monkeys, as determined by UPLC-ESI-MS. Also included are the fragments that were detected in the individual samples and the sum of the detected fragments corresponding to the total amount of peptide in each sample.

DETAILED DESCRIPTION OF THE ILLUSTRATIVE EMBODIMENTS

Definitions

Figure 1:
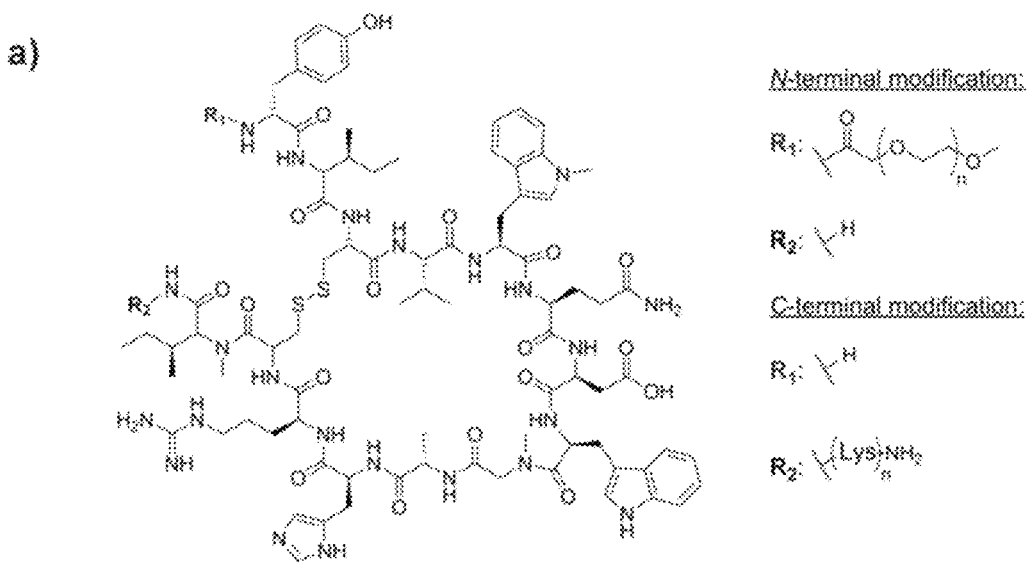
FIG. 1, panel a) depicts the general structure of Cp40 and the Cp40 N-terminal and C-terminal modifications.
Figure 1:
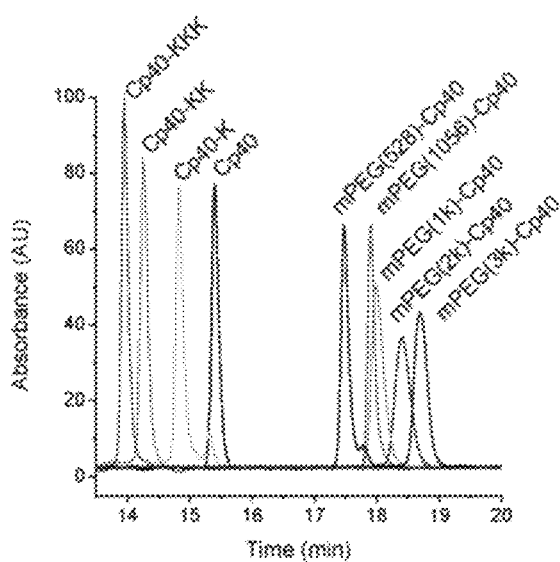

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The following abbreviations may be used herein: Ac, acetyl group; BSA, bovine serum albumin; DCM, dichloromethane; DMF, dimethylformamide; ELISA, enzyme-linked immunosorbent assay; ESI, electrospray ionization; Fmoc, 9-fluorenylmethoxycarbonyl; MALDI-TOF-MS, matrix-assisted laser desorption ionization-time-of-flight mass spectrometry; NHP, non-human primate; PBS, Phosphate Buffered Saline; RP-HPCL, reversed-phase high-performance liquid chromatography; Sar, N-methyl glycine; s.c., subcutaneous; SPR, surface plasmon resonance; TFA, trifluoroacetic acid; UPLC-ESI-MS, ultra-performance liquid chromatography-electrospray ionization-tandem mass spectrometry; VBS, Veronal buffered saline; WFI, water for injection.

The singular form of a word includes the plural, and vice versa, unless the context clearly dictates otherwise. The, the references "a", "an", and "the" are generally inclusive of the plurals of the respective terms. For example, references to "a compound" or "a method" includes a plurality of such "compounds" or "methods." Similarly, the words "comprise", "comprises", and "comprising" are to be interpreted inclusively rather than exclusively. Likewise, the terms "include", "including", and "or" should all be construed to be inclusive, unless such a construction is clearly prohibited from the context.

The terms "comprising" or "including" are intended to include embodiments encompassed by the terms "consisting essentially of" and "consisting of" Similarly, the term "consisting essentially of" is intended to include embodiments encompassed by the term "consisting of." Moreover, the term "consisting essentially of" limits the scope of an embodiment to the specified components or steps and those components or steps that do not materially affect the basic and novel characteristics of the embodiment.

The term "about" as used herein when referring to a measurable value such as an amount, a temporal duration, and the like, is meant to encompass variations of ±20% or ±10%, in some embodiments ±5%, in some embodiments ±1%, and in some embodiments ±0.1% from the specified value, as such variations are appropriate to make and use the disclosed compounds and compositions.

The term "compstatin" as used herein refers to a peptide comprising SEQ ID NO:1, I[CVVQDWGHHRC]T (cyclic C2-C12 by way of a disulfide bond indicated by the brackets). The term "compstatin analog" refers to a modified compstatin comprising substitutions of natural and/or unnatural amino acids, or amino acid analogs, as well as modifications within or between various amino acids, as described in greater detail herein, and as known in the art. When referring to the location of particular amino acids or analogs within compstatin or compstatin analogs, those locations are sometimes referred to as "positions" within the peptide, with the positions numbered from 1 (Ile in compstatin) to 13 (Thr in compstatin). For example, the Gly residue occupies "position 8."

The terms "pharmaceutically active" and "biologically active" refer to the ability of the compounds of the invention to bind C3 or fragments thereof and inhibit complement activation. This biological activity may be measured by one or more of several art-recognized assays, as described in greater detail herein.

As used herein, "alkyl" refers to an optionally substituted saturated straight, branched, or cyclic hydrocarbon having from about 1 to about 10 carbon atoms (and all combinations and subcombinations of ranges and specific numbers of carbon atoms therein), with from about 1 to about 7 carbon atoms being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl. The term "lower alkyl" refers to an optionally substituted saturated straight, branched, or cyclic hydrocarbon having from about 1 to about 5 carbon atoms (and all combinations and subcombinations of ranges and specific numbers of carbon atoms therein). Lower alkyl groups include, but are not limited to, methyl, ethyl, n-propyl, isopropyl, n-butyl, isobutyl, t-butyl, n-pentyl, cyclopentyl, isopentyl, and neopentyl.

As used herein, "halo" refers to F, Cl, Br, or I.

As used herein, "alkanoyl", which may be used interchangeably with "acyl", refers to an optionally substituted straight or branched aliphatic acylic residue having from about 1 to about 10 carbon atoms (and all combinations and subcombinations of ranges and specific numbers of carbon atoms therein), with from about 1 to about 7 carbon atoms being preferred. Alkanoyl groups include, but are not limited to, formyl, acetyl, propionyl, butyryl, isobutyryl, pentanoyl, isopentanoyl, 2-methyl-butyryl, 2,2-dimethylpropionyl, hexanoyl, heptanoyl, octanoyl, and the like. The term "lower alkanoyl" refers to an optionally substituted straight or branched aliphatic acylic residue having from about 1 to about 5 carbon atoms (and all combinations and subcombinations of ranges and specific numbers of carbon atoms therein. Lower alkanoyl groups include, but are not limited to, formyl, acetyl, n-propionyl, iso-propionyl, butyryl, isobutyryl, pentanoyl, iso-pentanoyl, and the like.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl as defined above, bearing an aryl substituent and having from about 6 to about 20 carbon atoms (and all combinations and subcombinations of ranges and specific numbers of carbon atoms therein), with from about 6 to about 12 carbon atoms being preferred. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy, among others.

As used herein, "carboxy" refers to a —C(=O)OH group.

As used herein, "alkoxycarbonyl" refers to a —C(=O)O-alkyl group, where alkyl is as previously defined.

As used herein, "aroyl" refers to a —C(=O)-aryl group, wherein aryl is as previously defined. Exemplary aroyl groups include benzoyl and naphthoyl.

Typically, substituted chemical moieties include one or more substituents that replace hydrogen at selected locations on a molecule. Exemplary substituents include, for example, halo, alkyl, cycloalkyl, aralkyl, aryl, sulfhydryl, hydroxyl (—OH), alkoxyl, cyano (—CN), carboxyl (—COOH), acyl (alkanoyl: —C(=O)R); —C(=O)O-alkyl, aminocarbonyl (—C(=O)NH$_2$), —N— substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term "D-amino acid" refers to dextrorotatory alpha-amino acids. Unless specified otherwise, all amino acids referred to herein are L-amino acids.

"Hydrophobic" or "nonpolar" are used synonymously herein, and refer to any inter- or intra-molecular interaction not characterized by a dipole.

"PEGylation" refers to the reaction in which at least one polyethylene glycol (PEG) moiety, regardless of size, is chemically attached to a protein or peptide to form a PEG-peptide conjugate. "PEGylated" means that at least one PEG moiety, regardless of size, is chemically attached to a peptide or protein. The term PEG is generally accompanied by a numeric suffix that indicates the approximate average molecular weight of the PEG polymers; for example, PEG-8,000 refers to polyethylene glycol having an average molecular weight of about 8,000 Daltons (or g/mol).

"Monodisperse" refers to a polymer composed of molecules having chain lengths of approximately the same mass.

"Polydisperse" refers to a polymer composed of molecules having chain lengths over a range of molecular masses, where the mass is typically indicated by the average molecular weight.

As used herein, "pharmaceutically acceptable salts" or "pharmaceutically acceptable esters" refer to derivatives of the disclosed compounds wherein the parent compound is modified by making an ester or an acid or base salt form, which is compatible with any other ingredients of the pharmaceutical composition, and which is not deleterious to the subject to which the composition is to be administered. Examples of pharmaceutically-acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds of the present invention may exist as zwitterions. All forms of the compounds, including free acid, free base, and zwitterions, are contemplated to be within the scope of the present invention.

As used herein, the phrase "pharmaceutically suitable fluids or "pharmaceutically suitable liquids," especially with reference to solubility of the compounds of the invention, but not limited thereto, refers collectively to fluids that include but are not limited to buffers and other aqueous solutions having a physiological pH, as well as non-aqueous solvents and liquid media commonly used for the preparation and delivery of drugs to the body by various routes as discussed herein. Such non-aqueous solvents and liquid media include: polar protic and/or aprotic non-aqueous organic solvents such as lower alcohols, methyl and vinyl pyrrolidones such as polyvinylpyrrolidone, methylsulfonyl methane, dimethylsulfoxide and related compounds, hydroxy and polyhydroxy acids such as polylactic acid, among others. This phrase may be used interchangeably with the term "clinically relevant solvents."

As used herein, the term "pharmaceutically-acceptable carrier" means a chemical composition with which a compstatin analog may be combined and which, following the combination, can be used to administer the compstatin analog to an individual.

As used herein, "intraocular administration" or "ocular administration" of a pharmaceutical composition includes any route of administration characterized by introduction into the eye, including "intravitreal administration." The term "intravitreal administration" of a pharmaceutical composition includes any route of administration characterized by introduction into the vitreous cavity of the eye. The "vitreous" is a gel-like substance within the vitreous cavity that fills the space between the lens and the retina and helps the eye maintain its shape.

As used herein, "intramuscular administration" of a pharmaceutical composition includes any route of administration characterized by introduction into the muscles.

As used herein, "periodontal administration" of a pharmaceutical composition refers to the administration within the tissues surrounding and/or around a tooth or teeth (e.g., by injection, topical application, or biodegradable implant), and includes "gingival administration" and "intrapapillary infiltration." As used herein, "gingival administration" of a pharmaceutical composition refers includes any route of administration characterized by introduction to or into the gingiva, or gums. "Intrapapillary infiltration" or "intrapapillary infiltration injection" is a type of gingival administration that refers to administration of a pharmaceutical composition into the interdental papilla, which is the gingiva (gum) tissue that exists coronal to the free gingival margin on the buccal and lingual surfaces of the teeth.

As used herein, "oral administration" or "enteral administration" of a pharmaceutical composition includes any route of administration characterized by introduction into the gastrointestinal tract. "Oral administration" includes feeding by mouth as well as orogastric or intragastric gavage. "Oral administration" or "enteral administration" also may include sublingual, buccal, intranasal, pulmonary or rectal administration, among other routes known in the art.

As will be appreciated by the skilled artisan, "physiological pH" typically refers to the pH of human blood, which is maintained between 7.35 and 7.45. As used herein, the term "physiological pH includes a pH range of 7.3 to 7.5.

The term "treating" refers to any indicia of success in the treatment or amelioration of the disease or condition. Treating can include, for example, reducing or alleviating the severity of one or more symptoms of the disease or condition, or it can include reducing the frequency with which symptoms of a disease, defect, disorder, or adverse condition, and the like, are experienced by an individual, such as a human patient.

The term "preventing" refers to the prevention of the disease or condition in an individual, such as a human patient. For example, if an individual at risk of developing an inflammatory disease is treated with the compounds and/or using the methods of the present invention and does not later develop the disease or condition, then the disease has been prevented in that individual.

The term "treat or prevent" is sometimes used herein to refer to a method that results in some level of treatment or amelioration of the disease or condition, and contemplates a range of results directed to that end, including but not restricted to prevention of the condition entirely.

The term "parameter" as used herein to refer to measuring any bodily function that is observable or measurable using suitable measuring techniques available in the art. As one having ordinary skill in the art will appreciate, measuring one or more "parameters" of bodily function can be used to detect a particular dysfunction as compared to the average normal parameters and can also be used to determine whether that bodily function has improved following or during treatment. Such parameters can be general, e.g., body temperature, blood pressure, pulse (heart rate), and breathing rate (respiratory rate), or they can be specific to a particular organ, tissue or disease or condition, e.g., functional test results from blood or other organs/tissues.

The terms "therapeutically effective amount" or "therapeutically effective dose" is the amount of a pharmaceutical composition sufficient to provide a beneficial effect to the individual to whom the pharmaceutical composition is administered.

Description:

The present invention arises in part from the inventors' development of compstatin analogs displaying increased solubility and improved pharmacokinetic parameters. Modification of the compstatin or compstatin analog with small polymers (e.g., about 3,000 Da or less) at the N-terminus results in compstatin analogs with improved solubility in clinically relevant solvents while, at the same time, having complement inhibitory activity similar to that of the unmodified parent compound under equivalent conditions. Polydisperse, and particularly monodisperse, polyethylene glycol (PEG) of average molecular weight ~500-3,000 Da are particularly suitable.

Additionally, modification of the compstatin or compstatin analog at the N-terminus or C-terminus with the addition of one or more charged hydrophilic amino acid residues, such as lysine, can confer improved pharmacokinetic properties (e.g., increased solubility) to the compstatin or compstatin analog. For instance, described herein are modifications of the compstatin or compstatin analog at the C-terminus with the addition of one or more charged hydrophilic residues (e.g., lysine), which not only increases the solubility of the peptide, but unexpectedly enhances the residence time and binding affinity of the compstatin analog for C3 or its fragments. Pharmacokinetic evaluation of the modified compstatin analog Cp40 in non-human primates revealed plasma half-life values for the modified Cp40 peptides similar to, or even exceeding, that of the unmodified Cp40-based analog. Thus, the present compstatin analogs exhibit improved pharmacokinetic profiles as well as improved solubility at physiological pH.

Thus, one modification in accordance with the present invention comprises adding a component to the C-terminus of compstatin (Ile-Cys-Val-Val-Gln-Asp-Trp-Gly-His-His-Arg-Cys-Thr (cyclic C2-C12) (SEQ ID NO:1), or any analog thereof as described in more detail below, that improves solubility of the peptide at physiological pH, while maintaining a similar C3 binding affinity, plasma half-life, and/or complement inhibitory activity as compared to the unmodified parent peptide under equivalent conditions. For instance, in some embodiments, 1, 2, 3, 4, 5, 6, 7, 8, 9, 10, or more hydrophilic and/or charged amino acids (e.g., Arg or Lys) are added to the C-terminus. In some embodiments, two or more hydrophilic and/or charged amino acid residues are added to the C-terminus of the compstatin analog. In other embodiments, three or more hydrophilic/charged amino acid residues are added to the C-terminus of the compstatin analog. In particular embodiments, the hydrophilic/charged amino acid residue is Lys, Arg or a combination thereof. In a more preferred embodiment, one or more lysine amino acid residues are added to the C-terminus of compstatin or a compstatin analog. For instance, in an exemplary embodiment described in more detail below, one or more lysine amino acid residues are added to the C-terminus of the compstatin analog Cp40.

Exemplary embodiments of the invention feature the compstatin analog Cp40, in which two or more lysine amino acid residues are added to the C-terminus. As described in greater detail below and in the examples, the inventors have discovered that Cp40-KK and Cp40-KKK not only exhibit increased solubility as compared to unmodified Cp40, but, surprisingly, exhibit increased plasma and vitreous retention and enhanced C3-binding as compared to Cp40 and other Cp40-based analogs. In fact, Cp40-KKK displays in vivo residence times equal to or exceeding three months following intravitreal administration. Notably, both Cp40-KK and Cp40-KKK analogs display markedly improved pharmacokinetic properties as compared to Cp40.

Another modification in accordance with the present invention comprises adding a component to either or both of the N- or C-termini of compstatin or analogs thereof that improves solubility of the peptide at physiological pH, while maintaining a similar C3 binding affinity, plasma half-life, and/or complement inhibitory activity as compared to the unmodified parent peptide under equivalent conditions. In particular embodiments, the added component is the addition of a short polymer, e.g., polyethylene glycol (PEG) with shorter chain length than PEGs that have been used previously. PEG used in accordance with the present invention have an average molecular weight of about 500 to about 5,000, e.g., 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,00, 4,100, 4,200, 4,300, 4,400, 4,500, 4,600, 4,700, 4,800, 4,900, or 5,000. In preferred embodiments, the PEGs have an average molecular weight of less than 5,000. In one embodiment, the compstatin analog is modified at one or both termini to include PEG having an average molecular weight of about 500 to about 5,000 Da. In another embodiment, the PEG has an average molecular weight of about 1,000 to about 3,000 Da. In an exemplary embodiment, the Cp40-based analog is modified to include an N-terminal PEG with an average molecular weight of about 1,000 to about 3,000 Da.

Figure 2A:
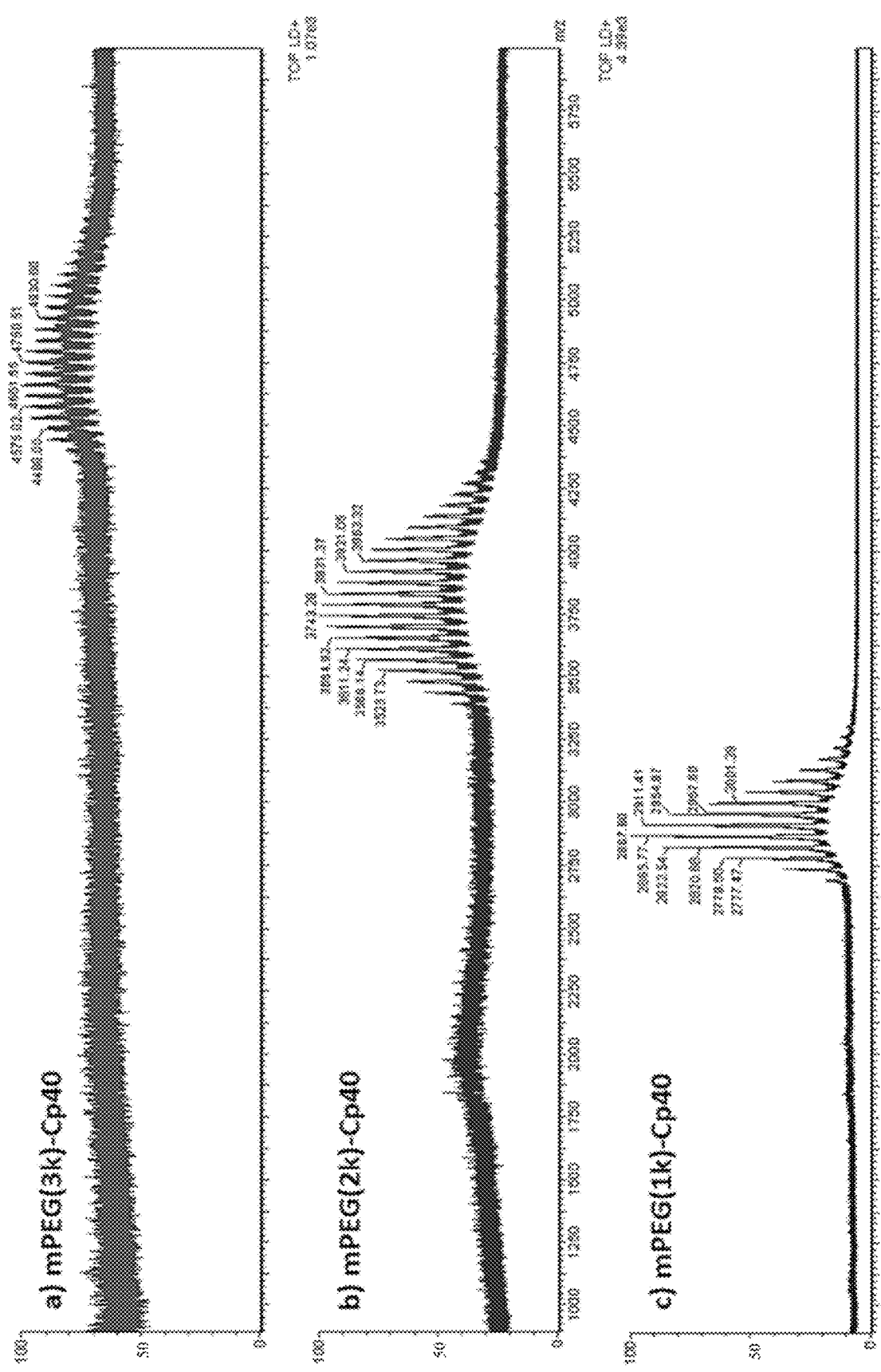
FIG. 2A is a summary of the MALDI spectra of the Cp40-based analogs and shows: panel a) mPEG(3k)-Cp40, panel b) mPEG(2k)-Cp40, panel c) mPEG(1k)-Cp40, panel d) mPEG(1056)-Cp40, and panel e) mPEG(528)-Cp40.
Figure 2A:
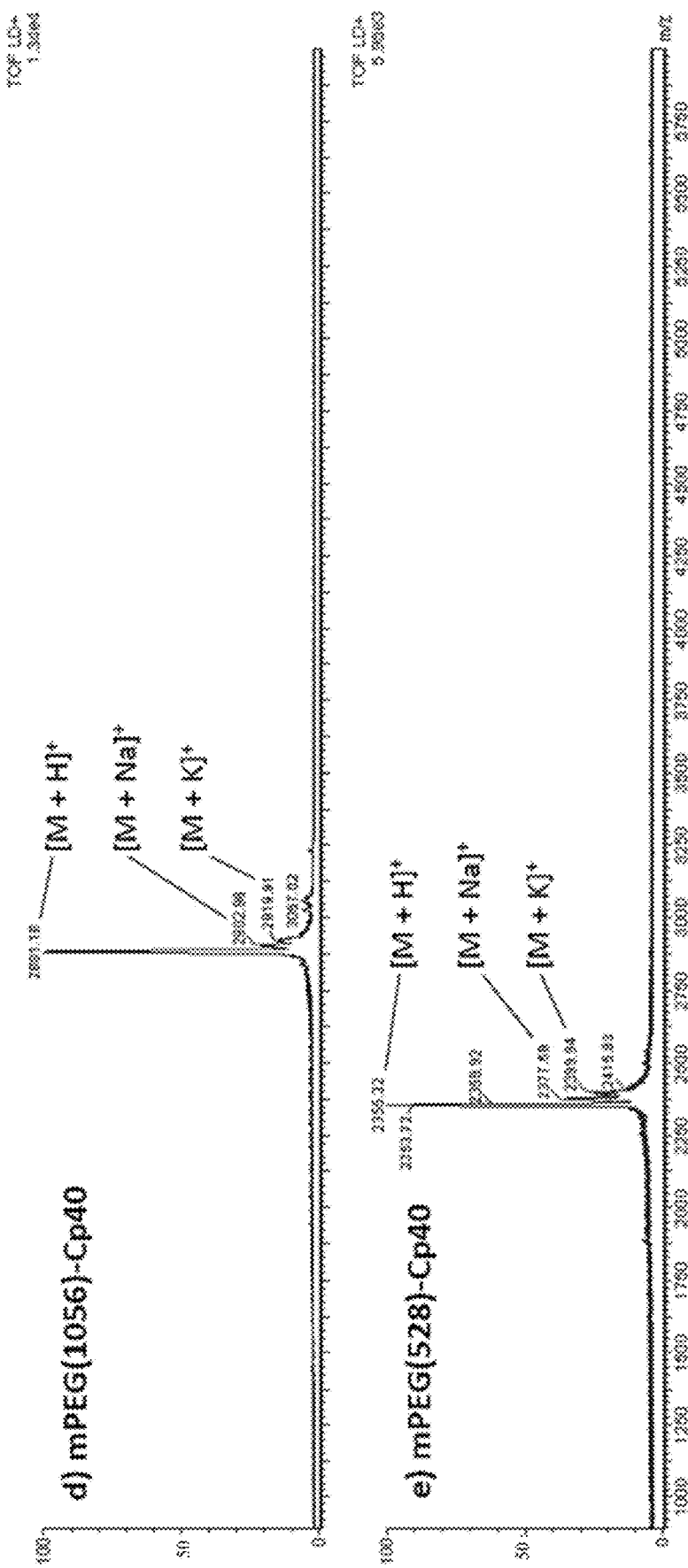
Figure 2B:
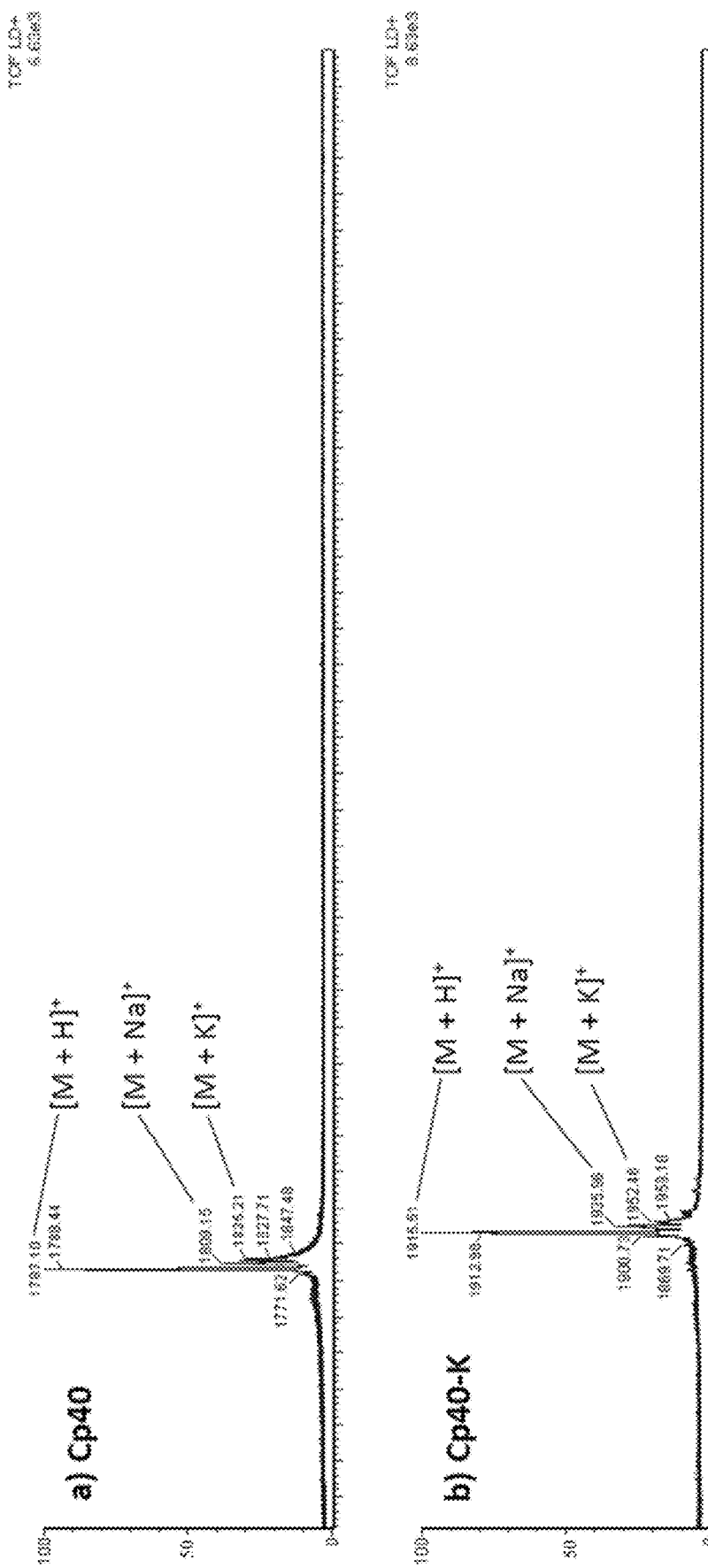
FIG. 2B is a summary of the MALDI spectra of the Cp40-based analogs and shows: panel a) Cp40, panel b) Cp40-K, panel c) Cp40-KK, and panel d) Cp40-KKK.
Figure 2B:
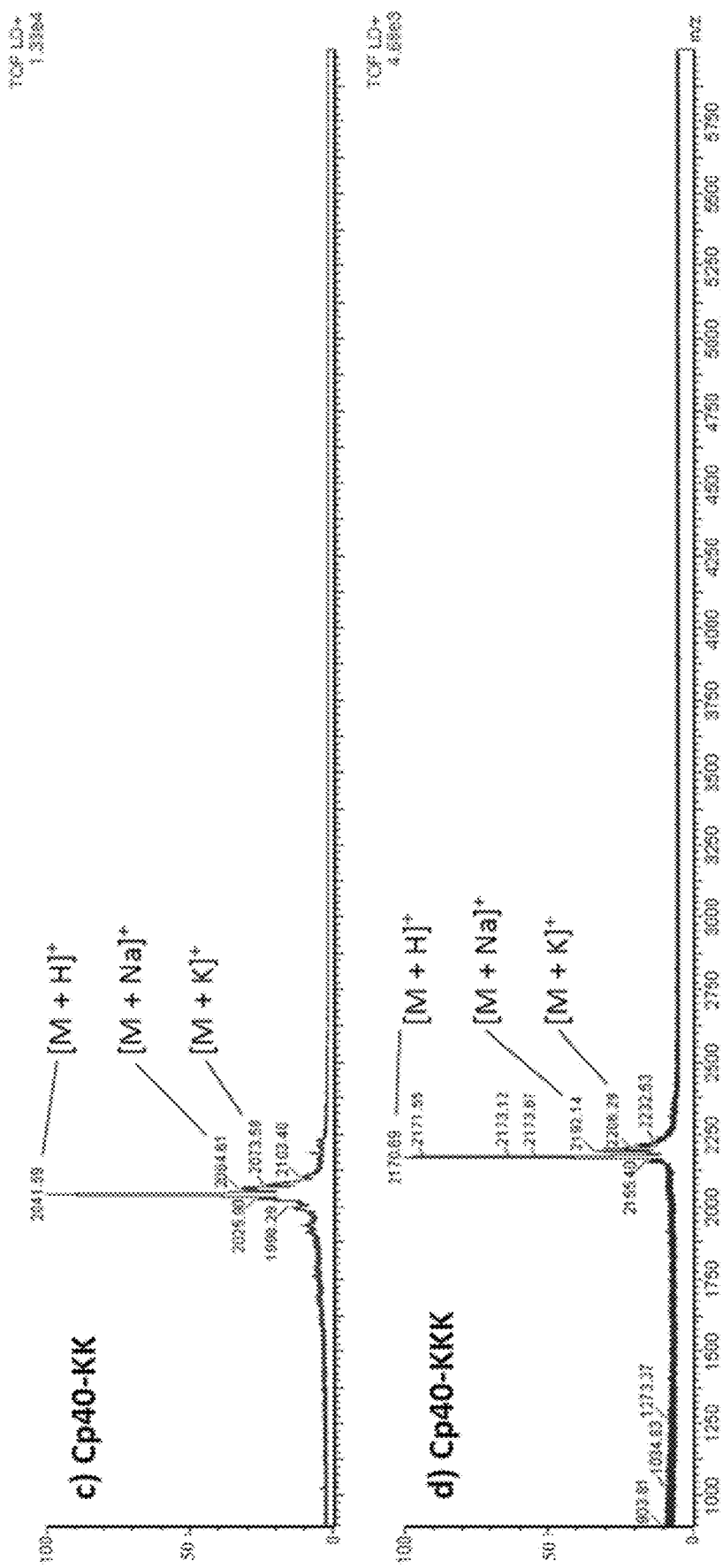

The polymer modification may be a monodisperse PEG or a polydisperse PEG covalently bonded to compstatin or a compstatin analog. For instance, in one embodiment, the terminal modification is a monodisperse PEG having a molecular weight of about 500 to about 1,000. In other embodiments, the modification is a polydisperse PEG having an average molecular weight of about 1,000 to about 3,000. Monodisperse PEG is particularly suitable for use in the present invention because it facilitates purification of the compounds to homogeneity by enabling collection of the PEGylated compounds from a substantially single peak (see, e.g., FIG. 2A, panels a-c as compared with panels d and e).

The compstatin and compstatin analogs of the present invention can be covalently bonded to PEG via a linking group. Such methods are well known in the art. (Reviewed in Kozlowski A. et al., 2001, BioDrugs NM: 419-29; see also, Harris J M and Zalipsky S, eds. Poly(ethylene glycol), Chemistry and Biological Applications, ACS Symposium Series 680 (1997)). Non-limiting examples of acceptable linking groups include an ester group, an amide group, an imide group, a carbamate group, a carboxyl group, a hydroxyl group, a carbohydrate, a succinimide group (including without limitation, succinimidyl succinate (SS), succinimidyl propionate (SPA), succinimidyl carboxymethylate (SCM), succinimidyl succinamide (SSA) and N-hydroxy succinimide (NHS)), an epoxide group, an oxycarbonylimidazole group (including without limitation, carbonyldimidazole (CDI)), a nitro phenyl group (including without limitation, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine. In certain embodiments, the linking group is a succinimide group. In one embodiment, the linking group is NHS.

The compstatin and compstatin analogs of the present invention can alternatively be coupled directly to PEG (i.e., without a linking group) through an amino group, a sulfhydryl group, a hydroxyl group or a carboxyl group. In one embodiment, PEG is coupled to a lysine residue added to the C-terminus of compstatin. In a particular embodiment, PEG is coupled to the compstatin or compstatin analog N-terminus via an amide linkage.

In some embodiments, a modification to compstatin or a compstatin analog comprises both PEGylation and adding one or more hydrophilic or charged amino acid residues to the C-terminus. In certain of these embodiments, PEG is coupled directed to the compstatin or compstatin analog N-terminus via an amide linkage and the PEG has an average molecular weight of about 500 to about 3,000, or an actual molecular weight in that range, if monodisperse. In certain of these embodiments, one or more lysine residues is covalently linked to the C-terminus.

In exemplary embodiments utilizing PEG (mw 500-3,000 DA) as the polymer and lysine as the charged residue, various arrangements of components can be selected as follows (wherein "Comp A" stands for "compstatin analog"):

PEG-Comp A
Comp A-Lys$_{(1-3)}$
PEG-Comp A-Lys$_{(1-3)}$
Comp A-Lys$_{(1-3)}$-PEG
PEG-Comp A-Lys$_{(1-3)}$-PEG The molecular weights of these modified compstatin analogs can be increased or decreased by changing the size of the PEG. The variety of commercially available PEGs will also be appreciated by the skilled person, including polydisperse PEG, monodisperse PEG, heterobifunctional and branched PEG (see, e.g., Creative PEGWorks, Chapel Hill, N.C.; XL-Protein GMBH, Freising, Germany; BroadPharm, San Diego, Calif.)

If the N-terminus of the compstatin analog is not modified with a polymer (i.e. the arrangement in the exemplary series above is Comp A-Lys$_{(1-3)}$ or Comp A-Lys$_{(1-3)}$-PEG), then the N-terminus can be modified in another way. For instance, an albumin-binding small molecule (e.g. ABM2) can be linked to the N-terminus. A particular embodiment of this type features the compstatin analog Cp40 comprising 1-3 charged residues (e.g., Lys) linked to the C-terminus and ABM2 linked to the N-terminus via an amide linkage.

The N-terminal and/or C-terminal modifications described herein increase the solubility of the compstatin or compstatin analog in fluids at a pH of about 7.3 to about 7.5 as compared to the unmodified peptide under equivalent conditions. In certain embodiments, the increase in solubility is at least about 5-fold. In a particular embodiment, the increase in solubility is at least about 10-fold, or at least about 20-fold, or at least about 30-fold, or at least about 40-fold, or at least about 50-fold, or at least 100-fold, 150-fold, 200-fold, 300-fold, 400-fold, or even 500-fold or more, as compared to the equivalent, but unmodified peptide under equivalent conditions. Further, in particular aspects, the compstatin or compstatin analogs containing the N-terminal and/or C-terminal modifications described herein exhibit less than about a 2-fold decrease in complement inhibitory activity as compared to the unmodified peptide under equivalent conditions. Additionally, in preferred embodiments, the compstatin or compstatin analogs containing the N-terminal and/or C-terminal modifications described herein exhibit less than about a 5-fold decrease in C3 binding affinity as compared to the unmodified peptide under equivalent conditions. In some aspects, the compstatin or compstatin analogs containing the N-terminal and/or C-terminal modifications described herein exhibit less than about a 10-fold decrease in C3 binding affinity as compared to the unmodified peptide under equivalent conditions. In other aspects, the compstatin or compstatin analogs containing the N-terminal and/or C-terminal modifications described herein exhibit an increase in C3 binding affinity as compared to the unmodified peptide under equivalent conditions.

As an exemplary illustration, whereas the Cp40 N-terminal modification by conjugation of mPEG resulted in a ~3- to 6-fold decrease in the association constant ($k_a$) with its ligand, C3, no significant variation was observed in the dissociation constant ($k_d$) when compared to the parental compound, Cp40. The lower $k_a$ values were reflected in lower affinity values, especially for the analogs carrying larger PEG chains (mPEG(3k)-Cp40, 7.9 nM; mPEG(2k)-Cp40, 4.4 nM), when compared with Cp40 ($K_D$, 0.5 nM). The apparent lower affinity, however, did not significantly affect the complement inhibitory activity of the analogs (see Table 2 in the Examples). Similarly, the addition of Lys residues to Cp40 did not significantly influence any of the biochemical parameters mentioned above, indicating that the chosen modifications did not induce major changes in the interaction between the analogs and their ligand, C3 (Table 2). It is emphasized here that the dissociation Kd is of greatest significance to the residence time of the compound.

The C- and/or N-terminal modifications described herein can be applied to compstatin itself or any analog thereof. Non-limiting examples of compstatin analogs suitable for use with the N-terminal and/or C-terminal modifications disclosed herein will now be described in further detail.

Compstatin Analogs

The above-described N-terminal and C-terminal modifications can be combined with other modifications of compstatin previously shown to improve activity, thereby producing peptides with significantly improved complement inhibitory activity. For example, in embodiments wherein the N-terminus is not PEGylated, the N-terminus can be acetylated. Additionally, it is known that substitution of Ala for His at position 9 improves activity of compstatin and is a preferred modification of the peptides of the present invention as well.

It was disclosed in WO2004/026328 and WO2007/062249 that Trp and certain Trp analogs at position 4, as well as certain Trp analogs at position 7, especially combined with Ala at position 9, yields many-fold greater activity than that of compstatin. These modifications are used to advantage in the present invention as well.

In particular, peptides comprising 5-fluoro-tryptophan or either 5-methoxy-, 5-methyl- or 1-methyl-tryptophan, or 1-formyl-tryptophan at position 4 have been shown to possess many-fold greater activity than unmodified compstatin. Particularly preferred are 1-methyl and 1-formyl tryptophan. It is believed that an indole 'N'-mediated hydrogen bond is not necessary at position 4 for the binding and activity of compstatin. The absence of this hydrogen bond or reduction of the polar character by replacing hydrogen with lower alkyl, alkanoyl or indole nitrogen at position 4 enhances the binding and activity of compstatin. In certain embodiments, Trp at position 4 of compstatin is replaced with an analog comprising a 1-alkyl substituent, more particularly a lower alkyl (e.g., $C_1$-$C_5$) substituent as defined above. These include, but are not limited to, N( )methyl tryptophan and 5-methyltryptophan. In other embodiments, Trp at position 4 of compstatin is replaced with an analog comprising a 1-alkanoyl substituent, more particularly a lower alkanoyl (e.g., $C_1$-$C_5$) substituent as defined above, e.g., N( )formyl tryptophan, 1-acetyl-L-tryptophan and L-homotryptophan.

It was disclosed in WO2007/062249 that incorporation of 5-fluoro-tryptophan at position 7 in compstatin increased the enthalpy of the interaction between the resulting compstatin analog and C3, relative to compstatin, whereas incorporation of 5-fluoro-tryptophan at position 4 in decreased the enthalpy of this interaction. Accordingly, modifications of Trp at position 7, as described in WO2007/062249, are contemplated as useful modifications in combination with the N-terminal modifications described above.

An exemplary compstatin analog described in WO2007/062249 is: Xaa1-Cys-Val-Xaa2-Gln-Asp-Xaa3-Gly-Xaa4-His-Arg-Cys-Xaa5 (cyclic C2-C12) (SEQ ID NO:2); wherein:

Xaa1 is Ile, Val, Leu, Ac-Ile, Ac-Val, Ac-Leu or a dipeptide comprising Gly-Ile;

Xaa2 is Trp or an analog of Trp, wherein the analog of Trp has increased hydrophobic character as compared with Trp, with the proviso that, if Xaa3 is Trp, Xaa2 is the analog of Trp;

Xaa3 is Trp or an analog of Trp comprising a chemical modification to its indole ring wherein the chemical modification increases the hydrogen bond potential of the indole ring;

Xaa4 is His, Ala, Phe or Trp;

Xaa5 is L-Thr, D-Thr, Ile, Val, Gly, a dipeptide comprising Thr-Asn, or a dipeptide comprising Thr-Ala, or a tripeptide comprising Thr-Ala-Asn, wherein a carboxy terminal —OH of any of the L-Thr, D-Thr, Ile, Val, Gly or Asn optionally is replaced by —$NH_2$; and the two Cys residues are joined by a disulfide bond.

In various embodiments, the analog of Trp of Xaa2 is a halogenated Trp, such as 5-fluoro-1-tryptophan or 6-fluoro-1-tryptophan. In other embodiments, the Trp analog at Xaa2 comprises a lower alkoxy or lower alkyl substituent at the 5 position, e.g., 5-methoxytryptophan or 5-methyltryptophan. In other embodiments, the Trp analog at Xaa 2 comprises a lower alkyl or a lower alkanoyl substituent at the 1 position, with exemplary embodiments comprising 1-methyltryptophan or 1-formyltryptophan. In other embodiments, the analog of Trp of Xaa3 is a halogenated Trp such as 5-fluoro-1-tryptophan or 6-fluoro-1-tryptophan.

In certain embodiments, Xaa2 comprises a lower alkanoyl or lower alkyl substituent at the 1 position of tryptophan, Xaa3 optionally comprises a halogenated tryptophan and Xaa4 comprises Ala.

Other class compstatin analogs with various modifications to SEQ ID Nos: 1 and 2 is described in WO2010/127336. One modification disclosed in that document comprises constraint of the peptide backbone at position 8 of the peptide. In a particular embodiment, the backbone is constrained by replacing glycine at position 8 ($Gly^8$) with N methyl glycine. Another modification disclosed in that document comprises replacing Thr at position 13 with Ile, Leu, Nle (norleucine), N methyl Thr or N methyl Ile. This class of analogs is represented by the sequence:

Xaa1-Cys-Val-Xaa2-Gln-Asp-Xaa3-Gly-Xaa4-His-Arg-Cys-Xaa5

(cyclic C2-C12) (SEQ ID NO:3) in which Gly at position 8 is modified to constrain the backbone conformation of the peptide at that location, and wherein:

Xaa1 is Ile, Val, Leu, Ac-Ile, Ac-Val, Ac-Leu or a dipeptide comprising Gly-Ile;

Xaa2 is Trp or an analog of Trp, wherein the analog of Trp has increased hydrophobic character as compared with Trp;

Xaa3 is Trp, or an analog of Trp comprising a chemical modification to its indole ring wherein the chemical modification increases the hydrogen bond potential of the indole ring;

Xaa4 is His, Ala, Phe or Trp; and

Xaa5 is Thr, Ile, Leu, Nle, N-methyl Thr or N-methyl Ile, wherein a carboxy terminal —OH of any of the Thr, Ile, Leu, Nle, N-methyl Thr or N-methyl Ile optionally is replaced by —NH$_2$.

In embodiments of this class of analog, the Trp analog at Xaa2 comprises a lower alkoxy or lower alkyl substituent at the 5 position, e.g., 5-methoxytryptophan or 5-methyltryptophan; or a lower alkyl or a lower alkanoyl substituent at the 1 position, with exemplary embodiments comprising 1-methyltryptophan or 1-formyltryptophan. In other embodiments, the analog of Trp of Xaa3 is a halogenated tryptophan such as 5-fluoro-1-tryptophan or 6-fluoro-1-tryptophan.

In certain embodiments of this class of analog, the Gly at position 8 is N-methylated, and Xaa1 is Ac-Ile, Xaa2 is 1-methyl-Trp or 1-formyl-Trp, Xaa3 is Trp, Xaa4 is Ala, and Xaa5 is Thr, Ile, Leu, Nle, N-methyl Thr or N-methyl Ile. In particular, Xaa5 may be Ile, N-methyl Thr or N-methyl Ile. In particular, the compstatin analog comprises the analog Cp20: Ac-Ile-[Cys-Val-Trp(Me)-Gln-Asp-Trp-Sar-Ala-His-Arg-Cys]-mIle-NH$_2$ (SEQ ID NO:4)

Another type of modification to compstatin analogs is described in WO2012/040259. One such modification comprises replacement of the C2-C12 disulfide bond with addition of a CH$_2$ to form a homocysteine at C2 or C12, and introduction of a thioether bond, to form a cystathionine, such as a gamma-cystathionine or a delta-cystathionine. Another modification comprises replacement of the C2-C12 disulfide bond with a thioether bond without the addition of a CH$_2$, thereby forming a lantithionine. The analogs comprising the thioether bond demonstrate activity that is substantially the same as that of certain of the disulfide bond analogs and also possess equivalent or improved stability characteristics.

Another class of compstatin analogs particularly suitable as peptide scaffolds for the C-terminal or N-terminal modifications of the present invention in order to produce novel compounds with new pharmacokinetic properties is described in WO2013/036778. This class of analogs is represented by the amino acid sequence Xaa1-Xaa2-Cys-Val-Xaa3-Gln-Xaa4-Xaa5-Gly-Xaa6-His-Xaa7-Cys-Xaa8 (SEQ ID NO: 5), in which the Gly between Xaa5 and Xaa6 optionally is modified to constrain the backbone conformation;

wherein Xaa1 is absent or is Tyr, D-Tyr or Sar;

Xaa2 is Ile, Gly or Ac-Trp;

Xaa3 is Trp or an analog of Trp, wherein the analog of Trp has increased hydrophobic character as compared with Trp;

Xaa4 is an Asp or Asn;

Xaa5 is Trp or an analog of Trp comprising a chemical modification to its indole ring wherein the chemical modification increases the hydrogen bond potential of the indole ring;

Xaa6 is His, Ala, Phe or Trp;

Xaa7 is Arg or Orn; and

Xaa8 is Thr, Ile, Leu, Nle, N-methyl Thr or N-methyl Ile, wherein a carboxy terminal —OH of any of the Thr, Ile, Leu, Nle, or N-methyl Thr or N-methyl Ile optionally is replaced by —NH$_2$, and the peptide is cyclic via a Cys-Cys or thioether bond.

The analog of Trp of Xaa3 may be a halogenated tryptophan, such as 5-fluoro-1-tryptophan or 6-fluoro-1-tryptophan. The Trp analog at Xaa3 may comprise a lower alkoxy or lower alkyl substituent at the 5 position, e.g., 5-methoxytryptophan or 5-methyltryptophan. In other embodiments, the Trp analog at Xaa3 comprises a lower alkyl or a lower alkanoyl substituent at the 1 position, with exemplary embodiments comprising 1-methyltryptophan or 1-formyltryptophan. In other embodiments, the analog of Trp of Xaa5 is a halogenated tryptophan such as 5-fluoro-1-tryptophan or 6-fluoro-1-tryptophan. In some embodiments, the Gly between Xaa5 and Xaa6 is replaced with an N-methyl Gly (Sar).

Reference is made to the exemplary compstatin analogs of this class set forth below:

```
Cp30:
                                    (SEQ ID NO: 6)
Sar-Ile-[Cys-Val-Trp(Me)-Gln-Asp-Trp-Sar-Ala-

His-Arg-Cys]-mIle-NH2

Cp40:
                                    (SEQ ID NO: 7)
DTyr-Ile-[Cys-Val-Trp(Me)-Gln-Asp-Trp-Sar-Ala-

His-Arg-Cys]-mIle-NH2
```

As described in the examples herein, exemplary N- and C-terminally modified analogs in accordance with the present invention were made by modifying the analog Cp40.

TABLE 1

C-terminally modified analogs based on Cp40.

| Analog | Sequence* | Seq. Id. No. |
|---|---|---|
| Cp40** | DTyr-Ile-[Cys-Val-Trp(Me)-Gln-Asn-Trp-Sar-Ala-His-Arg-Cys]-mIle-NH$_2$ | 7 |
| Cp40-K | DTyr-Ile-[Cys-Val-Trp(Me)-Gln-Asn-Trp-Sar-Ala-His-Arg-Cys]-mIle-Lys-NH$_2$ | 8 |
| Cp40-KK | DTyr-Ile-[Cys-Val-Trp(Me)-Gln-Asn-Trp-Sar-Ala-His-Arg-Cys]-mIle-Lys-Lys-NH$_2$ | 9 |
| Cp40-KKK | DTyr-Ile-[Cys-Val-Trp(Me)-Gln-Asn-Trp-Sar-Ala-His-Arg-Cys]-mIle-Lys-Lys-Lys-NH$_2$ | 10 |

*Brackets indicate a Cys-Cys bond.
**Cp40 is shown for comparison.

PEGylation or the addition of Lys residues increased the solubility of Cp40 at physiological pH. Concurrently, the favorable C3 inhibitory activity of Cp40 was unaffected by the modifications, and, surprisingly, the binding affinity of the Lys derivatives towards C3 was even stronger than that of the parental compound Cp40. In addition, the Cp40 variants showed similar or prolonged half-lives after subcutaneous, intravenous, intravitreal, and/or intramuscular administration into non-human primates, while the C3 concentrations were saturated for an extended period of time when the Cp40 variants were used.

The most promising compounds of those assessed as described in the Examples, named mPEG(3k)-Cp40, Cp40-KK, and Cp40-KKK showed a drastic improvement in their solubility (>200-fold) when compared to the parental peptide, Cp40. Most importantly, the novel analogs maintained inhibitory activity and showed improved pharmacokinetic profiles when compared to Cp40. In vivo studies in which non-human primates were administered sc with 2 mg/kg of the individual analogs indicated that mPEG(3k)-Cp40 had a higher $c_{max}$ (~2-fold), longer C3 saturation time (~34 h), slightly extended $t_{1/2}$ by ~15 h, increased $AUC_{0-t}$ (~2.7-fold) and decreased CL/F (~3-fold) than did the Cp40 compound. Among the analogs with additional residues of Lys, Cp40-KKK appeared to be the candidate with the most enhanced characteristics. This effect was even more pronounced when Cp40-KKK was administered by multiple s.c. injections. In vivo pharmacokinetic studies showed that sc administration of Cp40-KKK was associated with higher $c_{max}$ (~2-fold), longer C3 saturation time (~42 h), increased $AUC_{0-t}$ (~2.6-fold) and decreased CL/F (~3-fold) when compared to Cp40. Additional pharmacokinetic studies of the individual analogues, showed that after a single i.v. injection, Cp40-KKK exhibited an $AUC_{0-120}$ h value that was over 3.5-fold greater than Cp40-KK and comparable to mPEG(1k)-Cp40 and mPEG(3k)-Cp40. In these i.v. PK studies, mPEG(3k)-Cp40 appeared to have the most enhanced characteristics, showing an extended $t_{1/2}$ by at least ~30 h, when compared to the other analogues. Moreover, in vivo studies in which non-human primates were administered intravitreally (i.v.t) with 0.5 mg of Cp40-KK, Cp40-KKK, mPEG(1k)-Cp40, or mPEG(3k)-Cp40 showed intravitreal residence times of at least 14 days for the PEGylated Cp40 analogs, with Cp40-KK and Cp40-KKK showing residence times in excess of 73 days. Further still, Cp40-KKK exhibited vitreous residence times at C3 saturating levels even after 90 days.

The overall improvement in solubility and pharmacokinetic profile associated with these novel analogs is bolstered by their potential to reduce the frequency of drug administration and minimize local irritation at the injection site. In addition, the pharmacokinetic studies described herein indicate that the pharmacokinetic parameters favoring long term systemic administration of these compounds, are markedly improved in comparison to Cp40.

Therefore, in particular embodiments, a compound is provided that is based on SEQ ID No:7 in which at least one lysine amino acid is covalently linked to the C-terminus. In some embodiments, at least two lysine amino acids are covalently linked to the C-terminus while in other embodiments, three or more lysine amino acids are covalently lined to the C-terminus. In preferred embodiments, a compound is provided that is based on SEQ ID No:7 in which two or three lysine amino acids are covalently linked to the C-terminus. In other embodiments, a compound is provided that consists of SEQ ID NO:9 or SEQ ID NO:10. In still other embodiments, the compound consists essentially of SEQ ID NO:9 or SEQ ID NO:10. For instance, in an embodiment, a compound is provided having an amino acid sequence represented by SEQ ID NO:10 (Cp40-KKK), wherein the compound exhibits increased solubility, plasma residence time, vitreous residence time, and/or C3-binding as compared to a compound having an amino acid sequence represented by SEQ ID NO:7 (Cp40).

The addition of small polymers, small PEGs and/or the C-terminal addition of hydrophilic or charged residues can be applied to any other class of compstatin analog known in the art. These include, but are not limited to, analogs described in WO2012/155107, WO2013/036778, WO2014/078731, WO2014/078734, WO2014/152931 and WO2017/062879.

The modified compstatin peptides of the present invention may be prepared by various synthetic methods of peptide synthesis via condensation of one or more amino acid residues, in accordance with conventional peptide synthesis methods. For example, peptides are synthesized according to standard solid-phase methodologies. Other methods of synthesizing peptides or peptidomimetics, either by solid phase methodologies or in liquid phase, are well known to those skilled in the art. During the course of peptide synthesis, branched chain amino and carboxyl groups may be protected/deprotected as needed, using commonly known protecting groups. Modification utilizing alternative protecting groups for peptides and peptide derivatives will be apparent to those of skill in the art.

Alternatively, certain peptides of the invention may be produced by expression in a suitable prokaryotic or eukaryotic system. For example, a DNA construct may be inserted into a plasmid vector adapted for expression in a bacterial cell (such as *E. coli*) or a yeast cell (such as *Saccharomyces cerevisiae*), or into a baculovirus vector for expression in an insect cell or a viral vector for expression in a mammalian cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The peptides can also be produced by expression of a nucleic acid molecule in vitro or in vivo. A DNA construct encoding a concatemer of the peptides, the upper limit of the concatemer being dependent on the expression system utilized, may be introduced into an in vivo expression system. After the concatemer is produced, cleavage between the C-terminal Asn and the following N-terminal Gly is accomplished by exposure of the polypeptide to hydrazine.

The peptides produced by gene expression in a recombinant prokaryotic or eukaryotic system may be purified according to methods known in the art. A combination of gene expression and synthetic methods may also be utilized to produce compstatin analogs. For example, an analog can be produced by gene expression and thereafter subjected to one or more post-translational synthetic processes, e.g., to modify the N- or C-terminus or to cyclize the molecule.

Advantageously, peptides that incorporate unnatural amino acids, e.g., methylated amino acids, may be produced by in vivo expression in a suitable prokaryotic or eukaryotic system. For example, methods such as those described by Katragadda & Lambris (2006, *Protein Expression* and Purification 47: 289-295) to introduce unnatural Trp analogs into compstatin via expression in *E. coli* auxotrophs may be utilized to introduce N-methylated or other unnatural amino acids at selected positions of compstatin.

The structure of compstatin is known in the art, and the structures of the foregoing analogs are determined by similar means. Once a particular desired conformation of a short peptide has been ascertained, methods for designing a peptide or peptidomimetic to fit that conformation are well known in the art. Of particular relevance to the present invention, the design of peptide analogs may be further refined by considering the contribution of various side chains of amino acid residues, as discussed above (i.e., for the effect of functional groups or for steric considerations).

It will be appreciated by those of skill in the art that a peptide mimic may serve equally well as a peptide for providing the specific backbone conformation and side chain functionalities required for binding to C3 and inhibiting complement activation. Accordingly, it is contemplated as being within the scope of the present invention to produce C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of the peptides of the invention, which possess the same backbone conformational features and/or other functionalities, so as to be sufficiently similar to the exemplified peptides to inhibit complement activation.

The use of peptidomimetics for the development of high-affinity peptide analogs is well known in the art (see, e.g., Vagner et al., 2008, *Curr. Opin. Chem. Biol.* 12: 292-296; Robinson et al., 2008, *Drug Disc. Today* 13: 944-951) Assuming rotational constraints similar to those of amino acid residues within a peptide, analogs comprising non-amino acid moieties may be analyzed, and their conformational motifs verified, by any variety of computational techniques that are well known in the art.

Uses and Therapeutic Administration of Compstatin Analogs

The complement inhibitory activity of compstatin analogs, peptidomimetics and conjugates may be tested by a variety of assays known in the art. In certain embodiments, the assays described in the Examples are utilized. A non-exhaustive list of other assays is set forth in U.S. Pat. No. 6,319,897, WO99/13899, WO2004/026328, WO2007/062249 and WO2010/127336, including, but not limited to, (1) peptide binding to C3 and C3 fragments; (2) various hemolytic assays; (3) measurement of C3 convertase-mediated cleavage of C3; and (4) measurement of Factor B cleavage by Factor D.

The peptides and peptidomimetics described herein are of practical utility for any purpose for which compstatin itself is utilized, as known in the art. Such uses include, but are not limited to: (1) inhibiting complement activation in the serum, and on cells, tissues or organs of a patient (human or animal), which can facilitate treatment of certain diseases or conditions, including but not limited to, age-related macular degeneration, geographic atrophy, choroidal neovascularization, retinal neovascularization, ocular inflammation, hemodialysis-induced inflammation, glaucoma, uveitis, diabetic retinopathy rheumatoid arthritis, spinal cord injury, traumatic brain injury, cerebral ischemia/reperfusion injury (e.g. stroke), acute polytrauma (hemorrhagic shock), Parkinson's disease, Alzheimer's disease, cancer, sepsis, paroxysmal nocturnal hemoglobinuria, hemolytic disorders of autoimmune etiology (e.g. cold agglutinin disease and wAIHA), psoriasis and respiratory disorders such as asthma, chronic obstructive pulmonary disease (COPD), allergic inflammation, emphysema, bronchitis, bronchiectasis, cystic fibrosis, tuberculosis, pneumonia, respiratory distress syndrome (RDS—neonatal and adult), rhinitis and sinusitis, transplant-associated thrombotic microangiopathy, skin inflammatory diseases, periodontitis, gingivitis, complement-associated kidney diseases; (2) inhibiting complement activation that occurs during cell or organ transplantation, or in the use of artificial organs or implants (e.g., by time-restricted systemic administration before, during and/or after the procedure or by coating or otherwise treating the cells, organs, artificial organs or implants with a peptide of the invention); (3) inhibiting complement activation that occurs during extracorporeal shunting of physiological fluids (blood, urine) (e.g., by time-restricted systemic administration before, during and/or after the procedure or by coating the tubing through which the fluids are shunted with a peptide of the invention); and (4) in screening of small molecule libraries to identify other inhibitors of compstatin activation (e.g., liquid- or solid-phase high-throughput assays designed to measure the ability of a test compound to compete with a compstatin analog for binding with C3 or a C3 fragment).

To implement one or more of the utilities mentioned above, another aspect of the invention features pharmaceutical compositions comprising the compstatin analogs or conjugates described and exemplified herein. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

A particular compstatin analog of the invention may be selected for a particular formulation on the basis of its solubility characteristics. As mentioned above, analogs that are highly soluble in water or buffered saline may be particularly suitable for systemic injection because the injection volume can be minimized. By comparison, analogs with high water solubility and lower solubility in buffered saline could produce a more long-lasting gel, suspension or precipitate for topical application or local injection, such as intraocular injection (including intravitreal injection).

As such, in particular embodiments, the compstatin analogs based on Cp40 are administered via subcutaneous, intravenous, intraocular (including intravitreal), intramuscular injection, periodontal administration (including gingival administration or intrapapillary infiltration injection), or topical administration. In yet other embodiments, the Cp40 analogs are delivered orally. In some embodiments, the Cp40-based analogs are administered as a single oral, subcutaneous, intravenous, intraocular (including intravitreal), intramuscular injection, periodontal administration, or topical administration. In other embodiments, the Cp40-based analogs are administered via multiple oral, subcutaneous, intravenous, intraocular (including intravitreal), intramuscular injections, periodontal or topical administrations. In yet other embodiments, a Cp40-based analog is administered via an initial subcutaneous, intravenous, or intramuscular loading dose combined with repeated oral, intramuscular, subcutaneous or intravenous dosing for an extended period of time to allow for lower dosing of the analogs and less frequent dosing intervals as compared to administration methods previously described for known compstatin analogs. In still other embodiments, maintenance dosing is accomplished via Cp40 analog delivery by subcutaneous infusion pumps or ocular implants (see, e.g., US2016/0060297, and U.S. Pat. No. 6,692,759).

The formulations of the pharmaceutical compositions may be prepared by any method known or hereafter developed in the art of pharmaceutical technology. In general, such preparatory methods include the step of bringing the active ingredient into association with a carrier or one or more other accessory ingredients, and then, if necessary or desirable, shaping or packaging the product into a desired single- or multi-dose unit.

The pharmaceutical compositions useful for practicing the invention may be administered to deliver a dose of between 0.125 mg/kg and 50 mg/kg body weight as a single bolus, or an intravitreal dose of between 1 g and about 10 mg, or in a repeated regimen, or a combination thereof as readily determined by the skilled artisan. In certain embodiments, the dosage comprises at least 0.05 mg/kg, 0.1 mg/kg, or at least 0.2 mg/kg, or at least 0.3 mg/kg, or at least 0.4 mg/kg, or at least 0.5 mg/kg, or at least 0.6 mg/kg, or at least 0.7 mg/kg, or at least 0.8 mg/kg, or at least 0.9 mg/kg, or at least 1 mg/kg, or at least 2 mg/kg, or at least 3 mg/kg, or at least 4 mg/kg, or at least 5 mg/kg, or at least 6 mg/kg, or at least 7 mg/kg, or at least 8 mg/kg, or at least 9 mg/kg, or at least 10 mg/kg, or at least 15 mg/kg, or at least 20 mg/kg, or at least 25 mg/kg, or at least 30 mg/kg, or at least 35 mg/kg, or at least 40 mg/kg, or at least 45 mg/kg, or at least 50 mg/kg, on a daily basis or on another suitable periodic regimen.

It has been discovered that administration of the Cp40-based analogs disclosed herein (e.g., PEG(1K)-Cp40, PEG(3K)-Cp40, Cp40-KK, or Cp40-KKK) have extended plasma residence times and extended intravitreal residence times as compared to previously known compstatin analogs can therefore be administered intravenously, intravitreally, intramuscularly, and/or subcutaneously at lower therapeutically effective doses and less frequent dosing intervals. As one having ordinary skill in the art will appreciate, the specific route of administration may influence the dose required for therapeutic effectiveness.

In one embodiment, the invention envisions intravenous or subcutaneous administration of a Cp40-based analog, as described herein, at a therapeutically effective dose that is between about 0.125 mg/kg and about 10 mg/kg, e.g., 0.125 mg/kg, 0.25 mg/kg, 0.5 mg/kg, 0.75 mg/kg, 1 mg/kg, 1.25 mg/kg, 1.5 mg/kg, 1.75 mg/kg, 2 mg/kg, 2.25 mg/kg, 2.5 mg/kg, 2.75 mg/kg, 3 mg/kg, 3.25 mg/kg, 3.5 mg/kg, 3.75 mg/kg, 4 mg/kg, 4.25 mg/kg, 4.5 mg/kg, 4.75 mg/kg, 5 mg/kg, 5.25 mg/kg, 5.5 mg/kg, 5.75 mg/kg, 6 mg/kg, 6.25 mg/kg, 6.5 mg/kg, 6.75 mg/kg, 7 mg/kg, 7.25 mg/kg, 7.5 mg/kg, 7.75 mg/kg, 8 mg/kg, 8.25 mg/kg, 8.5 mg/kg, 8.75 mg/kg, 9 mg/kg, 9.25 mg/kg, 9.5 mg/kg, 9.75 mg/kg, or 10 mg/kg. In a preferred embodiment, the Cp40-based analog is administered via intravenous or subcutaneous delivery (e.g., injection or infusion) at a therapeutically effective dose that is between about 0.25 mg/kg and about 5 mg/kg. In another embodiment, the therapeutically effective dose is between about 0.5 mg/kg and about 5 mg/kg. In yet another embodiment, the therapeutically effective dose is between about 0.5 mg/kg and 4 mg/kg or between about 0.5 mg/kg and about 3 mg/kg. For instance, in one particular embodiment, the Cp40-based analog (e.g., PEG(1K)-Cp40, PEG(3K)-Cp40, Cp40-KK, or Cp40-KKK) is injected i.v. or s.c. to a human at a dose of about 3 mg/kg/24 hours.

In another embodiment, the invention envisions intramuscular administration of a Cp40-based analog, as described herein, at a therapeutically effective dose that is between about 0.25 mg/kg and about 50 mg/kg, e.g., 0.25 mg/kg, 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg, 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 15.5 mg/kg, 16 mg/kg, 16.5 mg/kg, 17 mg/kg, 17.5 mg/kg, 18 mg/kg, 18.5 mg/kg, 19 mg/kg, 19.5 mg/kg, 20 mg/kg, 20.5 mg/kg, 21 mg/kg, 21.5 mg/kg, 22 mg/kg, 22.5 mg/kg, 23 mg/kg, 23.5 mg/kg, 24 mg/kg, 24.5 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, or 50 mg/kg. In a preferred embodiment, the Cp40-based analog is administered via intramuscular delivery (e.g., injection) at a therapeutically effective dose that is between about 0.25 mg/kg and about 35 mg/kg. In another embodiment, the therapeutically effective dose is between about 0.25 mg/kg and 30 mg/kg. In yet another embodiment, the therapeutically effective dose is between about 0.25 mg/kg and 10 mg/kg. In still other embodiments, the therapeutically effective dose is between about 0.25 mg/kg and 5 mg/kg. For instance, in one particular embodiment, the Cp40-based analog (e.g., PEG(1K)-Cp40, PEG(3K)-Cp40, Cp40-KK, or Cp40-KKK) is injected i.m. at a dose of about 2.5 mg/kg In yet another embodiment, the invention envisions intravitreal administration of a Cp40-based analog, as described herein, at a therapeutically effective dose that is between about 1 g and about 10 mg, e.g., 1 g, 1.25 g, 1.5 g, 1.75 g, 2 g, 2.25 g, 2.5 g, 2.75 g, 3 g, 3.25 g, 3.5 g, 3.75 g, 4 g, 4.25 g, 4.5 g, 4.75 g, 5 g, 5.25 g, 5.5 g, 5.75 g, 6 g, 6.25 g, 6.5 g, 6.75 g, 7 g, 7.25 g, 7.5 g, 7.75 g, 8 g, 8.25 g, 8.5 g, 8.75 g, 9 g, 9.25 g, 9.5 g, 9.75 g, 10 g, 20 g, 30 g, 40 g, 50 g, 60 g, 70 g, 80 g, 90 g, 100 g, 150 g, 200 g, 250 g, 300 g, 350 g, 400 g, 450 g, 500 g, 550 g, 600 g, 650 g, 700 g, 750 g, 800 g, 850 g 900 g, 950 g, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, or 10 mg; preferably, the dose is between about 1 g and about 2,000 g, e.g., about 1 g to about 2,000 g or about 100 g to about 1,500 g, or about 500 g to about 1,200 g, or about 500 g to about 1,000 g. In some embodiments, the therapeutically effective dose of Cp40-based analog is delivered via intravitreal administration is at least about 0.02 mg, e.g., at least about 0.02 mg, 0.03 mg, 0.04 mg, 0.05 mg, 0.06 mg, 0.07 mg, 0.08 mg, 0.09 mg, 0.1 mg, 0.15 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, or 1 mg. For instance, in one particular embodiment, the Cp40-based analog (e.g., PEG(1K)-Cp40, PEG(3K)-Cp40, Cp40-KK, or Cp40-KKK) is injected i.v.t. at a dose of about 1 mg.

In another embodiment, the invention envisions oral administration of a Cp40-based analog, as described herein, at a therapeutically effective dose that is between about 1 mg/kg and about 20 mg/kg, e.g., 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg, 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 15.5 mg/kg, 16 mg/kg, 16.5 mg/kg, 17 mg/kg, 17.5 mg/kg, 18 mg/kg, 18.5 mg/kg, 19 mg/kg, 19.5 mg/kg, or 20 mg/kg. In a preferred embodiment, the Cp40-based analog is administered via oral delivery at a therapeutically effective dose that is between about 1 mg/kg and about 10 mg/kg. For instance, in one particular embodiment, the Cp40-based analog (e.g., PEG(1K)-Cp40, PEG(3K)-Cp40, Cp40-KK, or Cp40-KKK) is delivered orally to a human at a dose of about 1 and 5 mg/kg. In some embodiments, the oral dose described herein is administered once. In other embodiments, it is administered daily.

In another embodiment, the invention envisions periodontal administration, such as intrapapillary infiltration, of a Cp40-base analog, as described herein, at a therapeutically effective dose that is between about 1 g and about 1,000 g, e.g., 1 g, 5 g, 10 g, 15 g, 20 g, 25 g, 30 g, 35 g, 40 g, 45 g, 50 g, 55 g, 60 g, 65 g, 70 g, 75 g, 80 g, 85 g, 90 g, 95 g, 100 g, 110 g, 120 g, 130 g, 140 g, 150 g, 160 g, 170 g, 180 g, 190 g, 200 g, 210 g, 220 g, 230 g, 240 g, 250 g, 260 g, 270 g, 280 g, 290 g, 300 g, 310 g, 320 g, 330 g, 340 g, 350 g, 360 g, 370 g, 380 g, 390 g, 400 g, 410 g, 420 g, 430 g, 440 g, 450 g, 460 g, 470 g, 480 g, 490 g, 500 g, 550 g, 600 g, 650 g, 700 g, 750 g, 800 g, 850 g, 900 g, 950 g, or 1,000 g. For example, the Cp40-based analog can be administered periodontally to a human at a dose of between about 5 g and about 500 g (e.g., delivered into the interdental papilla by injection). In a preferred embodiment, the Cp40-based analog is delivered periodontally to a human at a dose of between about 10 g/interdental papilla and about 200 g/interdental papilla or at a dose of between about 20 g/interdental papilla and about 100 g/interdental papilla. For instance, in one particular embodiment, the Cp40-based analog (e.g., PEG(1K)-Cp40, PEG(3K)-Cp40, Cp40-KK, or Cp40-KKK) is delivered periodontally to a human at a dose of about 25 g/interdental papilla or about 50 g/interdental papilla.

In one embodiment, the invention envisions administration of a dose that results in a serum concentration of the Cp40-based analog between about 0.01 µM and about 30 µM in an individual. In certain embodiments, the combined dose and regimen will result in a serum concentration, or an average serum concentration over time, of the Cp40-based analog of at least about 0.01 µM, or at least about 0.02 µM, or at least about 0.03 µM, or at least about 0.04 µM, or at least about 0.05 µM, or at least about 0.06 µM, or at least about 0.07 µM, or at least about 0.08 µM, or at least about 0.09 µM, or at least about 0.1 µM, 0.11 µM, or at least about 0.12 µM, or at least about 0.13 µM, or at least about 0.14 µM, or at least about 0.15 µM, or at least about 0.16 µM, or at least about 0.17 µM, or at least about 0.18 µM, or at least about 0.19 µM, or at least about 0.2 µM, or at least about 0.3 µM, or at least about 0.4 µM, or at least about 0.5 µM, or at least about 0.6 µM, or at least about 0.7 µM, or at least about 0.8 µM, or at least about 0.9 µM, or at least about 1 µM or at least about 1.5 µM, or at least about 2 µM, or at least about 2.5 µM, or at least about 3 µM, or at least about 3.5 µM, or at least about 4 µM, or at least about 4.5 µM, or at least about 5 µM, or at least about 5.5 µM, or at least about 6 µM, or at least about 6.5 µM, or at least about 7 µM, or at least about 7.5 µM, or at least about 8 µM, or at least about 8.5 µM, or at least about 9 µM, or at least about 9.5 µM, or at least about 10 µM, or at least about 10.5 µM, or at least about 11 µM or at least about 11.5 µM, or at least about 12 µM, or at least about 12.5 µM, or at least about 13 µM, or at least about 13.5 µM, or at least about 14 µM, or at least about 14.5 µM, or at least about 15 µM, or at least about 15.5 µM, or at least about 16 µM, or at least about 16.5 µM, or at least about 17 µM, or at least about 17.5 µM, or at least about 18 µM, or at least about 18.5 µM, or at least about 19 µM, or at least about 19.5 µM, or at least about 20 µM, or at least about 20.5 µM, or at least about 21 µM or at least about 21.5 µM, or at least about 22 µM, or at least about 22.5 µM, or at least about 23 µM, or at least about 23.5 µM, or at least about 24 µM, or at least about 24.5 µM, or at least about 25 µM, or at least about 25.5 µM, or at least about 26 µM, or at least about 26.5 µM, or at least about 27 µM, or at least about 27.5 µM, or at least about 28 µM, or at least about 28.5 µM, or at least about 29 µM, or at least about 29.5 µM, or at least about 30 µM. In certain embodiments, the combined dose and regimen will result in a serum concentration, or an average serum concentration over time, of the Cp40-based analog of up to about 0.1 µM, or up to about 0.11 µM, or up to about 0.12 µM, or up to about 0.13 µM, or up to about 0.14 µM, or up to about 0.15 µM, or up to about 0.16 µM, or up to about 0.17 µM, or up to about 0.18 µM, or up to about 0.19 µM, or up to about 0.2 µM, or up to about 0.3 µM, or up to about 0.4 µM, or up to about 0.5 µM, or up to about 0.6 µM, or up to about 0.7 µM, or up to about 0.8 µM, or up to about 0.9 µM, or up to about 1 µM or up to about 1.5 µM, or up to about 2 µM, or up to about 2.5 µM, or up to about 3 µM, or up to about 3.5 µM, or up to about 4 µM, or up to about 4.5 µM, or up to about 5 µM, or up to about 5.5 µM, or up to about 6 µM, or up to about 6.5 µM, or up to about 7 µM, or up to about 7.5 µM, or up to about 8 µM, or up to about 8.5 µM, or up to about 9 µM, or up to about 9.5 µM, or up to about 10 µM, or up to about 10.5 µM or up to about 11 µM or up to about 11.5 µM, or up to about 12 µM, or up to about 12.5 µM, or up to about 13 µM, or up to about 13.5 µM, or up to about 14 µM, or up to about 14.5 µM, or up to about 15 µM, or up to about 15.5 µM, or up to about 16 µM, or up to about 16.5 µM, or up to about 17 µM, or up to about 17.5 µM, or up to about 18 µM, or up to about 18.5 µM, or up to about 19 µM, or up to about 19.5 µM, or up to about 20 µM, or up to about 20.5 µM or up to about 21 µM or up to about 21.5 µM, or up to about 22 µM, or up to about 22.5 µM, or up to about 23 µM, or up to about 23.5 µM, or up to about 24 µM, or up to about 24.5 µM, or up to about 25 µM, or up to about 25.5 µM, or up to about 26 µM, or up to about 26.5 µM, or up to about 27 µM, or up to about 27.5 µM, or up to about 28 µM, or up to about 28.5 µM, or up to about 29 µM, or up to about 29.5 µM, or up to about 20 µM.

Suitable ranges include about 0.1 to about 30 µM, or about 1 to about 29 µM, or about 2 to about 28 µM, or about 3 to about 27 µM, or about 4 to about 26 µM, or about 5 to about 25 µM, or about 6 to about 24 µM, or about 7 to about 23 µM, or about 8 to about 22 µM, or about 9 to about 21 µM, or about 10 to about 20 µM, or about 11 to about 19 µM, or about 12 to about 18 µM, or about 13 to about 17 µM, or about 1 to about 5 µM, or about 5 to about 10 µM, or about 10 to about 15 µM, or about 15 to about 20 µM, or about 20 to about 25 µM, or about 25 to about 30 µM. While the precise dosage administered will vary depending upon any number of factors, including but not limited to, the type of patient and type of disease state being treated, the age of the patient and the route of administration, such dosage is readily determinable by the person of skill in the art.

The pharmaceutical composition containing the Cp40-based analog can be administered to a patient as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the patient, as described above. However, and as noted above, the Cp40-based analogs of the instant disclosure can be administered at less frequent intervals as compared to previously known compstatin analogs.

For instance, in some embodiments, the intravenous, intramuscular, intraocular (including intravitreal), subcutaneous, periodontally (including gingival administration or intrapapillary infiltration) or topical administration of a pharmaceutical composition containing the Cp40-based analog is via a single injection. In other embodiments, the Cp40-based analog is delivered orally. Additionally, and given the extended residence time of the presently described Cp40-based analogs (i.e., mPEGylated and/or Lys-containing Cp40-based analogs), the invention envisions long term systemic administration of these Cp40-based analogs, wherein the Cp40-based analogs are delivered by oral, intravenous, intraocular (including intravitreal), subcutaneous, intramuscular, periodontally (including gingival administration or intrapapillary infiltration) or topical administration routes at the above-described therapeutic doses via multiple deliveries (e.g., by mouth or injection) over time in order to provide a therapeutically effective maintenance dose of the Cp40-based analogs depending on the type and age of patient and the type and severity of disease treated. Thus, in some embodiments, a Cp40-based analog (e.g., PEG(1K)-Cp40, PEG(3K)-Cp40, Cp40-KK, or Cp40-KKK) is delivered intravenously, intraocularly (including intravitreally), subcutaneously, intramuscularly, periodontally (e.g., via intrapapillary infiltration), or topically, by multiple injections of a pharmaceutical composition comprising the analog administered once every about 12 hours to about once every three months, e.g., once every 12 hours, once every 24 hours, once every 2 days, once every 3 days, once every 4 days, once every 5 days, once every 6 days, once every 7 days, once every 8 days, once every 9 days, once every 10 days, once every 2 weeks, once every 3 weeks, once every month, once every two months, once every three months. In other embodiments, the Cp40-based analog is delivered orally by ingestion of a pharmaceutical composition comprising the analog administered once every about 12 hours to about once every three months, e.g., once every 12 hours, once every 24 hours, once every 2 days, once every 3 days, once every 4 days, once every 5 days, once every 6 days, once every 7 days, once every 8 days, once every 9 days, once every 10 days, once every 2 weeks, once every 3 weeks, once every month, once every two months, once every three months.

Also provided herein are delivery methods that include a combination of administration routes and doses. For instance, provided herein are methods of systemic treatment of pharmaceutical compositions containing the Cp40-based analogs of the instant disclosure (e.g., PEG(1K)-Cp40, PEG(3K)-Cp40, Cp40-KK, or Cp40-KKK) that includes an initial saturating dose followed by multiple dosing at lower therapeutically effective doses and less frequent dosing intervals. This novel method of systemic treatment would provide for prolonged in vivo maintenance/control of complement inhibition. To this end, in some embodiments, a first loading dose of a Cp40-based analog is subcutaneously, intravenously, or intramuscularly administered at a higher therapeutically effective dose selected from the ranges described above, which is then followed by intramuscular or oral administration at regular dosing intervals. In one such embodiment, a pharmaceutical composition containing one of the Cp40-based analogs discussed herein (e.g., Cp40-KKK) is injected subcutaneously or intravenously at an initial therapeutically effective dose of at least about 0.5 to about 3 mg/kg and thereafter administered orally or intramuscularly at a therapeutically effective maintenance dose of between about 0.25 mg/kg and about 50 mg/kg, wherein maintenance dose is delivered once every 2 days to 3 months, e.g., once every 2 days, 3 days, 3 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 42 days, 45 days, 50 days, 56 days, 60 days, 65 days, 70 days, 77 days, 80 days, 84 days, or 90 days. For instance, in one particular embodiment, a pharmaceutical composition containing Cp40-KKK is administered i.v. at a saturating dose of about 0.5 mg/kg to about 3 mg/kg and then subsequently administered i.m. weekly or every two weeks at a maintenance dose of about 0.5 to about 10 mg/kg.

As noted above, pharmaceutical compositions containing the Cp40-based analogs that are useful in the methods of the invention may be administered systemically in oral, parenteral, ophthalmic or intraocular (including intravitreal), intravenous, subcutaneous, intramuscular (i.m.), periodontal (e.g., intrapapillary infiltration injection), suppository, aerosol, topical, transdermal or other similar formulations. Such pharmaceutical compositions may contain pharmaceutically acceptable carriers and other ingredients known to enhance and facilitate drug administration. Other formulations, such as nanoparticles, liposomes, resealed erythrocytes, and immunologically based systems may also be used to administer a compstatin analog according to the methods of the invention.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), phosphate buffered saline (PBS), or Ringer's solution.

Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In general, the composition should be sterile, and should be fluid so that easy syringability exists. Preferred pharmaceutical formulations are stable under the conditions of manufacture and storage and may be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Formulations of a pharmaceutical composition suitable for oral administration comprise the active ingredient combined with a pharmaceutically acceptable carrier, in a variety of dosage forms, including but not limited to pills, tablets, granules, powders, capsules, dispersions, suspensions, solutions, emulsions, microemulsions, gels and films, to name a few. Such dosage forms typically include carriers, excipients, and or permeation enhancers to facilitate formulation and delivery of the active ingredients.

The pharmaceutically acceptable carriers are selected from proteins, carbohydrates, lipids, organic and inorganic molecules, and combinations thereof. The active ingredients can be combined with the carrier in an appropriate diluent to form a solution or a suspension. Such liquid formulations can be viscous or non-viscous depending on the amount and the carrier used. The liquid formulations can be used directly or can be further formulated into an appropriate capsule, gel capsule or solid by methods know to those skilled in the art. Alternatively, solid formulations can be made by combining solid components. Such solid formulations can be used as a powder or formulated into granules, capsules, tablets or films any one of which can be made as a time release formulation.

Suitable proteins for use as carriers in oral dosage forms include milk proteins such as casein, sodium caseinate, whey, reduced lactose whey, whey protein concentrate, gelatin, soy protein (isolated), brown algae protein, red algae protein, baker's yeast extract and albumins. Suitable carbohydrates include celluloses such as methylcellulose, sodium carboxymethylcellulose, carboxymethylcellulose, hydroxypropylcellulose, hydroxypropylmethylcellulose, cellulose acetate and ethyl cellulose, starches such as cornstarch, potato starch, tapioca starch, wheat starch, acid modified starch, pregelatinized starch and unmodified starch, alginates such as ammonium alginate, sodium alginate, and calcium alginate, glutens such as corn gluten and wheat gluten, gums such as acacia (gum Arabic), gum ghatti, guar gum, karaya gum (sterculia gum) and gum (tragacanth), insoluble glucose isomerase enzyme preparations, sugars such as corn sugar, invert sugar, corn syrup, high fructose corn syrup, and sodium gluconate. Suitable lipids include tocopherols such as a-tocopherol acetate, short-, medium- and long-chain fatty acids and esters thereof, fatty alcohols and ethers thereof, oils such as coconut oil (refined), soybean oil (hydrogenated) and rapeseed oil, aluminum palmitate, dilauryl thiodipropionate, enzyme-modified lecithin, calcium stearate, enzyme-modified fats, glyceryl palmitostereate, lecithin, mono- and diglycerides, glycerin and waxes such as beeswax (yellow and white), candelilla wax and carnauba wax and vegetable oil. Suitable organic and inorganic substances include methyl and vinyl pyrrolidones such as polyvinylpyrrolidone, methylsulfonyl methane, dimethylsulfoxide and related compounds, hydroxy and polyhydroxy acids such as polylactic acid, among many others.

In some embodiments, oral dosage forms of the pharmaceutical compositions provided herein contain one or more permeation enhancers and/or lipid excipients to increase the bioavailability of the compositions after oral administration such as those described in Maher et al. (2016, Adv. Drug Deliv. Rev. 106:277-319). Exemplary permeation enhancers suitable for use herein include $C_{12}E_9$, caprylocaproyl PEG 8 glycerides, citric acid, dodecyl-β-D-maltopyranoside (DDM), glyceryl monocaprate, laurylocarnitine, n-tetradecyl β-D-maltopyranoside (TDM), N-trimethylated chitosan, palmitoylcarnitine, penetratin (D-penetratin), SNAC, sodium caprate ($C_{10}$), sodium caprylate ($C_8$), sodium cholate, sodium deoxycholate, sodium dodecyl sulphate, sodium taurocholate, and sucrose monolaurate. Exemplary lipid excipients suitable for use herein include polyoxylglycerides (e.g., polyoxyl stearate, polyethylene glycol monostearate, caprylocaproyl polyoxyl-8 glycerides, caprylocaproyl macrogol-8 glycerides, lauraoyl polyoxylglycerides, stearoyl polyoxyglycerides, oleoyl polyoxyl-6 glycerides, linoleoyl polyoxyl-6 glycerides, and lauroyl polyoxyl-6 glycerides), propylene glycol esters (e.g., propylene glycol monocaprylate type I, propylene glycol monocaprylate type II, propylene glycol monolaurate type I, and propylene glycol monolaurate type II), polyglycerol esters (e.g., polyglyceryl-3 dioleate), glycerides (e.g., monoglycerides, diglycerides, glycerol monostearate 40-55 type I, medium chain triglycerides, propylene glycol dicaprylate/dicaprate, propylene glycol dicaprylocaprate, glyceryl monolinoleate, and glyceryl monooleate type 40), and hydroalcoholic solvents (e.g., diethylene glycol monoethyl ether).

In some embodiments, pharmaceutical compositions formulated for oral delivery may include nanoparticles as a drug delivery system. Polymers suitable for use in the coating of nano-carriers encapsulating the Cp-40 analogs provided herein include, but are not limited to carbopol, chitosan, cholesteryl polymers, cyclodextrin, hydroxypropyl methylcellulose phthalate, poly(ethyl cyanoacrylate), polyethylene glycol, polyacrylic acid, polylactide-co-glycolide, and polyallylamin (see, for example, Gupta et al., 2013, Drug Deliv. 20(6):237-246).

For topical applications, the pharmaceutical compositions provided herein may be formulated in a suitable ointment containing the pharmaceutically active component suspended or dissolved in one or more pharmaceutically acceptable carriers. Pharmaceutically acceptable carriers for topical administration of the compstatin or compstatin analogs disclosed herein include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For local delivery to the eye, the pharmaceutical compositions provided herein may be appropriately formulated, for example (but not limited to), in isotonic, pH adjusted sterile saline or water, either with or without a preservative such as benzylalkonium chloride. Alternatively, for ophthalmic uses, the pharmaceutical compositions may be formulated in an ointment such as petrolatum or as eye drops.

Methods of local administration to the eye include, e.g., choroidal injection, transscleral injection or placing a scleral patch, selective arterial catheterization, eye drops or eye ointments, intraocular administration including transretinal, subconjunctival bulbar, intravitreal injection, suprachoroidal injection, subtenon injection, scleral pocket and scleral cutdown injection, by osmotic pump, etc. The Cp40-analogs can also be alternatively administered intravascularly, such as intravenously (IV) or intraarterially. In choroidal injection and scleral patching, the clinician or handler uses a local approach to the eye after initiation of appropriate anesthesia, including painkillers and ophthalmoplegics. A needle containing the pharmaceutical composition is directed into the subject's choroid or sclera and inserted under sterile conditions. When the needle is properly positioned, the Cp40 analog is injected into either or both of the choroid or sclera. When using either of these methods, the clinician or handler can choose a sustained release or longer acting formulation. Thus, the procedure can be repeated only every several months or several years, depending on the subject's tolerance of the treatment and response.

Intraocular administration of drugs is well known in the art. See, e.g., U.S. Pat. Nos. 5,632,984 and 5,770,589 and U.S. Pub. No. 2016/0060297 A1. U.S. Pat. No. 6,378,526 provides methods for intrascleral injection of a therapeutic or diagnostic material at a location overlying the retina, which provide a minimally invasive technique for delivering the agent to the posterior segment of the eye.

In certain embodiments, a pharmaceutical composition containing a Cp40 analog of the present invention is delivered to the vicinity of the eye, e.g., in close proximity to the posterior segment of the eye. The "vicinity of the eye" refers to locations within the orbit, which is the cavity within the skull in which the eye and its appendages are situated. Typically the compositions would be delivered close to their intended target within the eye, e.g., close to (within several millimeters of) the portion of the sclera that overlies the posterior segment of the eye, or immediately adjacent to the exterior surface of the sclera. In a preferred embodiment, the pharmaceutical compositions of the present invention are delivered into the vitreous cavity of the eye (i.e., intravitreally).

A number of polymeric delivery vehicles for providing controlled release have been used in an ocular context and can be used to administer the pharmaceutical compositions of the invention. Various polymers, e.g., biocompatible polymers, which may be biodegradable, can be used. For example, U.S. Pat. No. 6,692,759 describes methods for making an implantable device for providing controlled release of therapeutic agents in the eye. Other useful polymers and delivery systems for ocular administration of a therapeutic agent have been described. The active agent may be released as the polymer degrades. Polymers that have been used for drug delivery include, but are not limited to, poly(lactic-co-glycolic acid), polyanhydrides, ethylene vinyl acetate, polyglycolic acid, chitosan, polyorthoesters, polyethers, polylactic acid, and poly (beta amino esters). Peptides, proteins such as collagen and albumin, and dendrimers (e.g., PAMAM dendrimers) have also been used. Any of these can be used in various embodiments of the invention.

Poly(ortho esters) have been introduced into the eye and demonstrated favorable properties for sustained release ocular drug delivery (see Einmahl, S., 2002, Invest. Ophthalmol. Vis. Sci. 43(5)). Polylactide particles have been used to target an agent to the retina and RPE following intravitreal injection of a suspension of such particles (Bourges et al., 2003, Invest. Ophthalmol. Vis. Sci. 44(8)). A macroscopic implantable device suitable for introduction into the posterior or anterior segment of the eye is referred to herein as an ocular implant (see Jaffe, G., 2000, Invest. Ophthalmol. Hs. Sci., 41(11)). Therefore, provided herein is an ocular implant comprising a Cp40 analog, e.g., in a therapeutically effective amount to deliver the Cp40 analog to the individual with a disease or condition treatable by complement inhibition. Such devices may be macroscopic implants comprising the Cp40 analog or may be comprised of a plurality of nanoparticles or microparticles impregnated with or encapsulating the agent. In one embodiment, the ocular implant is any ocular implant known in the art. Exemplary implants and methods for manufacture thereof are described, e.g., in US 2009/0220572 A1. Other implants known in the art can also be used.

Other embodiments include gel-forming compositions comprising a soluble collagen that are useful for the delivery of compstatin or compstatin analogs to the posterior segment of the eye. The collagen is initially soluble and forms a solution that has a low viscosity but is capable of rapid formation of a gel under appropriate conditions, e.g., conditions encountered upon administration to a mammalian subject. The invention therefore provides a system for delivery of the pharmaceutically active agents to the posterior segment of the eye. The system is designed to localize such molecules in sufficient concentration to provide sustained delivery while at the same time allowing the macromolecule to be released in sufficient amounts. In addition, the collagen gel may protect the compstatin or compstatin analogs from degradation, e.g., by endogenous proteases.

The composition forms a gel following introduction into the body, e.g., upon contact with a physiological fluid. The composition can also form a gel upon contact with a fluid such as phosphate buffered saline, or other fluid containing appropriate ions. Thus the composition can be injected at an appropriate location, e.g., in close proximity to the posterior segment of the eye, where it forms a gel. Alternately, a preshaped gel implant can be made, e.g., by introducing the solution into a mold or cavity of the desired shape and allowing gel formation to occur in the presence of a suitable concentration of a salt. The salt can be added either prior to or following the introduction of the solution into the mold or cavity. The mold or cavity can be, e.g., any structure that contains a hollow space or concave depression into which a solution can be introduced. In another embodiment, a film or membrane is formed from the collagen solution containing a therapeutic agent.

Release of the agent from the gel can occur by any mechanism, e.g., by diffusion of the agent out of the gel, as a result of breakdown of the gel, or both. One aspect of the invention is the selection of suitable concentrations of soluble collagen and collagen solids that result in a gel that retains the agent within the gel so as to provide sustained delivery for a desired period of time while also permitting release of the agent from the gel in sufficient concentration to be effective at its site of action in the posterior segment of the eye.

In accordance with certain embodiments of the invention, a solution containing the soluble collagen and compstatin or a compstatin analog is prepared by combining the soluble collagen and the compstatin or compstatin analog in solution using any suitable method, e.g., by adding the compstatin or compstatin analog to a solution containing soluble collagen. The composition is delivered locally to an appropriate location in or near the eye of a mammalian subject, typically to an area outside of and in close proximity to the posterior segment of the eye. The solution rapidly forms a gel at or close to of the site of administration. The compstatin or compstatin analog is entrapped within the gel and then diffuses out of the gel or is released as the gel degrades over time, thereby providing a continuous supply of the compstatin or compstatin analog to tissues and structures that are either in direct physical contact with the gel or located nearby or delivering into the blood stream. In certain embodiments the solution is administered behind the sclera of the eye, as discussed further below. Delivery can be accomplished by injection (e.g., using a 30 gauge needle or the like), by catheter, etc., as further described below.

A variety of different collagen preparations can be used in the present invention provided that the collagen is initially soluble and is capable of rapidly forming a gel under appropriate conditions. Suitable collagen preparations, and methods for their manufacture, are described, e.g., in U.S. Pat. Nos. 5,492,135; 5,861,486; 6,197,934; 6,204,365; and WO 00/47130, but the invention is not limited to such preparations or methods. These collagens are prepared in soluble form and rapidly form a gel upon exposure to physiological fluids or other fluids having suitable concentration of ions. In accordance with the present invention, injecting or otherwise introducing the collagen solution to the eye or near the eye results in gel formation, presumably induced by contact with physiological fluids. However it is noted that the invention is in no way limited by the mechanism by which gel formation occurs. In addition, as noted above, the gel can be formed in vitro and them implanted at an appropriate location, e.g., in close proximity to the posterior segment of the eye.

One suitable method of preparing a soluble collagen solution involves extracting collagen from a natural source, acid solubilizing the collagen, and dialyzing the solubilized collagen against a solution containing a chelating agent, e.g., a metal chelating agent such as ethylenediamine tetraacetic acid, disodium salt dihydrate (EDTA), while raising the pH. One or more dialysis steps against a solution such as deionized water lacking the chelating agent may also be performed. Unlike standard collagen solutions that undergo spontaneous fibrillogenesis at neutral pH and room temperature, collagen solutions for use in the present invention remain in solution during storage for extended periods of time and rapidly undergo gel formation when exposed to physiological fluids. While not wishing to be bound by any theory, the chelating agent may alter the concentration of one or more cations and thereby prevent fibrillogenesis that would otherwise occur as the pH is raised. The chelating agent may have other desirable effects on the collagen solution, and in certain embodiments of the invention the collagen solution comprises a chelating agent, e.g., EDTA. The chelating agent may remain in the collagen solution following dialysis or may be added to the collagen solution. The concentration of the chelating agent may range, for example, between about 0.02M and about 0.05M, e.g., between about 0.025M and about 0.035M. Other chelating agents may also be used including, but not limited to, those described in U.S. Pat. No. 5,861,486.

In certain embodiments the collagen solution has a concentration of soluble collagen ranging between 1 mg/ml and 100 mg/ml, e.g., between 10 mg/ml and 70 mg/ml, between 20 mg/ml and 50 mg/ml, e.g., 30 mg/ml, etc. In certain embodiments of the invention the pH of the collagen solution is between 6.0 and 8.0, e.g., between 6.5 and 7.5, e.g., 7.0.

In certain embodiments of the invention the collagen composition further comprises a fibrillar component comprising fibrillar collagen solids. For example, certain collagen compositions contain between 0.5 mg/ml and 30 mg/ml fibrillar collagen solids, or between 1 mg/ml and 20 mg/ml fibrillar collagen solids, e.g., 2 mg/ml, 3 mg/ml, 4 mg/ml, 5 mg/ml, 6 mg/ml, 8 mg/ml, 10 mg/ml, etc. In terms of percent fibrillar collagen solids on a weight/volume basis, certain collagen compositions contain between 0.05 and 3% fibrillar collagen solids or between 0.1 and 2% fibrillar collagen solids, e.g., 0.2%, 0.3%, 0.4%, 0.5%, 0.6%, 0.8%, 1%, 1.2%, etc. Any suitable fibrillar component can be used in the collagen compositions of the invention. Fibrillar collagen solids can be prepared using a variety of methods. For example, fibrillar collagen may be reconstituted collagen prepared from animal sources such as bovine hide (Frontiers in Matrix Biology, Vol. 10, pp. 1-58, in Methods of Connective Tissue Research, Eds. Robert, Moczar, and Moczar, S. Karger, Basel, 1985). Fibrillar collagen may be prepared from human or animal sources as described in U.S. Pat. Nos. 4,969,912 and 5,322,802. The fibrillar collagen solids are suspended in solution at a concentration typically ranging from about 10-100 mg/ml. The collagen suspension containing fibrillar collagen solids is combined with, e.g., added to, a soluble collagen composition either prior to or following addition of the therapeutic agent to a solution comprising soluble collagen.

In some embodiments of the invention the soluble collagen preparation comprises a chemical cross-linking agent. The agent may crosslink collagen molecules and/or fibrils to one another and/or may crosslink a therapeutic agent such as compstatin or an analog thereof to a collagen molecule or fibril. Typical cross-linking agents crosslink collagen amine groups to one another or to amine, carboxyl, phenol, sulfonyl, or carbohydrate groups of therapeutic agents. Suitable cross-linking agents include, but are not limited to, those described in WO 00/47130. Without wishing to be bound by any theory, cross-linking may stabilize the collagen gel (e.g., decrease its rate of breakdown) and/or decrease the rate of release of the therapeutic agent from the gel.

Without wishing to be bound by any theory, the presence of fibrillar collagen solids may have any of a variety of advantageous effects. By way of non-limiting example, the fibrillar collagen solids may increase the in vivo stability of the collagen gel, e.g., they may decrease the rate of breakdown of the gel. The fibrillar collagen solids may increase the stability of a therapeutic agent contained in the gel and/or decrease or modulate the rate at which the agent is released from the gel by diffusion and/or breakdown of the gel.

The collagen preparations preferably form a gel within 5 minutes (300 seconds) following contact with physiological fluids. More preferably the collagen preparations form a gel within 90 seconds, 2 minutes (120 seconds) or within 3 minutes (180 seconds) following contact with physiological fluids. Preparations that form a gel within shorter time periods, e.g., within 5-90 seconds, or longer time periods, e.g., 3-5 minutes, can also be used.

Any of collagen types I-XXVIII, or mixtures thereof, can be used in the present invention. The collagen can be purified from natural sources (e.g., human tissue or animal tissue such as bovine, rabbit, etc.) as described in the above-referenced patents and publications. Alternatively, the collagen can be manufactured using recombinant DNA techniques, in which case the sequence can be of human or animal origin. See, e.g., U.S. Pat. Nos. 5,593,854 and 5,667,839. Methods for the production of proteins, e.g., a polypeptide of interest such as a collagen chain, using recombinant DNA technology are well known in the art. Suitable methods include those described above. The term "collagen" includes collagen fragments. Thus in certain embodiments the soluble collagen comprises or consists of a collagen fragment or combination of fragments. In certain embodiments a complete collagen polypeptide chain is used.

While collagen preparations such as those described above are particularly preferred in certain embodiments of the invention, a variety of other gel-forming materials could also be used in a gel-forming composition of the invention. In certain embodiments the gel is a hydrogel, by which is meant a gel that contains a substantial amount of water. Preferably the material and the gel that it forms are biocompatible. In certain embodiments the material and the gel that it forms are biodegradable. A variety of modified or derivatized collagens are also of use in various embodiments of the invention. See, e.g., U.S. Pat. No. 5,201,764. For example, collagen can be acylated with one or more acylating agents such as glutaric anhydride, succinic anhydride, and maleic anhydride and at least one other acylating agent selected from the group consisting of methacrylic anhydride, beta-styrene sulfonyl chloride, ethylene-maleic anhydride copolymer, styrene-maleic anhydride copolymer or poly(vinyl) sulfonic acid.

Other gel-forming materials include, but are not limited to, hyaluronic acid and modified forms thereof, polysaccharides such as alginate and modified forms thereof, self-assembling peptides, etc. See, e.g., U.S. Pat. No. 6,129,761 for further description of alginate and modified forms thereof, hyaluronic acid and modified forms thereof, and additional examples of soluble gel-forming materials that are of use in various embodiments of the present invention. As described therein, other polymeric hydrogel precursors include polyethylene oxide-polypropylene glycol block copolymers such as Pluronics™ or Tetronics™ which are crosslinked by hydrogen bonding and/or by a temperature change, as described in Steinleitner et al., Obstetrics & Gynecology, 77:48-52 (1991); and Steinleitner et al., Fertility and Sterility, 57:305-308 (1992). Other materials which may be utilized include proteins such as fibrin or gelatin. Polymer mixtures also may be utilized. For example, a mixture of polyethylene oxide and polyacrylic acid which gels by hydrogen bonding upon mixing may be utilized.

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically crosslinked may be utilized, as disclosed in Matsuda et al., ASAID Trans., 38:154-157 (1992).

In general, the polymers are at least partially soluble in aqueous solutions, such as water, buffered salt solutions, or aqueous alcohol solutions. Methods for the synthesis of the other polymers described above are known to those skilled in the art. See, for example Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available. Naturally occurring and synthetic polymers may be modified using chemical reactions available in the art and described, for example, in March, "Advanced Organic Chemistry," 4th Edition, 1992, Wiley-Interscience Publication, New York.

Water soluble polymers with charged side groups may be crosslinked by reacting the polymer with an aqueous solution containing ions of the opposite charge, either cations if the polymer has acidic side groups or anions if the polymer has basic side groups. Examples of cations for crosslinking of the polymers with acidic side groups to form a hydrogel are monovalent cations such as sodium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin. In some embodiments a self-assembling peptide, such as those described in U.S. Pat. No. 6,800,481 is used. These peptides self-assemble to form a hydrogel structure upon contact with monovalent cations, e.g., such as those present in extracellular fluid.

In embodiments of the invention in which the gel is formed by cross-linking polymer chains to one another, the composition can include an appropriate cross-linking agent, which is selected according to the particular polymer. Alternately, the cross-linking agent can be administered after administration of the composition containing the gel-forming material, at substantially the same location. Any of these gels can be formed in vitro, e.g., as described above for gels comprising soluble collagen, and implanted at an appropriate location in or in the vicinity of the eye.

In certain embodiments, the implants described herein comprise between about 100 g and about 50 mg of a Cp40 analog, e.g., between about 100 g and about 40 mg between about 100 g and about 30 mg between about 100 g and about 20 mg between about 100 g and about 10 mg between about 100 g and about 9 mg e.g., between about 100 g and about 8 mg, e.g., between about 100 g and about 7 mg, e.g., between about 100 g and about 6 mg, e.g., between about 100 g and about 5 mg, e.g., between about 100 g and about 4 mg, e.g., between about 100 g and about 3 mg, e.g., between about 100 g and about 2 mg, e.g., between about 100 g and about 1 mg, e.g., between about 100 g and about 500 g.

Methods for making microparticles and nanoparticles are known in the art. Generally, a microparticle will have a diameter of 500 microns or less, e.g., between 50 and 500 microns, between 20 and 50 microns, between 1 and 20 microns, between 1 and 10 microns, and a nanoparticle will have a diameter of less than 1 micron. Preferably the device is implanted into the space occupied by the vitreous humor. The ocular implant may comprise a polymeric matrix. The invention also provides periocular implants, which are macroscopic implantable devices suitable for introduction in the vicinity of the eye, e.g., in close proximity to the eye. In certain embodiments the periocular implant is made of similar materials to those described above.

In other embodiments, cells that express a Cp40 analog can be implanted into the eye. U.S. Pat. No. 6,436,427 provides a method for delivering biologically active molecules to the eye by implanting biocompatible capsules containing a cellular source of the biologically active molecule.

In some embodiments, controlled release forms may be prepared to achieve a sustained, or location-specific liberation of the compstatin analog in the digestive tract in order to improve absorption and prevent certain forms of metabolism. For example, acid-resistant coatings of tablet or acid-resistant capsule materials may be used to prevent a release of compstatin analogs in the stomach and protect the compound from metabolism by gastric enzymes. Suitable materials and coatings to achieve controlled release after passage of the stomach are primarily composed of fatty acids, waxes, shellac, plastics and plant fibers and include, but are not limited to, methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate, sodium alginate or stearic acid. Sustained release in the gastrointestinal tract can for example be achieved by embedding compstatin analogs in a matrix of insoluble substances such as various acrylics, chitin and others. Methods to prepare such formulations are known to those skilled in the art.

Compstatin may be formulated into suppositories or clysters for rectal, vaginal or urethral administration. For this purpose, compstatin analogs can be dissolved or suspended in a greasy base carrier such as cocoa butter that is solid or semi-solid at room temperature but melts at body temperature or in a water-soluble solid base such as polyethylene glycol or glycerin (made from glycerol and gelatin). Other excipients may be added to improve the formulation, and suppositories will be shaped in a form that facilitates administration. In other embodiments, liquid suppositories consisting of compstatin analogs dissolved or suspended in a liquid carrier suitable for rectal delivery to be applied with a small syringe may be used.

For the treatment of chronic or acute lung conditions in which complement activation is implicated, a preferred route of administration of a pharmaceutical composition is pulmonary administration. Accordingly, a pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, including replacement pulmonary surfactant, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intraarticular, intravitreal, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution can be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, in microbubbles for ultrasound-released delivery or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents including replacement pulmonary surfactants; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa.

Methods:

Another aspect of the invention features methods of regulating complement activation. In general, the methods comprise contacting a medium in which regulation of complement activation is desired with a compstatin analog of the present invention, wherein the contacting results in regulation of complement activation in the medium. The medium can be any medium in which regulation of complement activation is desired. In certain embodiments, the medium includes cells or tissues of an organism, including (1) cultured cells or tissues, (2) cells or tissues within the body of a subject or patient, and (3) cells or tissues that have been removed from the body of one subject and will be replaced into the body of the same patient (e.g., extracorporeal shunting of blood or autologous transplantation) or transferred to another patient. In connection with the latter embodiment, the medium may further comprise a biomaterial, such as tubing, filters or membranes that contact the cells or tissues during extracorporeal shunting. Alternatively, the medium may comprise biomaterials that are implanted into a subject.

In certain embodiments, the methods of regulating complement activation apply to living patients or subjects and comprise part or all of a method of treating the patient for a pathological condition associated with complement activation, particularly AP-mediated complement activation, which can amplify complement effector responses and exacerbate inflammatory damage in tissues and cells, irrespective of the triggering mechanism of complement activation. Many such pathological conditions are known in the art (see, e.g., Holers, 2008, supra) and include, but are not limited to, atypical hemolytic uremic syndrome (aHUS); dense deposit disease (DDD); C3 glomerulonephritis (C3GN); C3 glomerulopathies; other complement-mediated nephropathies and glomerular inflammatory diseases; age-related macular degeneration (AMD); any eye disorder characterized by macular degeneration, choroidal neovascularization (CNV); retinal Neovascularization (RNV), proliferative vitreoretinopathy, glaucoma, uveitis, ocular inflammation, or any combination of these; paroxysmal nocturnal hemoglobinuria (PNH); cold agglutinin disease (CAD); warm antibody autoimmune hemolytic anemias (wAIHAs); sickle cell disease; transplant-associated thrombotic microangiopathies; rheumatoid arthritis (RA), systemic lupus erythematosus (SLE); several autoimmune and autoinflammatory kidney diseases; autoimmune myocarditis; multiple sclerosis; traumatic brain and spinal cord injury; cerebral, intestinal and renal ischemia-reperfusion (IR) injury; spontaneous and recurrent pregnancy loss; antiphospholipid syndrome (APS); Parkinson's disease; Alzheimer's disease; other neurodegenerative inflammatory conditions underpinned by aberrant synaptic remodeling, excessive microglial activity and cognitive decline; asthma; anti-nuclear cytoplasmic antigen-associated pauci-immune vasculitis (Wegener's syndrome); non-lupus autoimmune skin diseases such as pemphigus, bullous pemphigoid, and epidermolysis bullosa; post-traumatic shock, cancer; periodontitis; gingivitis; and atherosclerosis. In particular embodiments, the pathological condition has been associated with mutations and polymorphisms in the gene encoding FH and/or CD46, including but not limited to: AMD, aHUS and membrano-proliferative glomerulonephritis type II (MPGN-II, also referred to as dense deposit disease (DDD)). In other embodiments, the compstatin analogs of the present invention are suitable for use as a substitute for Eculizumab in treatment of diseases for which those agents are currently prescribed, or for which they are being developed in pre-clinical and clinical studies. Those diseases include, but are not limited to, aHUS, PNH, C3G (DDD/C3GN), CAD and AMD.

The treatment methods typically comprise (1) identifying a subject with a disease or condition treatable by regulation of complement activation as described hereinabove, (2) measuring a parameter of the disease or condition treatable by regulation of complement activation using art-standard techniques well within the purview of the skilled artisan (e.g., biopsy, histology, MRI, bone-scan, X-Ray, pain tolerance, posture, and the like), (3) administering to the subject an effective amount of a compstatin analog of the invention using a treatment regimen and duration appropriate for the condition being treated, and (4) measuring the parameter of the disease or condition as an indication that the disease or condition has been ameliorated or has been treated. Delivery of the compstatin or compstatin analog may be performed by any suitable route of administration known in the art, including orally, nasal (e.g., via nasal spray), intraocular (including intravitreal), rectal, intravenous injection/infusion, subcutaneous injection/infusion, intramuscular, periodontal (e.g., gingival administration or intrapapillary infiltration), topical and the like. Development of appropriate dosages and treatment regimens will vary depending upon any number of factors, including but not limited to, the type of patient and type of disease state being treated, the age of the patient and the route of administration. The skilled artisan is familiar with the design of dosage regimens that take such variables into account. For instance, it will be apparent to the skilled artisan that oral administration of a compstatin analog of the invention will require a higher initial dosage, due to the lesser bioavailability from that route as compared with, e.g., intravenous injection. Likewise, intramuscular administration of a compstatin analog of the invention would require a higher dose than delivery of the same analog via intravenous or intravitreal injection. Suitable therapeutically effective doses are described in more detail elsewhere herein.

In one embodiment, a method for treating an individual, such as a human patient or non-human primate, with a disease or condition treatable by regulation of complement activation is provided that includes the steps of first identifying an individual with the disease or condition treatable by regulation of complement activation and then administering to the individual a therapeutically effective amount of a Cp40-based analog of the invention, wherein the route of administration is intravenous or subcutaneous, and wherein the therapeutically effective amount of the Cp40-based analog is between about 0.125 mg/kg to about 10 mg/kg; preferably, the amount is between about 0.25 mg/kg and about 5 mg/kg, or between about 0.5 mg/kg and about 5 mg/kg, or between about 0.5 mg/kg and about 4 mg/kg, or between about 0.5 mg/kg and about 3 mg/kg, or about 3 mg/kg. In another embodiment, the route of administration is intramuscular, and the therapeutically effective amount of the Cp40-based analog is between about 0.25 mg/kg to about 50 mg/kg; preferably, the amount is between about 0.25 mg/kg and about 35 mg/kg, or between about 0.25 mg/kg and about 30 mg/kg, or between about 0.25 mg/kg and about 10 mg/kg, or between about 0.25 mg/kg and about 5 mg/kg, or about 2.5 mg/kg. In some aspects, the route of administration is orally, and the therapeutically effective amount of the Cp40-based analog is between about 1 mg/kg to about 20 mg/kg; preferably, the amount is between about 1 mg/kg and about 10 mg/kg or between about 1 mg/kg and about 5 mg/kg. In another embodiment, the route of administration is intravitreal, and the therapeutically effective amount of the Cp40-based analog is between about 1 g to about 10 mg; preferably, the amount is between about 1 g and about 2,000 g or about 1 mg. Other suitable therapeutically effective doses and routes of administration are described in more detail elsewhere herein. In these embodiments, the method also includes one or more measuring steps that includes measuring at least one parameter of the disease or condition treatable by regulation of complement activation using art-standard techniques well within the purview of the skilled artisan (e.g., biopsy, histology, MRI, bone-scan, X-Ray, pain tolerance, posture, and the like), whereby measuring the parameter of the disease or condition may be used as an indication that the disease or condition has been treated, it being understood that the measuring step can be performed before, during, and/or after administering the Cp40-based analog.

In another embodiment, a method for treating an individual with a disease or condition treatable by regulation of complement activation is provided that includes administering to the individual an initial therapeutically effective amount of a Cp40-based analog of the invention, wherein the route of administration is intravenous or subcutaneous, and wherein the initial therapeutically effective amount of the Cp40-based analog is at least about 0.125 mg/kg to about 10 mg/kg; preferably, the amount is between about 0.5 mg/kg to about 3 mg/kg. This treatment is then followed by administering to the individual a maintenance dose of a Cp40-based analog of the invention, wherein the route of administration is intramuscular, and wherein the maintenance dose of the Cp40-based analog is at between about 0.25 mg/kg and about 50 mg/kg; preferably, it is between about 0.25 mg/kg and about 10 mg/kg. Alternatively, the maintenance dose is administered orally, and the maintenance does of the Cp40-based analog is between about 1 mg/kg and about 20 mg/kg; preferably, it is between about 1 mg/kg and about 10 mg/kg. Other routes of administering the maintenance dose are also described elsewhere herein. The maintenance dose is then administered via multiple deliveries given once every 2-3 days to about once every 1 month; preferably, once every 2 weeks. Alternatively, the initial therapeutically effective dose is at least about 2 mg/kg administered via an intramuscular route. In these embodiments, the method also includes one or more measuring steps that includes measuring at least one parameter of the disease or condition treatable by regulation of complement activation using art-standard techniques well within the purview of the skilled artisan (e.g., biopsy, histology, MRI, bone-scan, X-Ray, pain tolerance, posture, and the like), whereby measuring the parameter of the disease or condition may be used as an indication that the disease or condition has been treated, it being understood that the measuring step can be performed before, during, and/or after administering the Cp40-based analog.

Also provided herein are novel methods of generating antibodies against compstatin analogs. The method typically includes immunization of a suitable animal for generating antibodies, such as a rat, mouse, monkey, rabbit, goat, pig, or sheep. In a preferred embodiment, a rabbit is immunized with a compstatin analog; preferably, the compstatin analog is Cp40 or a Cp40-based analog (e.g., Cp40-KK or Cp40-KKK). In such aspects, the compstatin analog is conjugated with a suitable carrier protein, such as keyhole limpet hemocyanin (KLH), prior to immunization. In other embodiments, the compstatin analog is conjugated to the carrier protein in a mixture further comprising an adjuvant; preferably, it is a strong adjuvant. Typical adjuvants includes inorganic compounds (e.g., alum, aluminum hydroxide, aluminum phosphate, calcium phosphate hydroxide), mineral oil, detergents, plant saponins, cytokines (e.g., IL-1, IL-2, IL-12), block copolymers, and combinations thereof. For instance, in one particular embodiment, a rabbit is immunized with Cp40 or a Cp40-based analog conjugated to KLH in the presence of a strong adjuvant. The immunization dose ranges from about 50 g to about 500 g; preferably, the dose is about 100 g. The immunized animal is then administered the analog-KLH-adjuvant composition via injection every 2 days to every 4 weeks; preferably, the animal is injected weekly. The injections are continued for at least 2 weeks, e.g., 2 weeks, 3 weeks, 4 weeks, 5 weeks, or more. In a preferred embodiment, the immunized animal is given 4 weeks injections of the analog-KLH-adjuvant composition for 5 weeks. The injections comprise dose ranges from 10 g to about 100 g; preferably, the dose is about 50 g. The Cp40-specific antibodies are then purified from the animal serum by any suitable protein purification technique known in the art, e.g., affinity chromatography. The Cp40 and Cp40-Lysine antibodies produced by the method described herein are highly specific for the Cp40 or Cp40-Lysine peptide as described in further detail in Example 7 below. Thus, these novel antibodies cannot only specifically detect the different compstatin analogs, but can further discriminate between the unmodified and lysine-modified versions thereof. In a preferred embodiment, the novel antibodies are monoclonal antibodies.

Also provided herein are novel and sensitive methods for the detection of the Cp40-based analogs described herein, in biological fluids including those from which scanty samples of minimal volume can only be retrieved, such as the vitreous. Such methods require only very small quantities of biological fluid. These methods employ SPR analysis performed on vitreous samples or plasma samples containing the Cp40-based analogs of interest. In one embodiment, a method of detecting a Cp40-based analog in a biological sample is provided that includes the steps of (1) providing a biological sample that contains Cp40-based analog molecules, where at least a portion of these analogs are bound to C3/C3b/C3c; (2) providing a CM5 sensor chip to which a plurality of Cp40 or Cp40 analog molecules are covalently attached; (3) heat-inactivating the biological sample to release the compstatin analogs from the target molecules (i.e., C3/C3b/C3c); (4) mixing the heat-inactivated sample with a pre-determined amount of C3 of human plasma as a source of C3; (5) contacting the mixture of the heat-inactivated sample with a fixed amount of C3 or of human plasma to the CM5 sensor chip, whereby the Cp40 analog molecules released from the target-bound Cp40 complexes in the biological sample, will compete with the Cp40 molecules/analogs immobilized on the CM5 sensor chip for binding to C3 or plasma-derived C3; and (6) detecting the free C3 by binding to Cp40 or its analogs immobilized on the CM5 sensor chip. The SPR signal is directly proportional to the amount of C3 bound to the immobilized Cp40 molecules or its analogs. An SPR signal reduction therefore corresponds to the reduction of binding of free C3 to the immobilized Cp40 and serves as a measure of the amount of free Cp40 or Cp40 analogs present in the heat-inactivated biological sample. Quantification of the unknown Cp40 analog amount in the sample is performed according to a standard curve of known peptide concentrations. In a preferred embodiment, the Cp40 molecules that are covalently attached to the CM5 sensor chip are the same Cp40-based analog molecules of interest in the biological sample. For instance, in a particular embodiment, Cp40-KKK is covalently attached to the CM5 sensor chip and the biological sample (e.g., a vitreous sample) is first heat-inactivated, as described above, and subsequently mixed with a calibrated source of C3 and flowed over the chip to allow the competitive detection of peptide released from C3/C3b/C3c-bound Cp40-KKK complexes in the sample.

The following examples are provided to describe the invention in greater detail. They are intended to illustrate, no to limit, the invention.

Example 1. Design of Analogs Based on Cp40

Cp40 (DTyr-Ile-[Cys-Val-Trp(Me)-Gln-Asn-Trp-Sar-Ala-His-Arg-Cys]-mIle-NH$_2$) (SEQ ID NO:7), Cp40-Lys-NH$_2$ (Cp40-K; SEQ ID NO: 8), Cp40-Lys-Lys-NH$_2$ (Cp40-KK; SEQ ID NO: 9), and Cp40-Lys-Lys-Lys-NH$_2$ (Cp40-KKK; SEQ ID NO: 10) were synthesized in house or by GL Biochem (Shanghai, China) using Fmoc-solid phase peptide synthesis and purified using reversed-phase high-performance liquid chromatography (RP-HPLC) based on techniques known in the art (see, e.g., Qu, H. et al., 2011, Mol Immunol 48:481-489; Qu, H. et al., 2013, Immunobiology 218:496-505). As illustrated in FIG. 2, the purity of the compounds was verified by RP-HPLC and matrix-assisted laser desorption ionization-time-of-flight mass spectrometry (MALDI-TOF MS) on a Micromass® MALDI micro MX™ (Waters Corporation, Milford, Mass.). Depending on the amount of compound, an XBridge BEH C18 column (5-μm particle size, 150-mm length, Waters Corporation, Milford, Mass.) with either a diameter of 4.6, 10, or 19 mm was used for RP-HPLC, and elution was achieved with a gradient of 5-70% acetonitrile in 0.1% aqueous TFA solution within 30 min at a flow rate of 2, 4.5, or 16 ml/min, respectively.

The synthesis of mPEG(3k)-, mPEG(2k)-, mPEG(1k)-, and mPEG(1056)-Cp40 was carried out based on PEGylation procedures known in the art (U.S. Pat. No. 8,962,553; Risitano et al., 2014, Blood 123:2094-2101). In brief, 1 eq of Cp40 (5 mg/ml) was dissolved in acetonitrile/water (1:1), and 2 eq of the respective activated mPEG ester were added. The pH of the reaction mixture was adjusted to 8 using N-methylmorpholine. After stirring for 0.5-1 h at room temperature, the reaction mixture was quenched upon addition of 0.1% aqueous TFA (pH 2). All peptides were purified by RP-HPLC as described above and characterized by MALDI-TOF MS (see FIG. 2).

For the preparation of mPEG(528)-Cp40, linear Cp40 was synthesized on resin as described previously (see, e.g., Qu, H. et al., 2011, Mol Immunol 48:481-489; Qu, H. et al., 2013, Immunobiology 218:496-505). After Fmoc-deprotection of the final N-terminal amino acid Fmoc-DTyr(tBu)-OH by use of 20% piperidine in DMF, 3 eq of mPEG(528)-NHS ester in DMF were added to the dried beads. The pH was adjusted to 8.0 using N-methylmorpholine, and agitation was allowed to proceed for 2 h on a rotator. Reaction completion was confirmed by Kaiser test. The beads were subsequently washed with DMF and DCM and dried under vacuum. The peptide was cleaved from resin as described by Qu et al. (supra). The lyophilized crude linear deprotected peptide (1 eq) was dissolved in 80% aqueous methanol, and 20 mM iodine (13 eq) in methanol was slowly added with vigorous stirring. After 30 min of stirring at room temperature, the cyclization reaction was quenched by the addition of 20 mM aqueous ascorbic acid. Methanol was removed under reduced pressure and the crude peptide was purified by RP-HPLC as described above. The peptide was then characterized by MALDI-TOF MS (see FIG. 2).

All peptides were initially obtained as a TFA salt and further converted into an acetate salt on the HPLC column using 25 mM aqueous ammonium acetate as described in EP 2163558 A3. The mass of the final compounds was confirmed by MALDI-TOF MS. Peptides used for in vivo experiments were tested for the presence of endotoxin (<0.03 EU/ml). Cp40, Cp40-K, Cp40-KK, and Cp40-KKK were synthesized by GL Biochem (Shanghai, China) using Fmoc-solid phase peptide synthesis and purified using reversed-phase high-performance liquid chromatography (RP-HPLC) based on a procedure described previously by Qu et al. The purity of the compounds was verified by RP-HPLC and MALDI-TOF MS (FIG. 2) on a Micromass® MALDI micro MX™ (Waters Corporation, Milford, Mass.). Depending on the amount of compound, an XBridge BEH C18 column (5-μm particle size, 150-mm length, Waters Corporation, Milford, Mass.) with either a diameter of 4.6, 10, or 19 mm was used for RP-HPLC, and elution was achieved with a gradient of 5-70% acetonitrile in 0.1% aqueous TFA solution within 30 min at a flow rate of 2, 4.5, or 16 ml/min, respectively.

Example 2. Solubility of Cp40-Based Analogs

To test the solubility of the Cp40-based analogs designed in Example 1, for each analog, 5-10 mg of the peptide was weighed in a LoBind Eppendorf tube and mixed with 20 μl of PBS (pH 7.4). The mixture was vortexed and centrifuged for 2 min at 16,873×g. Unless otherwise noted, if the respective peptide was not dissolved, PBS was added in portions of 10 μl, followed by vortexing and centrifugation, until all precipitate disappeared. The pH of the peptide solutions was determined on indicator paper (Whatman™ 2614-991, Type CF, wide-range pH test strips with colorimetric chart, pH range 4.5-10, size 6×80 mm). The concentrations of the final solutions were determined based on the absorbance measured on a NanoDrop™ 2000c spectrophotometer (Thermo Scientific, Wilmington, Del.) at 280 nm using the equation $c=A/\varepsilon \cdot b$ (c=concentration, A=absorbance, ε=extinction coefficient, b=path length).

While Cp40 is highly solubility in water, it is less soluble at physiological pH (0.8 mg/ml in PBS at pH 7.4) (Qu et al., 2013, Immunobiology 218:496-505). Therefore, to create a Cp40 with improved solubility without significantly decreasing the inhibitory activity or binding affinity for C3, Cp40 was modified at either its N-terminal region or its C-terminal region as described in Example 1.

Figure 3:
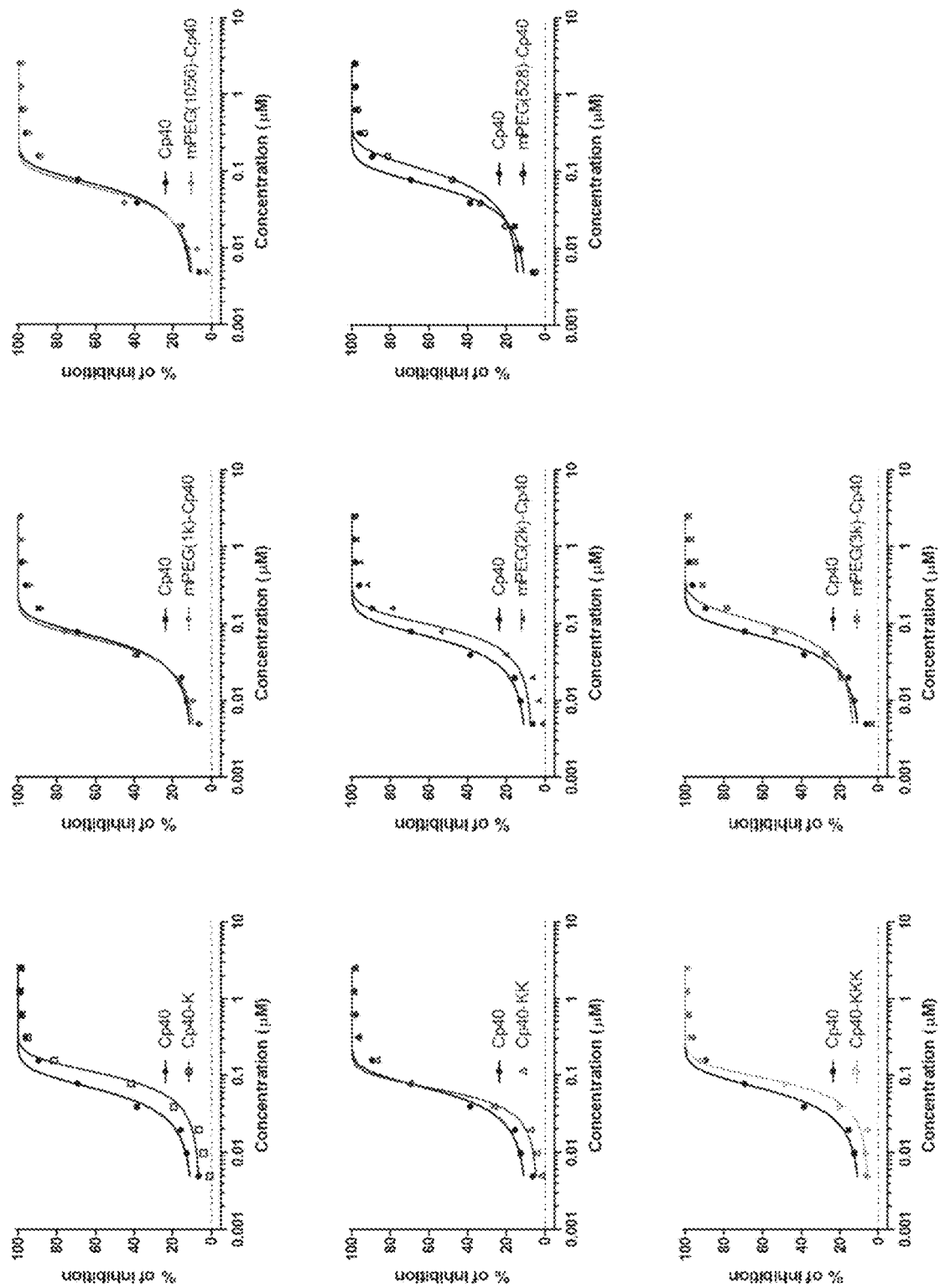
FIG. 3 illustrates classical pathway complement inhibition by exemplary compstatin analogs as measured by ELISA, with Cp40 in each graph being shown for comparison. The y-axis represents the percent inhibition of complement activity, and the x-axis is the concentration of the peptide.

Previous reports indicated that Cp40 modified with a 40 kDa PEG chain at its C-terminus was associated with a drop in inhibitory activity, whereas the Cp40 modified with a 40 kDa PEG chain at its N-terminus exhibited an extended residence time in plasma after in vivo administration in NHP, but had greater than 100-fold lower binding affinity as compared to unmodified Cp40 (Risitano et al., 2014, Blood 123:2094-2101; see FIGS. 2 and 3). In the present study, the N-terminus of the Cp40 was coupled to polydisperse PEG chains of 1, 2, or 3 kDa via amide coupling. The resulting analogs were termed mPEG(3k)-Cp40, mPEG(2k)-Cp40, and mPEG(1k)-Cp40 (FIG. 1). PEGylation greatly increased the solubility of the resulting Cp40-based analogs, with mPEG(3k)-Cp40 showing the highest solubility in PBS, 270 mg/ml (pH=7.0, Table 2).

Compounds PEGylated with polydisperse polymers have a less-defined structure making them more difficult to characterize (Veronese, 2001, Biomaterials 22:405-417). To create a better defined-structure that can be better characterized, PEGylation of Cp40 using monodisperse polymers were carried out using the activated NHS esters of mPEG(1056) and mPEG(528). Whereas PEGylation using polydisperse PEGs and mPEG(1056) was performed with pre-synthesized Cp40, PEGylation of the monodisperse compound mPEG(528)-Cp40 was carried out on-resin, eliminating one additional step of HPLC purification. The solubility properties of the resulting monodisperse analog mPEG(1056)-Cp40 were found to be very similar to those of its polydisperse counterpart. In contrast, attachment of a smaller PEG chain (528 Da) resulted in a significant drop in the solubility, from about 140 to 2.3 mg/ml in PBS (Table 2).

In addition to PEGylation, incorporation of hydrophilic/charged residues was used as an alternative approach to increase the solubility of Cp40. To this end, one, two, or three lysine residues were attached to the C-terminus of Cp40 during the peptide synthesis. Notably, compound solubility increased with an increasing number of Lys residues, i.e., the solubility of Cp40-K (37 mg/ml) was much less than that of Cp40-KK and Cp40-KKK (>245 mg/ml) (Table 2). Notably, whereas a pH of 7-7.5 was measured in solutions of 277 mg/ml Cp40-KK in PBS, the presence of the third Lys residue led to a higher pH in the respective Cp40-KKK solutions. A pH in the 7 range was observed only with a Cp40-KKK concentration of 7 mg/ml (Table 2).

TABLE 2

Solubility and pH of the Cp40-based analogs in PBS.

| Analog | Conc. (mg/ml) | pH |
|---|---|---|
| Cp40 | 1.08 | 7.5 |
| mPEG(3k)-Cp40 | >270 | 7 |
| mPEG(2k)-Cp40 | 172 | 7.5 |
| mPEG(1k)-Cp40 | 157 | 7-7.5 |
| mPEG(1056)-Cp40 | 137 | 7-7.5 |
| mPEG(528)-Cp40 | 2.3 | 7-7.5 |
| Cp40-K | 7.1 | 7.5 |
| Cp40-KK | >272 | 7-7.5 |
| Cp40-KKK | >245 | 8.5 |
| Cp40-KKK | 7.0 | 7.5* |
| Cp40-KKK | <100** | 9.5 |

*pH adjusted upon addition of PBS.
**after additional lyophilization from $H_2O$.

Example 3. Complement Inhibitory Potency and Target Affinity of Cp40-Based Analogs To determine whether the modified peptides retained Cp40's inhibitory activity and target affinity, inhibition of the classical pathway of complement activity was evaluated in an in vitro enzyme-linked immunosorbent assay (ELISA) (see, for example, Mallik, 2005, Journal of Medicinal Chemistry 48:274-286). In brief, antigen-antibody complex-mediated complement activation in normal human plasma in the presence or absence of Cp40 and its analogs was detected based on C3b deposition. For this purpose, microtiter wells (NUNC) were coated with 50 μl of 1% ovalbumin in PBS (pH 7.4) at ambient temperature for 2 h. The wells were blocked with 200 μl of 1% BSA in PBS for 1 h, then coated with 50 μl of 1:1000 α-ovalbumin polyclonal antibody in PBS for 1 h. Between each step, the plate was washed thrice with 200 μl of 0.05% Tween 20 in PBS (PBS-T); 30 μl of VBS (Veronal buffer 1×; 5 mM veronal, pH 7.4, containing 150 mM NaCl, 0.5 mM $CaCl_2$) and 0.5 mM $MgCl_2$) were placed in all but the first well of each row of the 96-well plate, and 5 μM peptide solutions in VBS were prepared. Peptide concentrations were determined on a Nanodrop™ 2000c spectrophotometer from Thermo Scientific at 280 nm using an extinction coefficient of 12,615·$M^{-1}$ $cm^{-1}$ for all peptides. Human plasma diluted 1:40 in VBS was incubated for 15 min with peptide of 0.005 to 2.5 μM. After washing with PBS-T, 50 μl/well of 1:1000 goat α-human C3 HRP conjugated antibody in 1% BSA in PBS was added to the wells and incubated for 1 h at room temperature. Complement fixation indicating activation was detected by the addition of HRP substrate (0.05% ABTS and 0.1% of 30% aqueous $H_2O_2$ in 0.1 M sodium citrate, pH 4.2) and read at 405 nm. The absorbance data obtained at 405 nm were translated into % inhibition, considering 100% to be equal to complement activation in the absence of peptide. The percent inhibition was plotted against the logarithm of concentrations, and the resulting data set was fitted to the equation "log(inhibitor) vs. normalized response" using GraphPad Prism 5 (La Jolla, Calif.). $IC_{50}$ values were obtained from the fitted parameters of the mean of at least three independent experiments. Cp40 was always used as the internal control.

The binding affinities and kinetic profiles of the Cp40-based analogs with C3b were assessed by SPR using a Biacore 3000 instrument (GE Healthcare, Piscataway Township, N.J.) based on previously described protocols (see, e.g., Qu et al., 2011, *Mol Immunol* 48:481-489; Qu et al., 2013, *Immunobiology* 218:496-505; Magotti et al., 2009, *J Mol Recognit* 22:495-505; Huang et al., 2014, *Chem Med Chem* 9:2223-2226). All experiments were carried out at 25° C. using 0.01 M HEPES, pH 7.4, with 0.15 M NaCl, 3 mM EDTA, and 0.005% surfactant P20 (HBS-EP) as the running buffer. Purified human C3b (Complement Technology, Inc., Tyler, Tex.) was coated onto a CM5 sensor chip (GE Healthcare, Uppsala, Sweden) at densities of 11,000-20,000 resonance units (RUs) via amide coupling, as adapted from the immobilization procedure provided with the Amine Coupling Kit from GE Healthcare. A non-coated flow cell was used as a reference surface. A series of five samples of increasing concentrations of each Cp40 (2.5, 5, 10, 20, 40 nM) analog were successively injected for 2 min each at a flow rate of 30 µl/min, with a final dissociation step of 80 min. Cp40 was included in every SPR experiment as an internal control. Each peptide was screened in at least three independent experiments. All sensorgrams were processed using Scrubber software (BioLogic Software, Campbell, Australia). The resulting data were globally fitted to a 1:1 Langmuir binding model in BIAevaluation software (GE Healthcare) to obtain the equilibrium dissociation constant ($K_D$) from the equation $K_D=k_d/k_a$.

Figure 4:
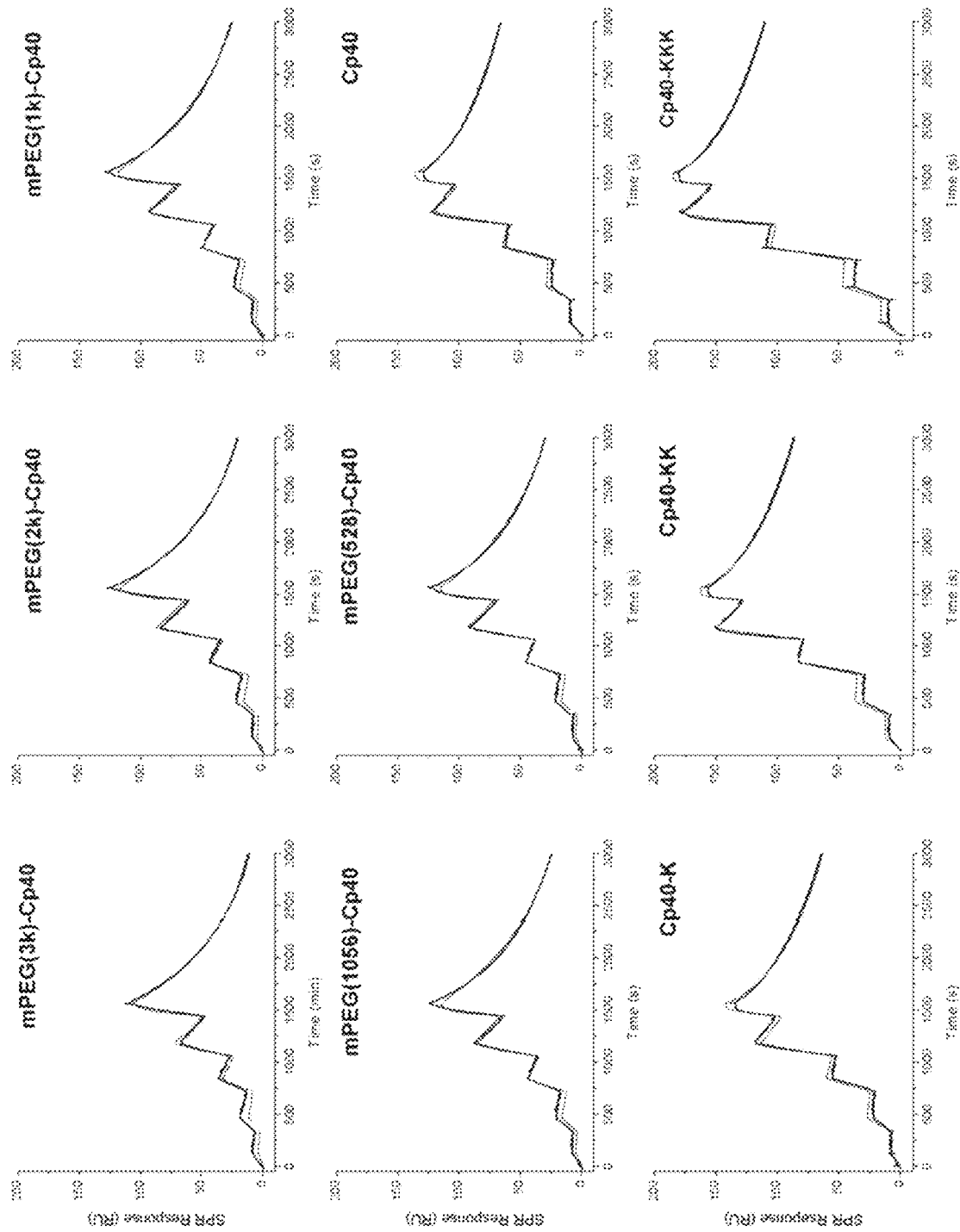
FIG. 4 is a kinetic analysis of Cp40 as compared to Cp40 modified at the N-terminus or C-terminus. Each SPR sensorgram is the result of the analysis of a representative example out of at least three SPR experiments of a single-cycle kinetic titration of an individual peptide over five concentrations (black: processed SPR data; gray: kinetic fit to 1:1 Langmuir model).
Figure 5:
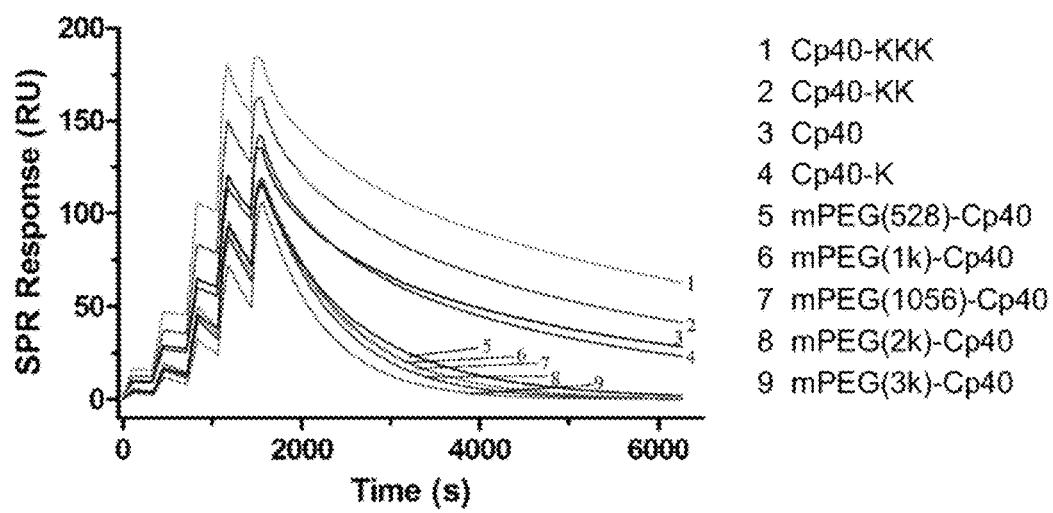
FIG. 5 profiles of the binding of exemplary Cp40-based analogs to C3b, as assessed by SPR experiments after fitting to a 1:1 Langmuir binding model.

As shown in Table 3 and FIG. 3, the inhibitory activity of the modified Cp40 peptide was not significantly influenced by PEGylation at the N-terminus or the addition of Lys residues at the C-terminus. In contrast, the binding affinity of the individual peptides to C3b was affected by the Cp40 modifications (Table 3). Whereas the addition of the shortest PEG chain to the N-terminus of Cp40 (mPEG(528)-Cp40) resulted in a 5-fold drop in the binding affinity toward C3b, increasing the length of the PEG chain further decreased the affinity of mPEG(3k)-Cp40 ($K_D$ 7.9 nM) as compared to that of Cp40 ($K_D$ 0.5 nM) (Table 3 and FIGS. 4 and 5). On the other hand, attachment of Lys residues had a positive effect on the binding of the resulting analogs to C3b. Whereas the addition of a single Lys residue did not affect the binding significantly, addition of two or three Lys residues resulted in a 1.25- and 2.5-fold increase in the binding affinity to C3b, respectively (Table 3 and FIGS. 4 and 5). In general, the variation in the association rate ($(0.7-4)\times10^6 M^{-1} s^{-1}$) of the various analogs was higher than that of the dissociation rate ($(1.2-2.8)\times10^{-3} s^{-1}$).

TABLE 3

Inhibitory activity and C3b binding affinity of Cp40-based analogs.*

| Analog | $IC_{50}$ (nM) | $k_a$ ($10^6 M^{-1} s^{-1}$) | $k_d$ ($10^{-3} s^{-1}$) | $K_D$ (nM) |
|---|---|---|---|---|
| Cp40 | 56.8 ± 3.0 | 3.57 ± 0.70 | 1.84 ± 0.40 | 0.53 ± 0.14 |
| mPEG(3k)-Cp40 | 83.0 ± 7.0 | 0.45 ± 0.27 | 2.40 ± 0.91 | 7.91 ± 2.02 |
| mPEG(2k)-Cp40 | 83.8 ± 4.5 | 0.54 ± 0.13 | 2.39 ± 0.46 | 4.47 ± 0.61 |
| mPEG(1k)-Cp40 | 52.7 ± 2.9 | 0.76 ± 0.15 | 2.18 ± 0.14 | 2.98 ± 0.54 |
| mPEG(1056)-Cp40 | 52.0 ± 2.7 | 0.72 ± 0.25 | 2.80 ± 0.95 | 3.93 ± 0.39 |
| mPEG(528)-Cp40 | 83.5 ± 8.1 | 1.00 ± 0.27 | 2.45 ± 0.28 | 2.58 ± 0.51 |
| Cp40-K | 95.6 ± 9.2 | 1.98 ± 0.20 | 1.85 ± 0.50 | 0.92 ± 0.20 |
| Cp40-KK | 61.8 ± 4.2 | 3.94 ± 1.26 | 1.52 ± 0.25 | 0.44 ± 0.17 |
| Cp40-KKK | 81.7 ± 5.3 | 3.83 ± 2.58 | 1.24 ± 0.42 | 0.21 ± 0.09 |

$k_a$, association constant
$k_d$, dissociation constant
$K_D$, equilibrium dissociation constant
*All values were calculated from the man of at least three independent experiments.

Example 4. Pharmacokinetic Analysis of Cp40-Based Analogs in Plasma of Non-Human Primates after Subcutaneous Administration Methods.

Cp40, mPEG(3k)-Cp40, Cp40-KK, and Cp40-KKK were tested in vivo in NHPs to assess the influence of PEGylation and Lys conjugation on their pharmacokinetic profiles. The studies were performed at the Simian Conservation Breeding and Research Center (SICONBREC), Inc. (Makati, Philippines). Each peptide analog (Cp40, Cp40-KK, Cp40-KKK, mPEG(3k)-Cp40) was tested in two individual 6- to 7-year-old, healthy male cynomolgus monkeys (*Macaca fascicularis*), with a body weight of about 4 kg. Each peptide was administered at 2 mg/kg in a single subcutaneous injection: 8 mg of net Cp40 were dissolved in 2 ml of sterile saline (Cp40, Cp40-KK), 0.5 ml of sterile saline (mPEG (3k)-Cp40), or 0.25 ml of 100 mM phosphate buffer (Cp40-KKK) and injected subcutaneously using a 3/10-mL insulin safety syringe with 29GX1/2" needle. Blood samples were collected before (0 h) and at various time points after the sample administration (t=5 min, 30 min, 1, 2, 4, 6, 12, 24, 48, 72, 96, 120 h) into EDTA-vacutainer blood collecting tubes to prevent coagulation and complement activation. All blood samples were centrifuged at ~800×g for 10 min, and the resulting plasma samples were immediately frozen and shipped to the University of Pennsylvania for further analysis. All NHP studies were performed in accordance with animal welfare laws and regulations.

To analyze the plasma samples and determine the plasma half-life, preparation of standard solutions and plasma samples was first performed. Calibration curves were prepared together with the plasma samples being analyzed: Stock solutions of the respective peptide (Cp40, Cp40-KK, Cp40-KKK, or mPEG(3k)-Cp40) were spiked into untreated NHP plasma at final concentrations of 1, 2, 4, 8, and 16 µM. The concentrations of the stock solutions were determined using a Nanodrop™ 2000c spectrophotometer from Thermo Scientific at 280 nm. Prior to further analysis, all plasma samples were treated with methanol for protein precipitation as follows: 500 of the NHP plasma to be analyzed was mixed in a 0.5 ml LoBind Eppendorf tube with 150 µl methanol containing 0.5 µg/ml isotope-labeled Cp40 (DTyr-Ile-[Cys-Val-Trp(Me)-Gln-Asn-Trp-Sar-Ala-His-[13C6; 15N4]Arg-Cys]-mIle-NH$_2$, Bachem, Torrance, Calif.), which served as internal standard (IS). The mixture was vortexed for ~8 min, allowed to sit at room temperature for 10 min and centrifuged for 20 min at 16,873×g. The supernatant was mixed 1:1 with a solution of 20% methanol in 10 mM aqueous ammonium formate (pH 3) in an injection vial (TruView LCMS Certified Clear Glass 12×32 mm Screw Neck Total Recovery Vial, Waters Corporation, Milford, Mass.). For mPEG(3k)-Cp40 samples, 3% aqueous MeCN was used instead of the ammonium formate solution.

For liquid chromatography and mass spectrometry, plasma samples were processed as described above and analyzed by ultra-performance liquid chromatography-electrospray ionization-tandem mass spectrometry (UPLC-ESI-MS) based on the procedures described in the art (see Qu et al., 2013, *Immunobiology* 218:496-505; Primikyri et al., 2017, *J Chromatogr B Analyt Technol Biomed Life Sci* 1041-1042:19-26). The method was slightly adjusted for the analysis of plasma samples containing mPEG(3k)-Cp40. Here, a fixed collision energy of 35 V was applied in the ion trap. For the preparation of standard curves, the areas under the curve (AUCs) of the respective MS peaks (triple-charged Cp40 and isotope-labeled Cp40, quadruple-charged Cp40-K (fragment), Cp40-KK and Cp40-KKK, and the monocharged fragment at 436.256 m/z of mPEG(3k)-Cp40 (-Sar-Ala-His-Arg-)) were determined by integration and plotted against the concentration. The plasma concentration at each time point was calculated from the extracted peak area of the same mass peaks of each peptide using the corresponding standard curve.

To determine the plasma half-life and additional pharmacokinetic parameters, the half-life of the peptides in NHP plasma was determined as described in Qu et al. (supra) and Primikyri et al. (supra). The maximum concentration ($c_{max}$) and time of maximum concentration observed ($t_{max}$) were determined manually from the pharmacokinetic profiles. The AUC from 0-120 h ($AUC_{0-t}$), AUC from 0-infinite time ($AUC_{0-\infty}$), the apparent volume of distribution Vz/F, (F=bioavailability), and the apparent clearance CL/F were calculated using the following equations:

$$AUC_{0-t_n} = \int_0^{t_n} c \cdot t \, dt, \quad AUC_{0-\infty} = AUC_{0-t} + AUC_{t-\infty},$$

$$\frac{Vz}{F} = \frac{CL}{k_{el}}, \quad \frac{CL}{F} = \frac{DOSE}{AUC_{0-\infty}},$$

with $t_n$=120 h, $k_{el}$=the elimination rate constant. Individual pharmacokinetic parameters were calculated using a non-compartmental approach with Phoenix 64 WinNonlin Build 8.0.0.3176 software. The plasma model (extravascular dosing) was used with linear trapezoidal linear interpolation.

Immunonephelometry was carried out to determine the levels of complement component C3 in NHP plasma, using the N antisera to Human Complement Factors (C3c) assay kit (Dade Behring, Marburg, Germany). In order to validate the assay for C3 quantification in NHP plasma, C3 concentrations were first measured in human and then in NHP plasma to determine the differing degrees of reactivity of the antibodies in the kit. For this purpose, serial dilutions of NHP plasma were spiked with known concentrations of purified C3 from cynomolgus monkeys. The C3 concentrations determined in human and NHP plasma were correlated, and a correction factor (CF) of 1.2 was obtained for the C3 concentration in NHP plasma. The C3 concentrations in NHP plasma $c_{C3}$* were measured by nephelometry and corrected to the final concentrations using the equation $c_{C3}=c_{C3}\cdot CF$. C3 baseline levels and C3 levels during the course of the experiments were assessed using the described assay.

For the assessment of proteolysis of Cp40-KK and Cp40-KKK in NHP and human plasma and in NHP total protein skin tissue, Cp40-KK or Cp40-KKK was spiked into either NHP or human plasma at a final concentration of 16 μM. Cp40-KKK was also spiked into NHP skin total protein (from cynomolgus monkeys; Zyagen, San Diego, Calif.) to a final concentration of 20 μM. The samples were incubated for 24 h at 37° C. in a water bath and samples were taken before and at various time points during and at the end of the incubation. The samples were subjected to protein precipitation as described above and analyzed by UPLC-ESI MS as described above.

Results.

Each peptide was injected subcutaneously (sc) in a single dose (8 mg; 2 mg/kg) into two monkeys, and blood samples were collected over a period of 5 days (t=pre-injection, 5, 30 min, 1, 2, 4, 6, 12, 24, 48, 72, 96, 120 h after injection, FIG. 6A). As shown in FIG. 3B and Table 4, the half-life of Cp40 was 41 h and 48 h for the two monkeys. In comparison, the pharmacokinetic profiles of mPEG(3k)-Cp40 administered as a single-dose sc injection to two cynomolgus monkeys showed that a higher maximum concentration of mPEG(3k)-Cp40 was reached, and the half-life was extended ($t_{1/2}$ 65 h and 53 h, respectively) (FIG. 6C and Table 4).

TABLE 4

Pharmacokinetic parameters calculated from the pharmacokinetic profiles of Cp40, Cp40-KK, Cp40-KKK, and mPEG(3k)-Cp40 in NHP plasma after s.c. administration.

| Analog | Animal | $c_{injection}$ (mg/ml) | $t_{1/2}$ (h) | $t_{max}$ (h) | $C_{max}$ (μM) | $AUC_{0-t}$ (μM · h) | $AUC_{inf}$ (μM · h) | Vz/F (ml/kg) | CL/F ((mg/kg)/ μM · h) |
|---|---|---|---|---|---|---|---|---|---|
| Cp40 | 1 | 4* | 40.9 | 2 | 6.20 | 233 | 263 | 448946 | 7605 |
|  | 2 |  | 48.1 | 2 | 5.53 | 218 | 255 | 545665 | 7856 |
| Cp40-KK (SUM) | 1 | 4* | 145 | 1 | 12.90 | 329 | 597 | 700664 | 3348 |
|  | 2 |  | 276 | 1 | 9.26 | 257 | 755 | 1055443 | 2648 |
| Cp40-KKK (SUM) | 1 | 32** | 46.7 | 6 | 11.90 | 658 | 805 | 167382 | 2483 |
|  | 2 |  | 41.8 | 2 | 15.10 | 573 | 685 | 176010 | 2921 |
| mPEG(3k)-Cp40 | 1 | 16* | 64.8 | 6 | 11.10 | 654 | 922 | 202917 | 2169 |
|  | 2 |  | 53.7 | 2 | 8.99 | 529 | 656 | 236127 | 3050 |

Abbreviations: $t_{1/2}$, half-life; $t_{max}$, time of maximum concentration observed; $C_{max}$, maximum concentration; AUC, area under the curve; Vz/F, apparent volume of distribution (F = bioavailability); and CL/F, apparent clearance.
*dissolved in saline
**dissolved in 100 mM phosphate buffer.

In addition, when mPEG(3k)-Cp40 was administered the level of C3 was saturated for a longer period of time (33-35 h, vs. 4-5 h for Cp40). A single s.c. injection of mPEG(3k)-Cp40 in cynomolgus monkeys resulted in a pharmacokinetic profile comparable to that obtained for administration of the parental compound Cp40, with a $t_{max}$ at 2 to 6 h post-injection (see FIG. 6B, C). Despite the similar pharmacokinetic curve, mPEG(3k)-Cp40 reached a $C_{max}$ of about 10 µM, almost 2-fold higher than that of the parental peptide (FIG. 6C and Table 4). Furthermore, the AUC0-120 h (~592 µM h) was higher, the $t_{1/2}$ (~59 h) was longer, and the CL/F (~2610 mL h-1 kg-1) was slower than the respective values obtained for Cp40 (see Table 4). In addition, the target protein C3 was saturated for a longer period of time (~34 h vs ~4.5 h for Cp40) (FIG. 6B, C, dotted lines).

Figure 6:
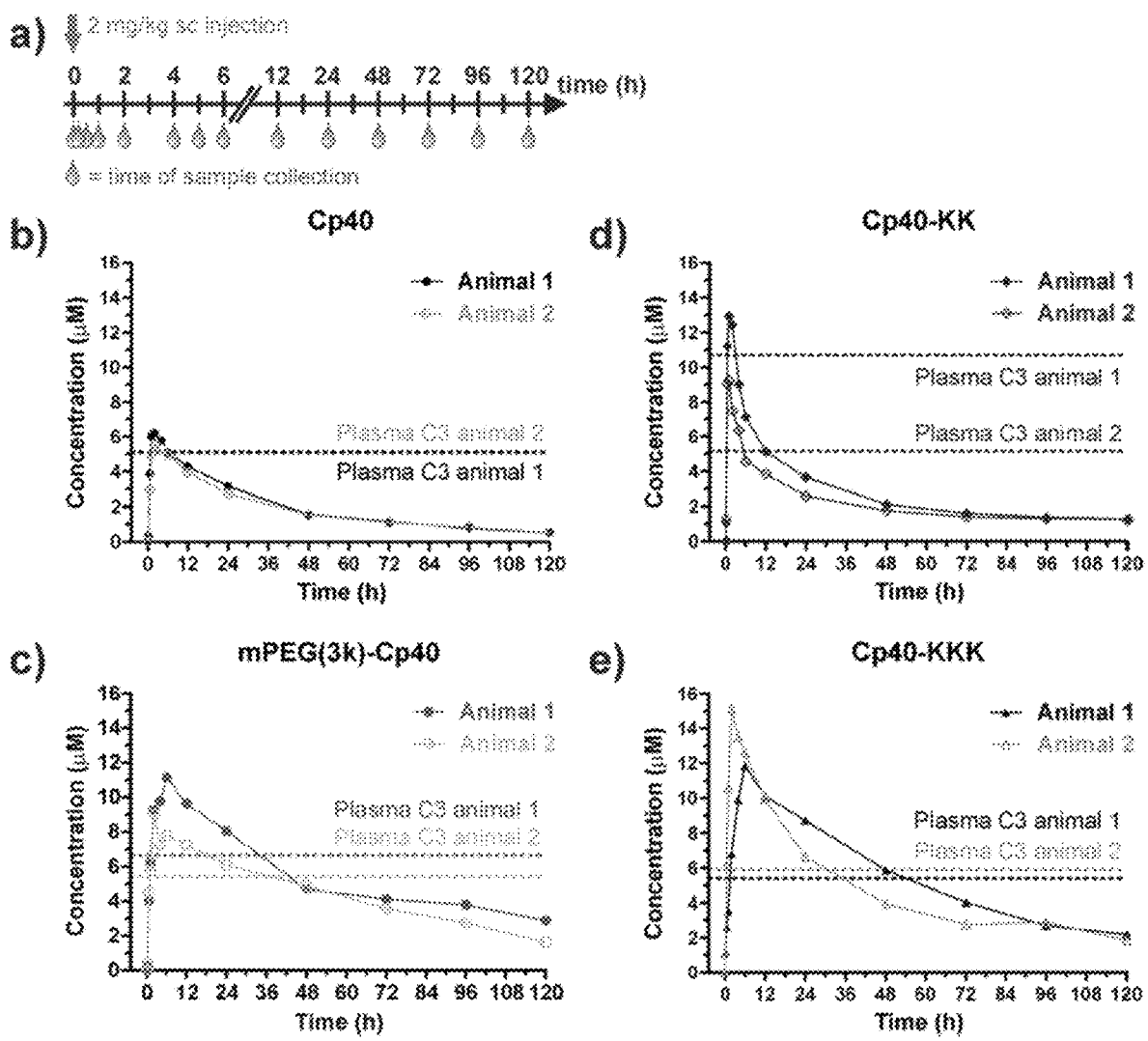
FIG. 6 is a pharmacokinetic evaluation of Cp40 and exemplary modified Cp40 peptides in NHP. Panel a) depicts a scheme of the single-dose peptide administration via s.c. injection into two cynomolgus monkeys at time zero (vertical arrow). Cp40 or a modified Cp40 was injected into each animal (2 mg/kg; 8 mg net) and blood samples were collected at various time points (drops). Panel b) is a pharmacokinetic profile of Cp40. Panel c) is a pharmacokinetic profile of mPEG(3k)-Cp40. Panel d) is a pharmacokinetic profile of Cp40-KK. Panel e) is a pharmacokinetic profile of Cp40-KKK as assessed by UPLC-ESI-MS analysis of the NHP plasma samples. C3 levels in each animal are shown in corresponding colors as dotted lines.

FIG. 6D shows the pharmacokinetic profiles of Cp40-KK over time in the plasma of two cynomolgus monkeys injected sc with the compound. Cp40-KK reached its maximum concentration in the plasma of both animals faster ($t_{max}$=1 h) than did Cp40 ($t_{max}$=2 h), and a higher concentration was achieved; however, the plasma concentration of Cp40-KK also decreased faster than did that of Cp40 (FIGS. 6A and D and Table 4). Whereas Cp40 remained above the plasma level of C3 for 4-5 h, the plasma concentration of Cp40-KK was reduced to a level lower than that of C3 after 2.5-5 h. In general, the peptide concentration seemed to depend on the C3 concentration. The overall clearance of Cp40-KK was very slow, with a half-life of 145 h in one monkey and 276 h in the other. In addition to Cp40-KK, Cp40-K was also detected in the NHP plasma samples, beginning at 30 min after sc injection of Cp40-KK, indicating enzymatic cleavage of the terminal Lys residue of the peptide. However, the level of Cp40-K remained almost unchanged over time (FIGS. 7A and B). Since Cp40-K resulted from Lys cleavage of Cp40-KK, the sum of the concentrations of both conjugates are shown in FIG. 6.

Cp40-KKK was administered to two cynomolgus monkeys via a single-dose sc injection. Instead of saline, phosphate buffer was used to lower the pH of the Cp40-KKK solution to bring the pH into physiological range. The single s.c. injection of Cp40-KKK resulted in a pharmacokinetic profile comparable to that of Cp40 and mPEG(3k)-Cp40. For instance, the Cp40-KKK peptide reached a $C_{max}$ of about 13.5 µM at 2 to 6 h post-injection (FIG. 6E and Table 4), with an AUC0-120 h of ~616 µM h, CL/F of ~2700 mL h-1 kg-1, and $t_{1/2}$ of ~44.3 h. In addition, after the administration of Cp40-KKK, plasma levels of C3 remained saturated for about 40 h, which was about 7-fold longer than the saturation period observed with unmodified Cp40 (FIG. 6E). These data indicate that the Cp40 derivatives mPEG (3k)-Cp40 and Cp40-KKK have an improved pharmacokinetic profile after a s.c. injection when compared with the parental Cp40 compound.

Quantification in NHP plasma proved to be more tedious for Cp40-KKK than for the other peptide analogs. UPLC-ESI-MS analysis revealed a suspiciously low Cp40-KKK concentration in plasma, with values not exceeding 2 µM at any time point in both animals (FIGS. 7C and D). Superimposition of the BPI chromatograms of the NHP plasma samples showed increasing peaks at the retention times for Cp40-KK ($t_R$=4.35 min) and Cp40-K ($t_R$=4.65 min) over time after injection of Cp40-KKK; the peak of the compound itself ($t_R$=4.10 min) was small from the beginning Examples of these chromatograms are shown in FIG. 8. The intensity of the internal standard, isotopically labeled Cp40, which appeared at the same retention time as Cp40 ($t_R$=4.92 min), remained unchanged, indicating that one or two Lys residues are cleaved from Cp40-KKK in NHP plasma, but not the third. Therefore, the concentrations of Cp40-KKK, Cp40-KK, Cp40-K, and Cp40 was determined in all the plasma samples from both animals.

Figure 7:
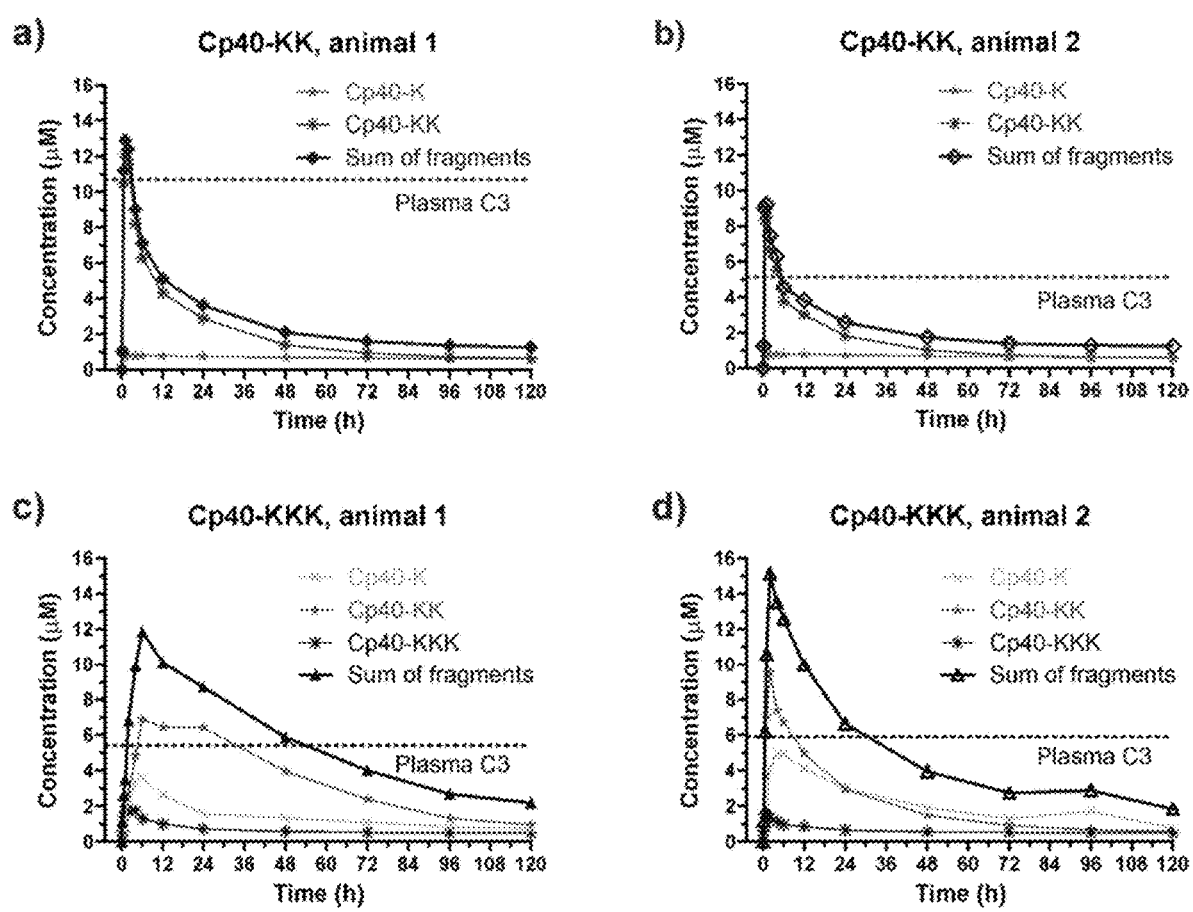
FIG. 7, panels a) and b) show the quantification of Cp40-KK in the plasma samples of two cynomolgus monkeys, as determined by UPLC-ESI-MS.
Figure 8:
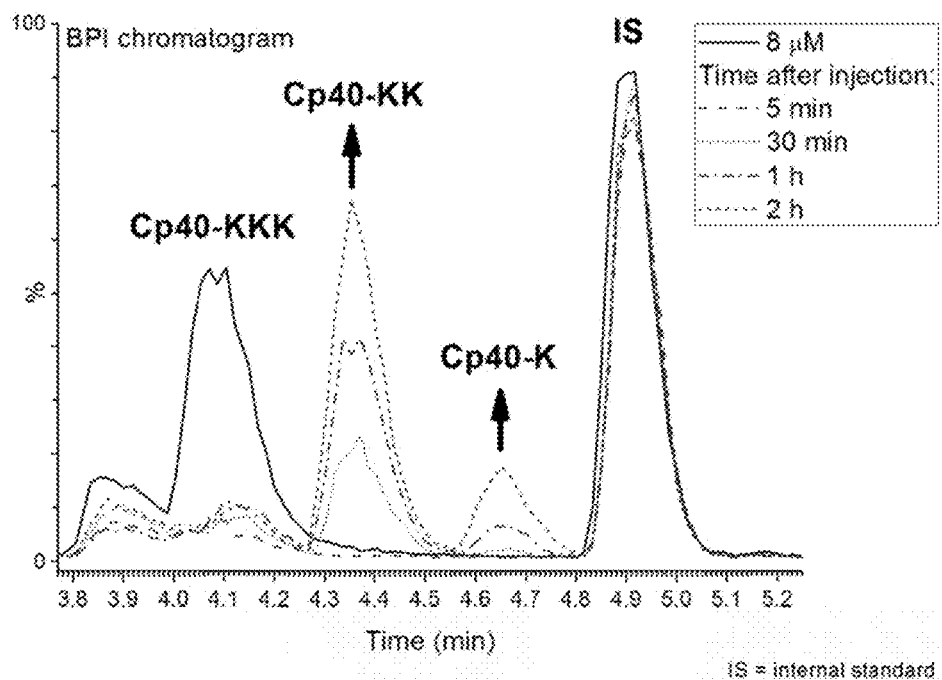
FIG. 8 is an excerpt of the superimposed base peak intensity (BPI) chromatograms of Cp40-KKK spiked into non-human primate (NHP) plasma at a concentration of 8 (solid line) and that of four plasma samples collected at 5 min (long dashed line), 30 min (dotted line), 1 h (dashed and dotted line), and 2 h (short dashed line) after single-dose s.c. injection of 2 mg/kg Cp40-KKK into NHP.

As shown in FIGS. 7C and D, no Cp40 was detected in any of the plasma samples. The lowest concentration was found for Cp40-KKK, indicating that most of the compound is immediately cleaved in plasma to form Cp40-KK, although Cp40-KKK could still be detected over the entire period of study. In contrast to the plasma samples from monkeys receiving Cp40-KK, a larger amount of Cp40-KK was further cleaved to Cp40-K; in one monkey, as much as 5 µM Cp40-K was detectable 4 h after the injection of Cp40-KKK (FIG. 7D). The amount of Cp40-K, Cp40-KK, and Cp40-KKK was summed to assess the overall concentration of peptide in NHP plasma at each time point (FIG. 6E and FIG. 7). The half-life of Cp40-KKK (42 h and 47 h for the two monkeys) was comparable to that of Cp40 (Table 4). Nevertheless, the maximum concentration of Cp40-KKK was higher and was reached at a later time than for Cp40, at least in one animal. In addition, the level of Cp40-KKK remained above the C3 concentration six to nine times longer as did that of Cp40.

Figure 9:
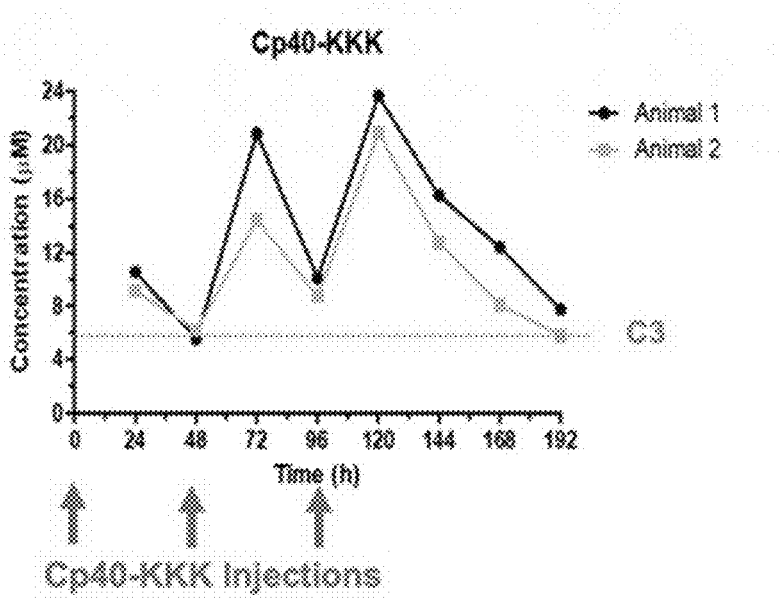
FIG. 9 is a graph of the plasma concentration of Cp40-KKK in cynomolgus monkeys following three 2 mg/kg intravenous injections every 48 hours. The x-axis represents peptide concentration (M) in NHP plasma as determined by mass spectrometry, and the y-axis represents time after injection (hours). The dotted line represents the average levels of plasma C3.
Figure 10:
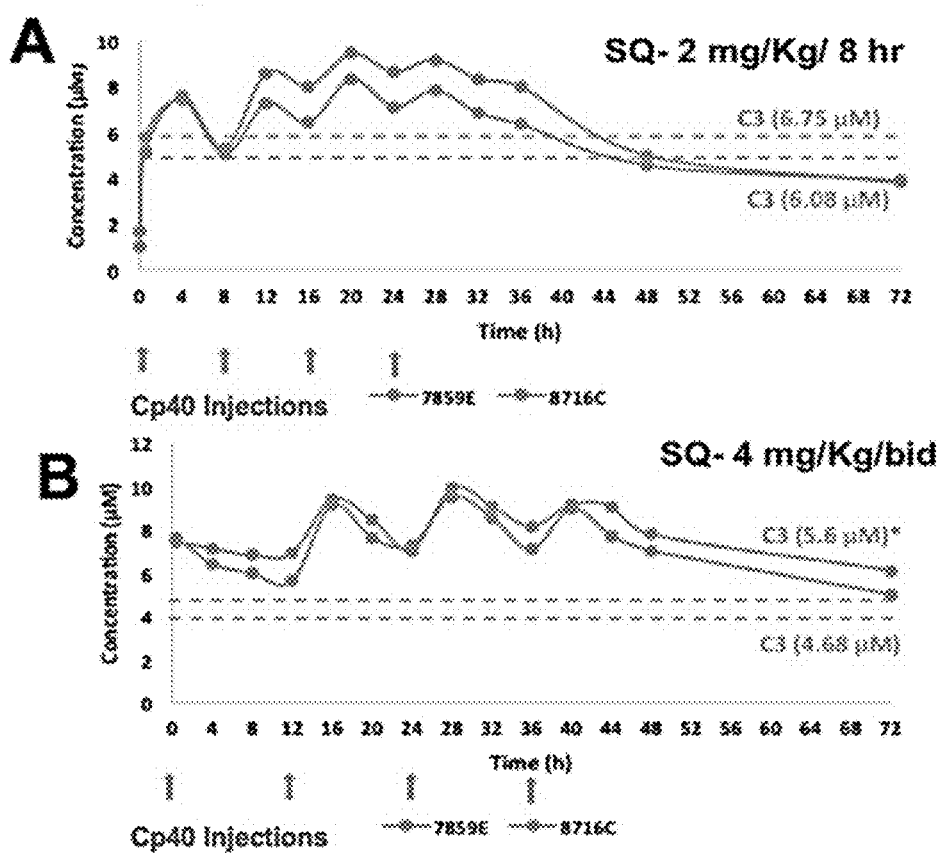
FIG. 10 is a graph of the NHP plasma concentration of Cp40 in cynomolgus monkeys following four subcutaneous injections of 2 mg/kg Cp40 administered at 0, 8, 16, and 24 hours (panel a) or 4 mg/kg Cp40 administered at 0, 12, 24, and 36 hours (panel b). The x-axis represents peptide concentration (M) in NHP plasma, and the y-axis represents time after injection (hours). The dotted lines represent the average levels of plasma C3.

The cleavage of Cp40-KKK could also be observed after multiple s.c. injections in cynomolgus monkeys (FIG. 9). Most interestingly, accumulation of the levels of Lysine-containing derivatives was observed over time (FIG. 9). Such an "accumulation" phenomenon is intrinsic of the Cp40-KKK analog, as it was not previously observed after multiple s.c. injections of the parental Cp40 compound (FIG. 10). Of note, the observed $C_{max}$ of Cp40 after multiple s.c. injections did not exceed 8-10 µM even when the compound was dosed in cynomolgus monkeys as frequently as every 8-12 hrs (FIG. 10). Conversely, the observed $C_{max}$ of an identical dose of Cp40-KKK, after multiple s.c. dosing, was markedly higher, reaching or even exceeding 20 µM. In addition, the plasma bioavailability of the Cp40-KKK analog was markedly higher even though the compound was dosed through the s.c. route at less frequent intervals than Cp40 (i.e., every 48 hrs), which indicates that the unique structure of Cp40-KKK may confer new and beneficial pharmacokinetic properties to this compound that contribute to its prolonged residence, increased bioavailability, and sustained inhibitory activity.

Example 5. Pharmacokinetic Properties of Cp40-Based Analogs after Intravenous Administration In vivo pharmacokinetic studies were conducted, in which cynomolgus monkeys were administered single i.v. injections of mPEG(1k)-Cp40, mPEG(3k)-Cp40, Cp40-KK, or Cp40-KKK. The pharmacokinetic profiles of the Cp40 analogs are summarized in Table 5 and FIG. 11.

TABLE 5

Pharmacokinetic profiles of Cp40 analogs following i.v. injection.

| PK parameters | Cp40-analogs | | | |
|---|---|---|---|---|
| | PEG(1k)-Cp40 | PEG(3k)-Cp40 | Cp40-KK | Cp40-KKK |
| $t_{1/2}$ (h) | 53.2 | 84.37 | 49.23 | 35.31 |
| AUC 0-120 (µmol/L*h) | 304.4 | 313.59 | 85.39 | 312 |

Figure 11:
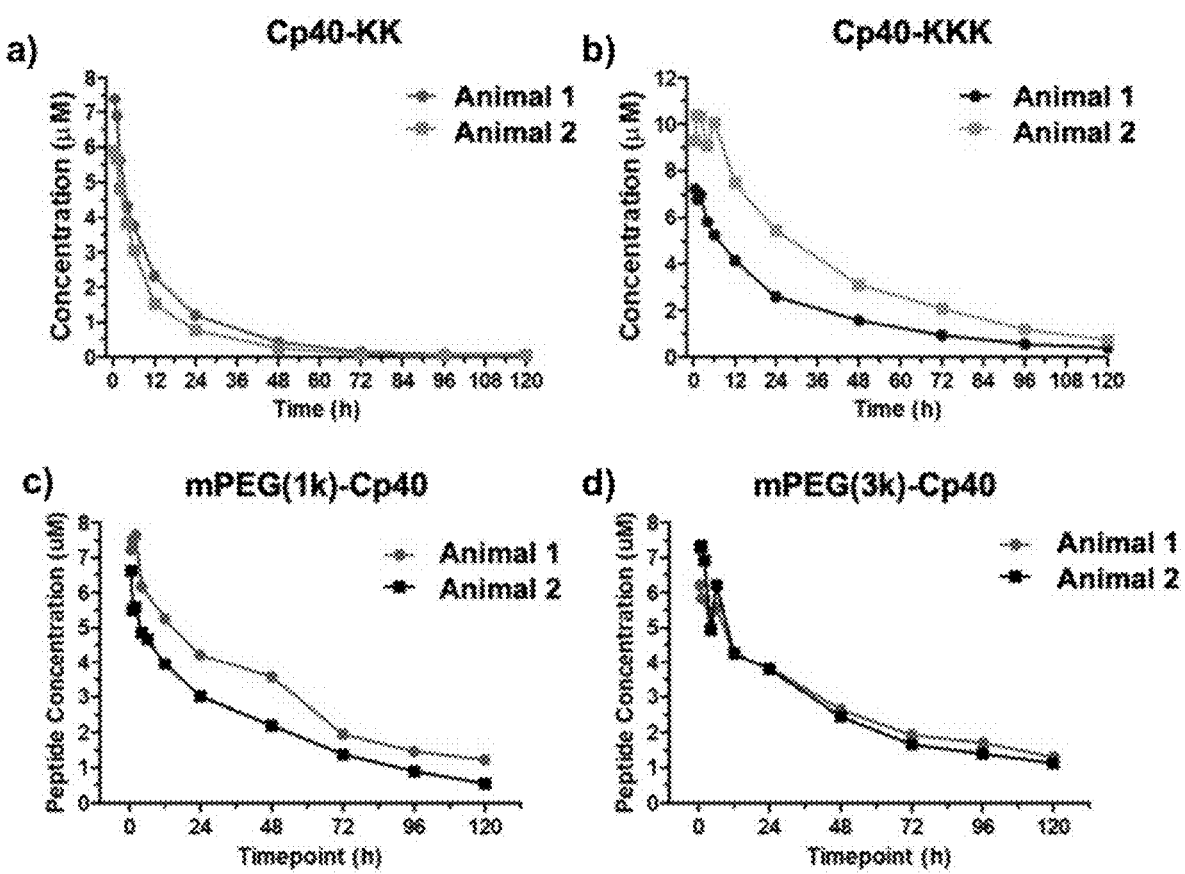
FIG. 11 show graphs of peptide concentration over time in cynomolgus monkeys to which was administered a single 2 mg/kg intravenous injection of Cp40-KK (panel a), Cp40-KKK (panel b), mPEG(1k)-Cp40 (panel c), and mPEG(3k)-Cp40 (panel d). The x-axis represents peptide concentration (nM) in NHP plasma, and the y-axis represents time after injection (hours).

The i.v. injection studies revealed that mPEG(1k)-Cp40, mPEG(3k)-Cp40, and Cp40-KKK have a higher AUC0-120 h (304.4-312 μM h) when compared to the Cp40-KK analog (85.23 μM h) (see Table 5 and FIG. 11). Interestingly, the Cp40-KKK analog displayed the shortest $t_{1/2}$ of the Cp40 analogs tested (see Table 5).

At the same time, while mPEG(1k)-Cp40, Cp40-KK had similar $t_{1/2}$ values, mPEG(3k)-Cp40, in comparison, had an extended $t_{1/2}$ by at least ~30 h (Table 5). The extended $t_{1/2}$ of mPEG(3k)-Cp40 points to the potential for the advancement of this analog as a therapeutic for i.v. treatment of systemic complement-mediated conditions.

Interestingly, as shown in example 4, UPLC/ESI-MS-based quantification of peptide cleavage fragments of Cp40-KK or Cp40-KKK in the plasma of s.c.-injected cynomolgus monkeys revealed that Cp40-KK is cleaved in vivo generating minimal amounts of Cp40-K, while the Cp40-KKK analog is almost completely metabolized into Cp40-KK and small amounts of Cp40-K (see FIG. 7). These data suggest a rapid cleavage of Cp40-KKK to Cp40-KK upon s.c. injection and indicate that the largest proportion of active compound in NHP plasma is represented by the Cp40-KK metabolic species).

Figure 12:
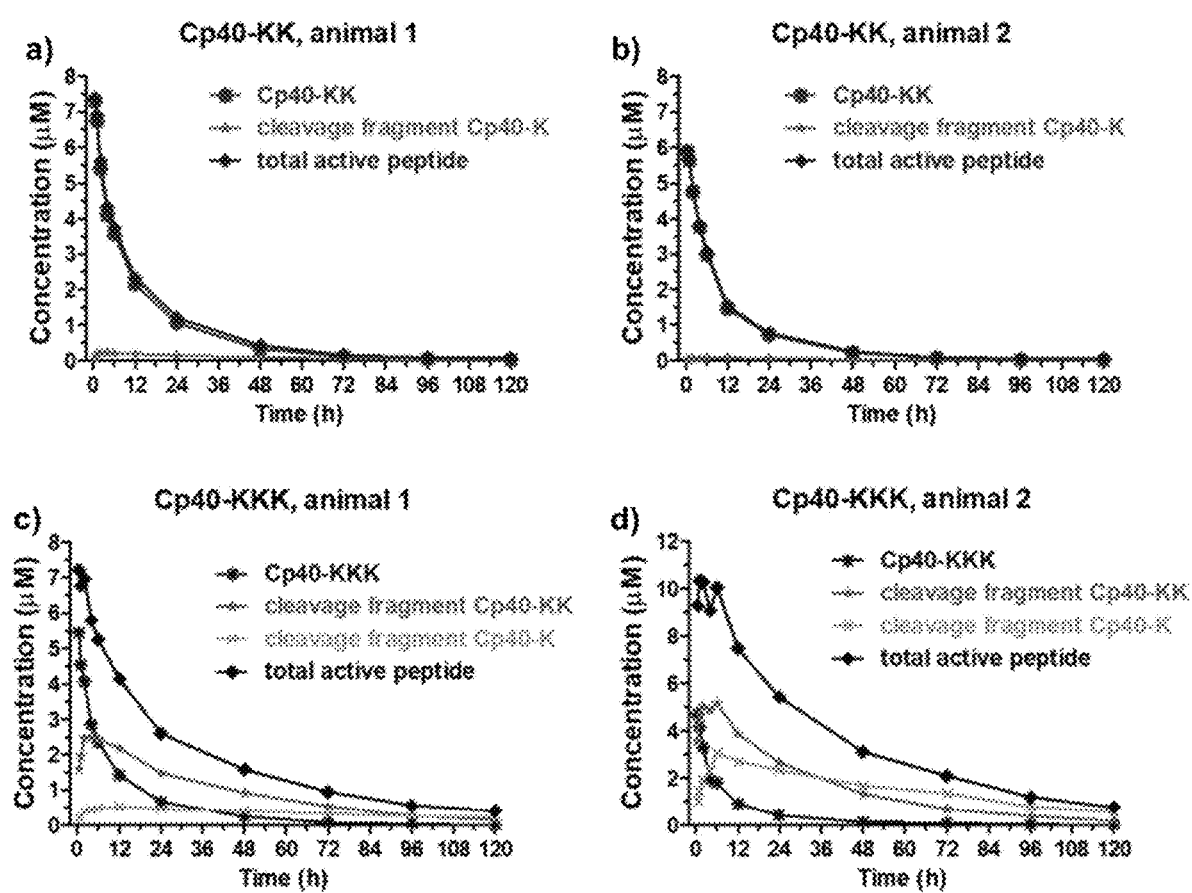
FIG. 12 is a quantification of peptide cleavage fragments in the plasma of cynomolgus monkeys following a single intravenous injection with 2 mg/kg of Cp40-KK (panels a and b) or Cp40-KKK (panels c and d). The x-axis represents peptide concentration (M) in NHP plasma, as determined by UPLC-ESI-MS, and the y-axis represents time after injection (hours).
Figure 18:
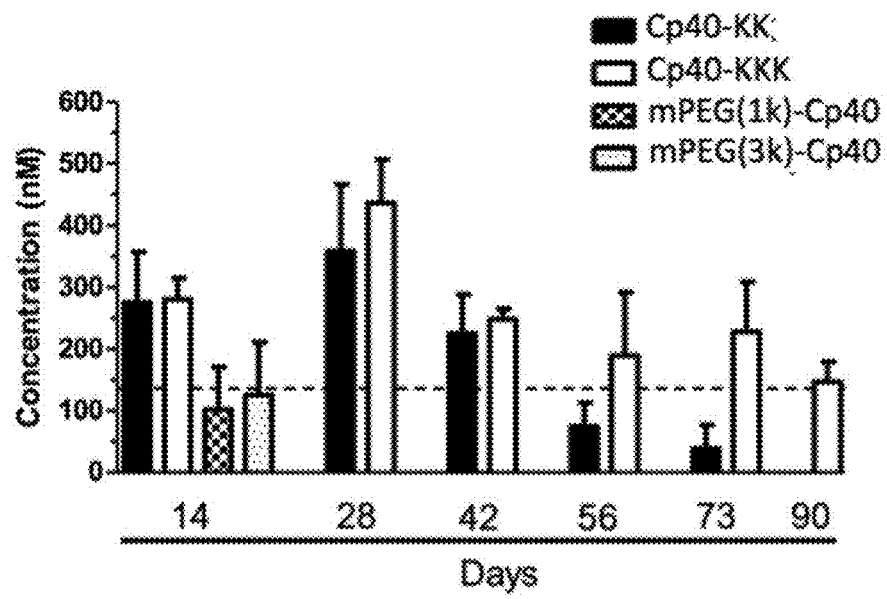
FIG. 18 depicts the concentration of mPEG(3k)-Cp40 (dotted bar), mPEG(1k)-Cp40 (checkered bar), Cp40-KK (black bar), and Cp40-KKK (white bar) compounds detected in the vitreous samples from cynomolgus monkeys after a single intravitreal injection. The x-axis represents the number of days following injection with 500 g of compound, and the y-axis represents the concentration of compound (nM).

Similarly, upon i.v. injection, Cp40-KK was also metabolized to minimal amounts of Cp40-K (see FIG. 12). Further, at 12 h post-injection, most of the Cp40-KKK analog was also metabolized into Cp40-KK and small amounts of Cp40-K (see FIG. 12). Accordingly, the data show that Cp40-KK is the main compound remaining in the circulation upon injection of either Cp40-KK or Cp40-KKK. FIG. 18 is a summary of the in vivo and in vitro Lys-cleavage in Cp40-KK and Cp40-KKK.

Figure 13:
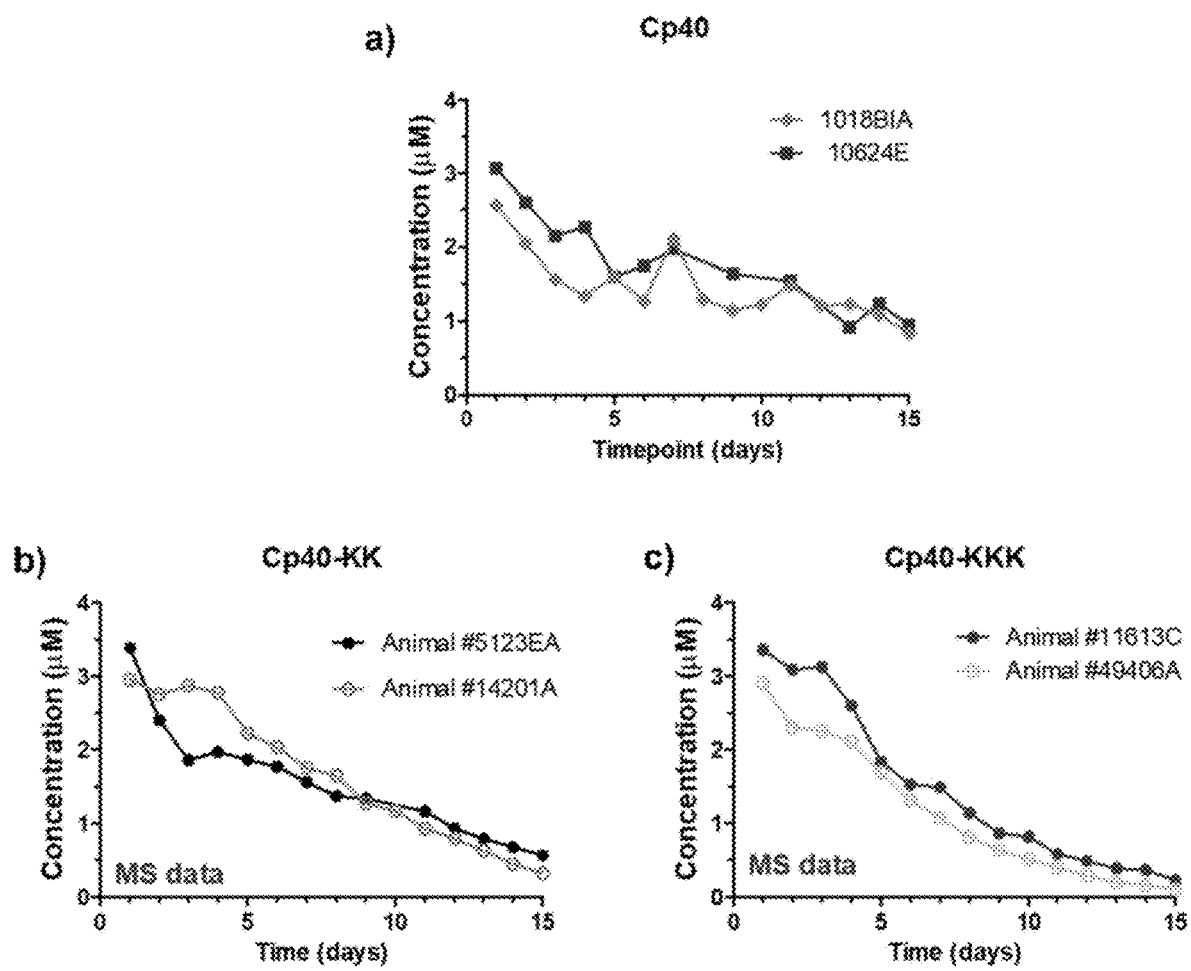
FIG. 13 shows the peptide concentration in NHP plasma from cynomolgus monkeys over time following a single intramuscular injection of 100 mg of Cp40 (panel a), Cp40-KK (panel b), and Cp40-KKK (panel c). The x-axis represents peptide concentration (M) in NHP plasma, as determined by MS, and the y-axis represents time after injection (days).

Example 6. Pharmacokinetic Properties of Cp40-Based Analogs after Intramuscular Administration The pharmacokinetic profiles of Cp40, Cp40-KK and Cp40-KKK were tested in vivo after a single i.m. injection of 100 mg of compound, equivalent to 25 mg/kg (FIG. 13). Notably, the compounds show a different pharmacokinetic profile after i.m injection in relation to the profile observed after i.v. or s.c. injections, thus suggesting that the i.m. administration route may be exploited in novel dosing protocols for the tailored delivery of these compounds in certain complement-mediated indications. Most interestingly, the $t_{1/2}$ after a single i.m. injection of these analogs is about 8 days (FIG. 13). There observations suggest that after an initial s.c. or i.v. injection of the disclosed Cp40 analogs to saturate target levels of the compound, subsequent i.m. injections may be used as a maintenance dose (e.g., administered via i.m. every two weeks).

Example 7. Cp40 and Cp40 Lysine Analog Antibody Generation and Specificity

Figure 14:
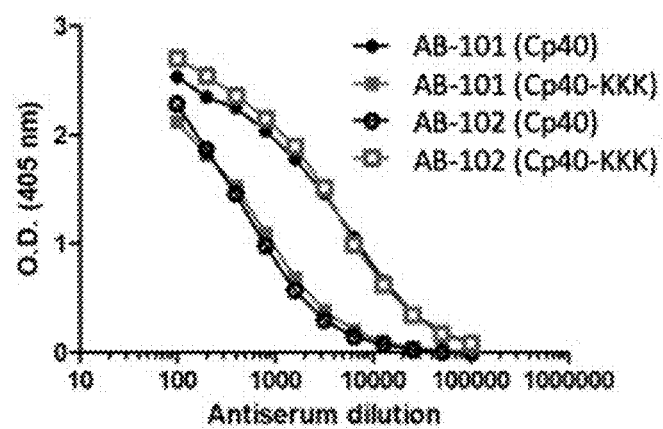
FIG. 14 is an exemplary direct ELISA assay showing the specificity of the Cp40 and Cp40-KKK antibodies fixed in an ELISA plate. The Cp40 antibody (AB-101) reacts with the biological sample containing the Cp40 peptide (solid circle), but with 10-fold lower titer to Cp40-KKK peptide (solid square). Likewise, the Cp40-KKK antibody (AB-102) reacts with the biological sample containing the Cp40-KKK peptide (unshaded square), but with 10-fold lower titer to Cp40 peptide (unshaded circle). The y-axis represents the OD reading at 405 nm, whereas the x-axis represents the antiserum dilution.

To generate antibodies against compstatin analogs for the WES and SPR detection methods described in Examples 8 and 9, rabbits (n=2/analogue) were immunized with 100 μg of Cp40 or other Lysine analogs conjugated with Keyhole limpet hemocyanin (KLH) in the presence of a strong adjuvant (TiterMax Gold-100 μl) followed by weekly injections of 50 μg of KLH-Cp40 plus adjuvant for a total of 5 weeks. Antibody production was monitored with a direct ELISA whereby Cp40-analogs (10 μg/ml) were coated on a 96-well plate, followed by blocking with PBS/1% BSA and incubation with serial dilutions of pre- and post-immunization plasma. The assay was developed after incubation with anti-rabbit IgG conjugated with horseradish peroxidase (HRP), addition of appropriate chromogenic substrate and measurement of absorbance at 405 nm using an ELISA plate reader. This immunization procedure resulted in the production of an anti-Cp40 and an anti-Lys analog antibody (AB101 and AB102, respectively) that were further purified from the rabbit serum by affinity chromatography with Protein A. ELISA and Western blot data show that these antibodies are highly specific as they only react with biological samples (plasma, vitreous) containing the same peptides that were used as immunogens (see FIG. 14 for ELISA. The AB102 antibody showed the same specific for CP40-K, CP40-KK, CP40-KKK. The antigenic epitope of AB101 requires the C-terminal mIle of Cp40 and that of AB102 the C-terminus Lysine residues. Thus these characteristics unique for detecting the CP40 and its analogs.

Example 8. Residence Time of Cp40-Based Analogs in the Vitreous of Non-Human Primates To determine the residence time of mPEG(3k)-Cp40, mPEG(1k)-Cp40, Cp40-KK, and Cp40-KKK in the vitreous of cynomolgus macaques, these Cp40-based analogs were administered intravitreally (i.v.t.) to the animals after induction of light ketamine anesthesia (10-15 mg/kg, by intramuscular injection (i.m.)) and dilation of the pupils with tropicamide/phenylephrine ophthalmic solution (see Table 6 for study design).

TABLE 6

Study design for intravitreal administration and detection of Cp40-based analogs.

| Group | Animal No. | Eye | Treatment | Dose (μg/eye) | N (eyes) |
|---|---|---|---|---|---|
| G1 | K-784, K-792, | Right | Cp40-KK | 500 | 3 |
| G2 | K-799 | Left | Cp40-KKK | 500 | 3 |
| G3 | K-780, K-786, K-800 | Right | PEG(1K)-Cp40 | 500 | 3 |
| G4 | | Left | PEG(3K)-Cp40 | 500 | 3 |

TABLE 6-continued

Study design for intravitreal administration and detection of Cp40-based analogs.

| | G1, G2, G3, G4: Time point of sample collection and photography | | | | | | | |
|---|---|---|---|---|---|---|---|---|
| Day | 0 Pre-dose | 0 Dosing | 14 | 28 | 42 | 56 (G1, G2) | 73 (G1, G2) | 90 (G1, G2) |
| Vitreous fluid | — | — | x | x | x | x | x | x |
| Photography | x | x | x | x | x | x | x | x |

For i.v.t. injection, the cynomolgus monkeys were anesthetized with a combination of ketamine (15-25 mg/kg, i.m.) and xylazine (2 mg/kg, i.m.) and the eye was cleaned with povidone-iodine solution. After application of oxybuprocaine hydrochloride solution (Benoxil® ophthalmic solution 0.4%) to the cornea as a local anesthetic, the Cp40-based analogs were administered to the animals by i.v.t. injection into either the right (G1, G3) or left (G2, G4) eye of each animal. Immediately following each injection, a single topical dose of 0.5% levofloxacin was administered. After i.v.t. injection of mPEG(3k)-Cp40, mPEG(1k)-Cp40, Cp40-KK, and Cp40-KKK, vitreous fluid samples (about 50 µL each) were withdrawn from Cp40-based analog-treated eyes on days 14, 28, 42, (G1, G2, G3, G4), 56, 73, 90 (G1, G2) (this was done either three times or six times). Samples were collected on ice and stored in a deep freezer (−79.3 to −68.5° C.) until further analysis. On day 73 and 90, about 100 µL of vitreous fluid from G1 and G2 were withdrawn. Presence and concentration of the Cp40-based analogs was determined using either the simple western technology (WES, ProteinSimple, San Jose, Calif.), or surface plasmon resonance (SPR)-based real-time measurement of binding kinetics on a Cp40-KKK immobilized chip (see detailed methods below). Similar results with regard to the intravitreal residence time and concentration levels of the test compounds were obtained regardless of the quantification method selected.

Figure 15:
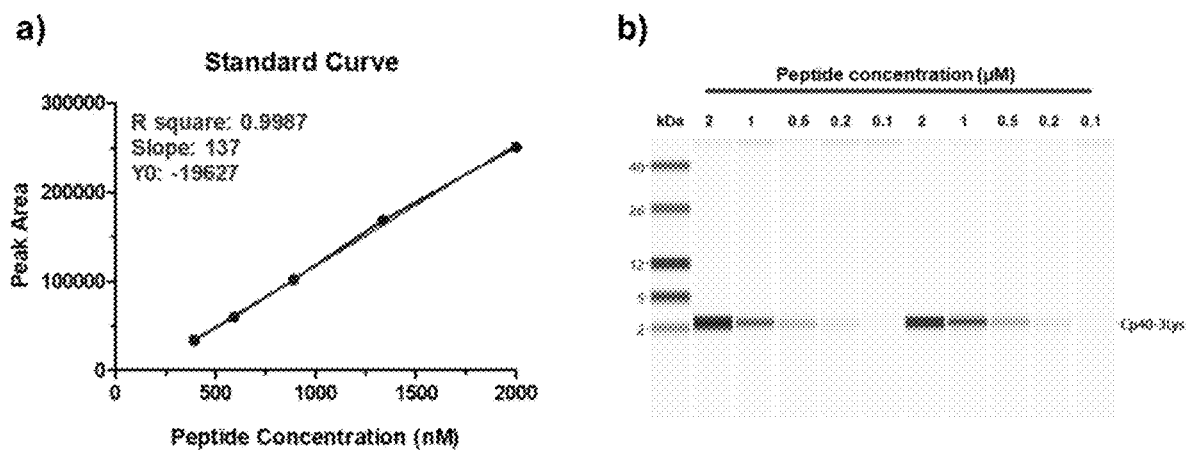
FIG. 15 is a representative five-point standard curve (panel a) and simple western blot gel (panel b) obtained upon running predetermined amounts of Cp40-KKK peptide spiked into rabbit vitreous samples. In panel a), the x-axis represents peptide concentration (nM), and the y-axis represents peak area.

To quantify the levels of all test compounds in vitreous samples collected at different time points following i.v.t. injection (see FIG. 15), WES analysis was performed on a WES instrument (ProteinSimple, San Jose, Calif.) using a 2 to 40 kDa Separation Module and Anti-Rabbit Detection Module according to the manufacturers' instructions. In brief, undiluted eye vitreous samples were mixed with a Fluorescent Master Mix and heated at 95° C. for 5 min. The samples, blocking reagent, primary antibodies (in house developed anti-Cp40; 1:1000 in blocking reagent), HRP-conjugated secondary antibody (anti-rabbit IgG) and chemiluminescent substrate were pipetted into the plate (part of Separation Module). The used instrument settings were: stacking and separation at 375 V for 27 min; blocking reagent for 30 min, primary and secondary antibody both for 30 min; Luminol/peroxide chemiluminescence detection for ~15 min (exposures of 5, 15, 30, 60, 120, 240, and 480 s). The resulting electropherograms were evaluated using the Compass software (ProteinSimple, San Jose, Calif.). The following criteria were used to discriminate low peptide signals from background: The peak signal-to-noise (S/N) ratio given by the software must be ≥10, and the peak height/baseline ratio (calculated manually from the peak height and baseline values given by the software) must be equal to or greater than 3. A five-point standard curve of known concentrations (100-2,000 nM) of peptide spiked in rabbit vitreous was used to calculate peptide concentration in the vitreous samples using the Compass software (Compass Software Inc., Atlanta, Ga.). The curve showed an $R^2$ greater than 0.98. Shown in FIG. 15 is a representative standard curve generated using the WES system and bands obtained upon running pre-determined amounts of purified peptide spiked into rabbit vitreous samples.

Figure 16:
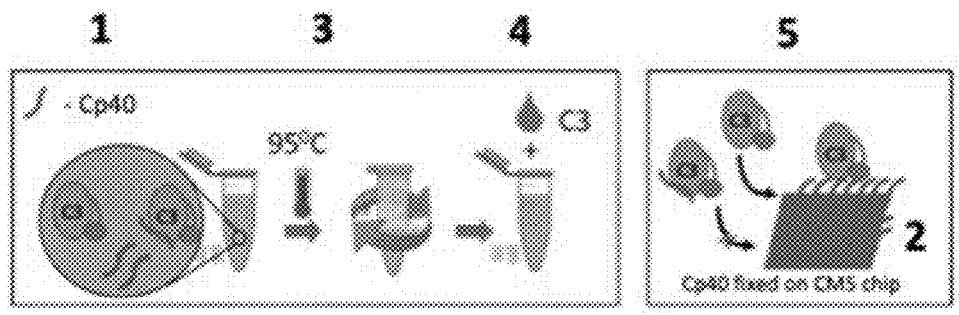
FIG. 16 represents a schematic diagram of the SPR method for quantitation of the Cp40 analogs in biological fluids. Plasma samples were diluted and heated at 95° C. for 5 m (#3) followed by centrifugation and addition of C3 or a plasma source of C3 (#4). The samples were then flown over the corresponding Cp40 analog-immobilized chip (#5).

To corroborate the WES-based measurements for all test compounds, an SPR-based competition assay was developed for detecting Cp40 and Cp40 analogs in biological samples. Briefly, plasma samples diluted 1/1000 were used for testing with or without the addition of Cp40 or Cp40 analogs. The samples were heated at 95° C. for 5 min. After heat treatment, the samples were spun and the supernatant was mixed with a fixed concentration of C3 or plasma as a source of C3 and flown over a CM5 sensor chip to which the corresponding Cp40 analog was immobilized (e.g., covalently attached). The response was then measured and compared to a standard curve for quantitation. A schematic of the SPR-based method is summarized in FIG. 16.

The novel SPR-based competition assay was performed on the same vitreous samples using a Biacore 3000 instrument (GE Healthcare, Piscataway Township, N.J.) at 25° C. Cp40-KKK was covalently attached to a CM5 sensor chip using standard amine coupling reactions with HBS-EP as running buffer. Briefly, the chip was activated for 7 min with NHS/EDC (1:1), coated with Cp40-KKK using 300 µg/ml Cp40-KKK in 5 mM sodium acetate (pH 5.0) for 6 min, and deactivated with 1 M ethanolamine-HCl (pH 9.5) for 10 min. An empty flow cell served as reference surface. In order to eliminate non-specific binding during the experiments, the running buffer was changed to 50 mM phosphate buffer (pH 7.4) containing 100 mM NaCl, 0.05% Tween 20, 10 mM EDTA and 1 mg/ml dextran sulfate (500 kDa). Experiments were all carried out at a flow rate of 10 µl/min with 2 min of sample injection followed by regeneration of the surface of the sensor chip. The surface was regenerated with subsequent injection of 0.5% SDS for 1 min and 50 mM glycine buffer (pH 9.5) for 30 s.

Figure 17:
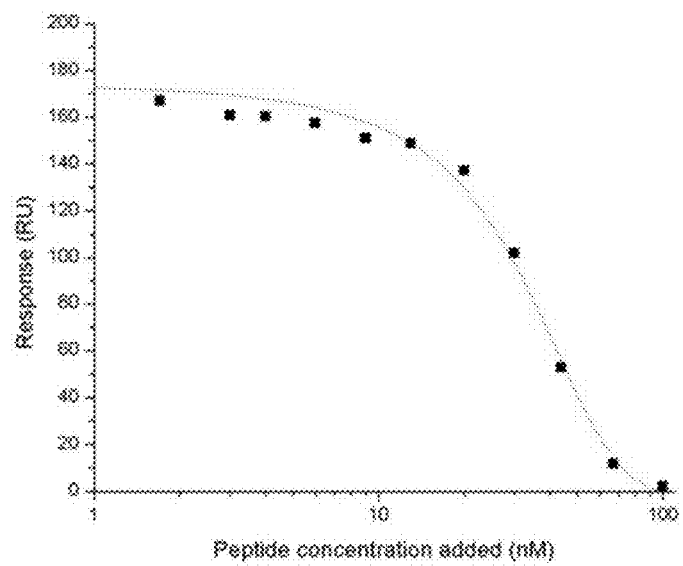
FIG. 17 is a representative standard curve obtained via surface plasmon resonance analysis of rabbit vitreous samples spiked with predetermined amounts of Cp40-KKK peptide. The x-axis represents peptide concentration (nM), and the y-axis represents relative light units.

Depicted in FIG. 17 is a representative standard curve of the relevant Cp40-based analog that was prepared by diluting pre-determined concentrations of peptide with rabbit vitreous followed by heat-inactivation for 5 min at 95° C. and 10 min equilibration in a room temperature water bath. The standard samples were centrifuged for 10 min at 14,000×g and supernatants were mixed with normal human plasma. Similarly, for the detection of unknown concentrations of mPEG(3k)-Cp40, mPEG(1k)-Cp40, Cp40-KK, and Cp40-KKK in eye vitreous, samples were diluted in running buffer followed by heat-inactivation, equilibration, and centrifugation as described above. Sample supernatants were mixed with diluted human plasma as described above and injected. Data processing was performed using the Scrubber software (BioLogic Software, Campbell, Australia).

As shown in FIG. 18, Cp40-KK, Cp40-KKK, PEG(1K)-Cp40, PEG(3K)-Cp40 were detected in the vitreous collected from treated animals 14 days after a single 0.5 mg injection of the Cp40-based analog. It should be noted that the PEG(1K)-Cp40 and PEG(3K)-Cp40 compounds were detected at day 14 post injection but not in later time points (see FIG. 18), indicating that the vitreous residence time of PEGylated-compounds is at least 14 days, but significantly shorter than that of the lysine-containing compounds (i.e., Cp40-KK and Cp40-KKK).

The Cp40-KK and Cp40-KKK peptides were detected at days 14, 28, 42, 56, 73 and 90 post-injection (FIG. 18). While the concentration of CP40-KK in the NHP vitreous decreases over time, from days 42 to 73, concentration levels of Cp40-KKK remained stable during the 73-day observation period (FIG. 18). Of note, Cp40-KKK showed the longest residence time in the ocular tissues as it was detected even at day 90 post-treatment. Conversely, the residence time of Cp40-KK in the vitreous was markedly shorter than that of Cp40-KKK, as it was no longer detected on day 90. It should be noted that the intravitreal concentration of Cp40-KKK reached and maintained saturating levels with regard to those of its target C3 in the intravitreal compartment (0-140 nM; see Loyet K M et al., 2012, Invest Ophthalmol Vis Sci. 53:6628-37) during the entire observation period leading up to day 90 (see FIG. 18, dotted line).

While the addition of mini-PEG moieties or the extension of a peptide with charged, hydrophilic residues, such as Lysine, are both chemical modifications known in the art for their capacity to increase a peptide's solubility, the markedly increased residence time of Cp40-KK and Cp40-KKK in ocular tissues was a very surprising result and had not previously been reported. The prolonged ocular residence of the test compound (Cp40-KK and Cp40-KKK) is unique to its structure and, while not intending to be bound by theory, may be attributed to a tissue-specific mechanism exploiting the presence of the tandem Lys repeat at the C-terminus of the compound. This is further supported by the observation that while the mini-PEGylated Cp40 exhibits comparable solubility profiles with the Cp40-Lys (n) compounds (see Table 1), it has distinctly shorter ocular residence than Cp40-KK or Cp40-KKK. Moreover, the unexpected and significant increase in ocular residence afforded by the addition of a third Lys residue to Cp40-KKK as compared to the Cp40-KK derivative cannot merely be explained by taking into account their similar solubility profiles (see Table 1), but rather points to a novel pathway by which the Cp40-KKK is retained in the vitreous humor for a longer period even as compared to the Cp40-KK analog.

Of note, the amount of compounds detected in the vitreous of treated cynomolgus monkeys on day 14 represents approximately 0.2% of the initially injected dose, which suggests a biphasic, target-driven elimination profile whereby the compound in excess of the target C3 concentration is rapidly cleared from the eye and only the compound that is tightly bound to its target remains longer in the tissue. In other words, i.v.t. administration with these Cp40-based analogs can achieve the observed residence time at much lower doses (e.g., even less than about 10 g or even 1-2 g). Conversely, when 100 g of Cp40 was i.v.t administered no detection of any compound was observed after one month suggesting that the residence time of Cp40 is very short as compared to the Cp40-based analogs discussed herein. Therefore, the disclosed Cp40-based analogs confer a beneficial increase in residence time in addition to enhanced solubility as compared to Cp40.

In summary, the data above show that the intravitreal residence time of Cp40-KK is less than Cp40-KKK, and the residence time of Cp40-KKK is equal to or exceeds about 3 months after i.v.t. These findings have important implications for the design of chronic administration protocols for the treatment of ocular diseases and other clinical pathologies with involvement of deregulated complement activation. The prolonged ocular residence of Cp40-KK and Cp40-KKK will enable the application of new drug dosing schemes that involve a significantly reduced dosing frequency with lesser patient burden, compared to that of the previous generation compounds analogs Cp40 and APL-2.

Figure 19:
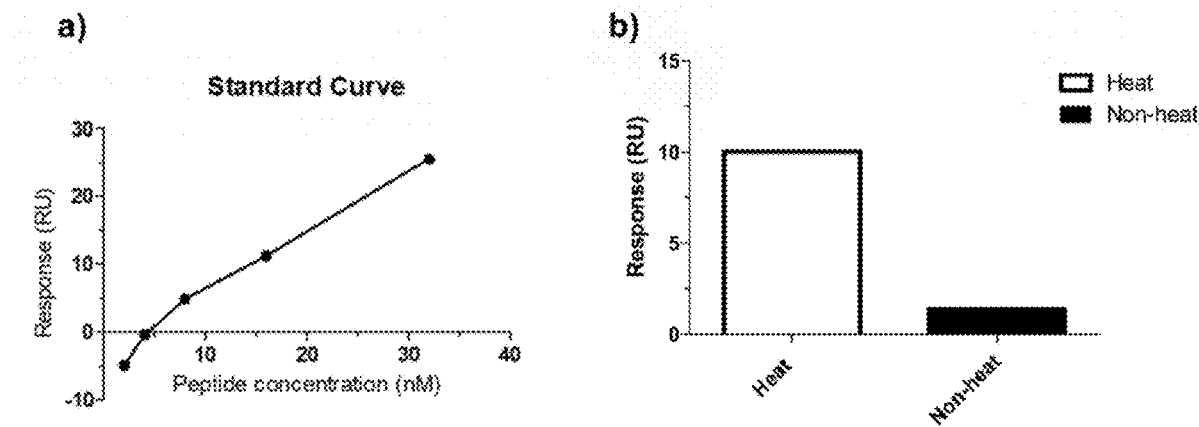
FIG. 19 is an SPR profile of Cp40-KKK binding to purified C3b. Panel a) is a positive control, standard curve showing C3b binding by Cp40-KKK added to rabbit vitreous at concentrations of 2, 4, 8, and 16 nM. The x-axis represents peptide concentration (nM), and the y-axis represents relative light units. Panel b) shows the C3b binding signal obtained from NHP eye vitreous injected with Cp40-KKK. The y-axis represents relative light units. The vitreous samples were either subjected to heat inactivation (white bar) or not subjected to heat inactivation (black bar) prior to chip immobilization.

Example 9. Activity of Lysine-Containing Cp40-Based Analogs in the Vitreous of Non-Human Primates To confirm that the compound present in the NHP vitreous maintains C3b-binding activity, which is a prerequisite for eliciting its inhibitory action across all complement pathways, surface plasmon resonance (SPR) binding experiments were conducted. Briefly, for a positive binding control, serial dilutions of Cp40-KKK (16, 8, 4, and 2 nM) were added to rabbit vitreous samples and flowed onto a Biacore CM5 chip immobilized with purified human C3b (Complement Technology Inc, Tyler, Tex.) (see FIG. 19A). Next, vitreous samples were collected from a Cp40-KKK injected eye at day 14 post-injection and subjected to heat-inactivation at 95° C. for 5 min. Both heat-inactivated and non-heat-inactivated samples were flowed onto a CM5 chip immobilized with purified human C3b as indicated above (FIG. 19B).

As shown in FIG. 14A, Cp40-KKK spiked into rabbit vitreous samples binds to C3b in a dose-dependent manner. Further, signal for C3b binding is observed upon the testing of vitreous samples collected from an eye injected with Cp40-KKK (FIG. 19B), indicating that Cp40-KKK present in the vitreous maintains its C3b-binding activity.

Notably, the C3b-binding signal obtained with a vitreous sample that was heat-inactivated (FIG. 19B, left bar) was higher when compared with the signal resulting from the non-heat inactivated (FIG. 19B, right bar) sample (10 vs. 2 relative units, respectively). As the heat-inactivation step assures the dissociation of the compound from its target, the differential response observed in the SPR analysis likely indicates that the majority of the compound is bound to the complement C3 protein in the vitreous. This observation is in concordance with the high-affinity, tight binding of Cp40 and its derivatives (Cp40-KKK, Cp40-KK) to C3 and aligns with the biphasic target-driven elimination profile of these compounds, as previously reported in NHP studies (see Risitano et al., 2014, Blood 123(13):2091-2101; Berger et al., 2018, J Med Chem 61(14):6153-6162).

An alternative explanation to the one presented above is that the vitreous contains additional unidentified factors that associate with the Cp40-KKK analog. To investigate whether an unidentified vitreous factor impacts the complement inhibitory activity of lysine containing compounds, complement activation assays were performed using vitreous samples. Briefly, human plasma was incubated with OVA-anti-OVA immune-complexes in the presence of serial dilutions of the Cp40-based analogs mixed with rabbit vitreous. Levels of classical pathway activation (C3b deposition) were determined by ELISA using a polyclonal anti-human C3 antibody conjugated with HRP (MP Biomedicals, Solon, Ohio) (FIG. 20).

Figure 20:
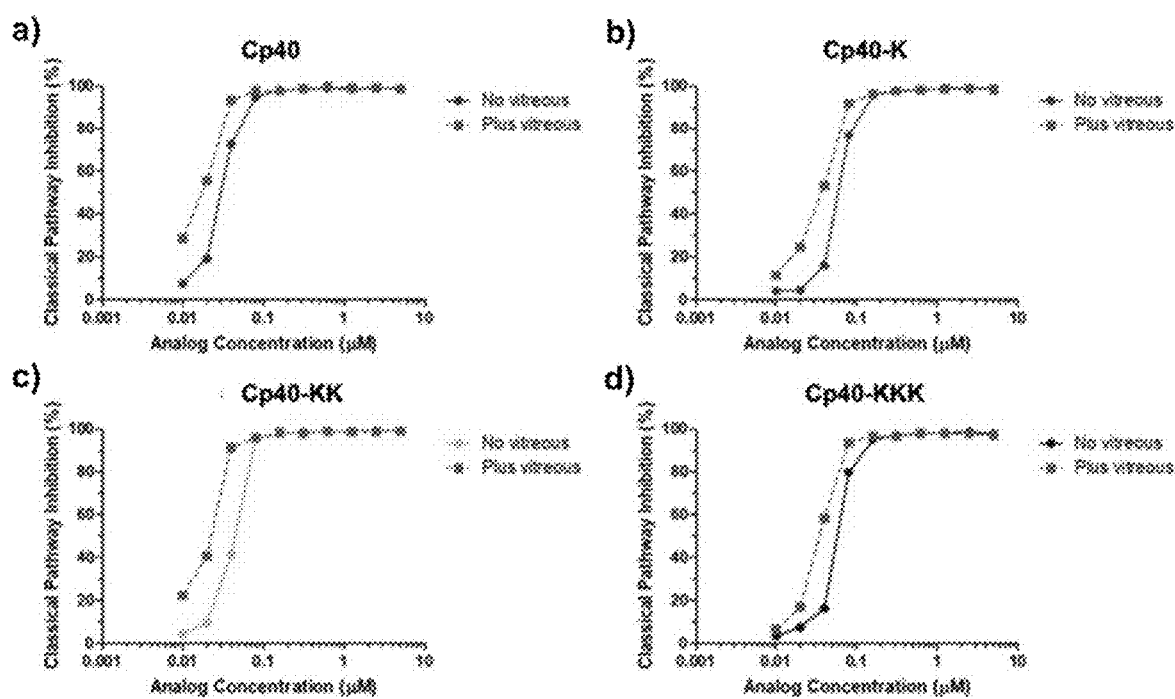
FIG. 20 depicts classical complement pathway inhibition in human eye plasma incubated with Cp40 (panel a), Cp40-K (panel b), Cp40-KK (panel c), and Cp40-KKK (panel d) in the presence of rabbit vitreous (square) or absence of rabbit vitreous (circle). The x-axis represents analog concentration (nM), and the y-axis represents percent inhibition of C3b deposition.

As shown in FIG. 20, in the absence of vitreous, all the compounds tested (Cp40, Cp40-1K, Cp40-KK, Cp40-KKK) show complement classical pathway-mediated inhibitory activity in a dose-dependent manner (solid lines). Notably, the vitreous samples appear to have a minor complement inhibitory activity as the presence of vitreous appears to potentiate the complement inhibitory activity of the tested compounds (FIG. 20, compare dashed lines with solid lines). Thus, the data indicate that the activity of tested compounds (i.e., Cp40 and its lysine-containing derivatives) is not inhibited by unidentified factors in the vitreous that may bind to some extent these compounds Summary: Comparison of the PK Properties of Individual Analogues Via Different Administration Routes and their Potential for the Development of Therapeutics.

The data shown in Example 8 indicated that the Cp40-KKK and Cp40-KK compounds exhibit improved residence time in the eye vitreous when compared with other tested compounds while maintaining their binding activity, hence supporting the potential for development of these molecules as therapeutics for ocular conditions. Additionally, pharmacokinetic data obtained from subcutaneous (s.c.) and intravenous (i.v.) studies in cynomolgus monkeys indicated that mPEG(1k)-Cp40, mPEG(3k)-Cp40, Cp40-KK, and Cp40-KKK have discrete pharmacokinetic properties from their parental molecule, Cp40, and, by virtue of these pharmacokinetic properties, have unique potential to be developed as both locally and systemically administered therapeutics for modulating complement activity in clinical disorders (see FIGS. 6 and 11; Table 4).

Figure 21:
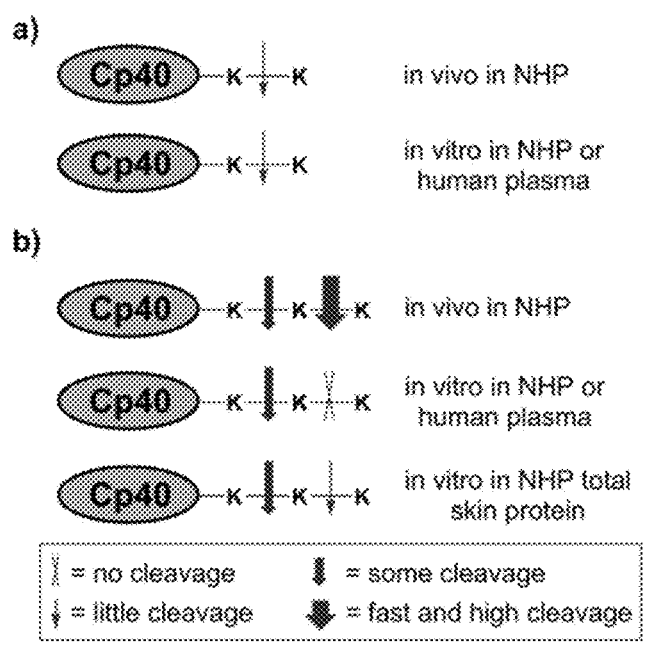
FIG. 21 is a summary of the in vivo and in vitro Lys-cleavage in Cp40-KK (panel a) and Cp40-KKK (panel b).

Specifically, s.c. administration of the Cp40-KKK compound saturates C3 plasma levels for about 40 h, which is about 7-fold longer than the saturation period observed with unmodified Cp40 (Example 4; FIG. 6E). The long target saturation period of Cp40-KKK, in combination with its increased solubility, confers a unique potential for development as a s.c. therapeutic, suitable for the treatment of systemic and/or chronic complement-mediated conditions. The unique structure of the Cp40-KKK analog may dictate its prolonged half-life and likely enhanced biodistribution in different compartments, such as the eye vitreous, due to potential depot effects that may promote its accumulation during a multiple dosing regimen and its slower release into the targeted tissue through potential interactions with other unknown carrier-like or binding proteins. Moreover, the observation that a significant amount of the Cp40-K metabolite was detected in the plasma of Cp40-KKK-injected cynomolgus monkeys (FIG. 12), whereas this metabolite was almost absent from the plasma of CP40-KK-injected animals, indicates that the Cp40-KK metabolite may likely be more stable in the circulation (e.g., less prone to further proteolytic degradation) and that the addition of a third lysine residue to the C-terminus of the parental Cp40 confers a new biotransformation profile and novel pharmacokinetic properties to the resulting peptide that collectively enhance its plasma and intravitreal residence. These characteristics thus afford the Cp40-KKK analog a more favorable pharmacokinetic profile that can enable chronic administration of this analog with less frequent dosing intervals. Shown in FIG. 21 is a summary of the in vivo and in vitro Lys-cleavage in Cp40-KK and Cp40-KKK.

Similarly the extended $t_{1/2}$ of mPEG(3k)-Cp40, observed after i.v. injection in NHP (Example 5; Table 5), points to the potential for the advancement of this analog as a therapeutic for i.v. treatment of systemic complement-mediated conditions. Moreover, as shown in example 6, the i.m. administration route may be exploited in novel dosing protocols for the tailored delivery of the Cp40 analogues in complement-mediated indications.

The present invention is not limited to the embodiments described and exemplified herein, but is capable of variation and modification within the scope of the appended claims.

What is claimed:

1. A compound comprising a peptide consisting of SEQ ID NO: 9 or SEQ ID NO: 10, wherein the peptide has a binding affinity ($K_D$) for at least one of C3 or its fragments C3b, iC3b or C3c, that is greater, under equivalent assay conditions, than the binding affinity of SEQ ID NO:7 for the same at least one of C3 or its fragments C3b, iC3b, or C3c.

2. A pharmaceutical composition comprising the compound of claim 1 and a pharmaceutically acceptable carrier.

3. The pharmaceutical composition of claim 2, formulated for administration to an individual by a route selected from the group consisting of: oral, intranasal, topical, intraocular, periodontal, pulmonary, subcutaneous, intramuscular and intravenous.

4. The pharmaceutical composition of claim 3, wherein: (a) the intraocular administration is intravitreal administration; or (b) the periodontal administration is gingival administration or intrapapillary infiltration injection of the compound.

5. A peptide consisting of SEQ ID NO:9 or SEQ ID NO:10, wherein the peptide has a binding affinity ($K_D$) for at least one of C3 or its fragments C3b, iC3b or C3c, that is greater, under equivalent assay conditions, than the binding affinity of SEQ ID NO:7 for the same at least one of C3 or its fragments C3b, iC3b, or C3c.

6. A method of treating an individual having a pathological condition associated with complement activation, the method comprising the steps of:
 (1) providing the individual having the pathological condition associated with complement activation;
 (2) administering to the individual a therapeutically effective amount of a pharmaceutical composition comprising a pharmaceutically acceptable carrier and a compound comprising a peptide consisting of SEQ ID NO: 9 or SEQ ID NO: 10, wherein the peptide has a binding affinity ($K_D$) for at least one of C3 or its fragments C3b, iC3b or C3c, that is greater, under equivalent assay conditions, than the binding affinity of SEQ ID NO:7 for the same at least one of C3 or its fragments C3b, iC3b, or C3c; and (3) measuring one or more parameters of complement activation or of the pathological condition in the individual;

wherein administering of the pharmaceutical composition results in inhibition of complement, thereby treating the individual having the pathological condition associated with complement activation.

7. The method of claim 6, wherein the pathological condition associated with complement activation is selected from the group consisting of: atypical hemolytic uremic syndrome (aHUS); dense deposit disease (DDD); C3 glomerulonephritis (C3GN); C3 glomerulopathies; complement-mediated nephropathies and glomerular inflammatory diseases; age-related macular degeneration (AMD); eye disorder characterized by macular degeneration, choroidal neovascularization (CNV), retinal Neovascularization (RNV), proliferative vitreoretinopathy, glaucoma, uveitis, ocular inflammation, or any combination of these; paroxysmal nocturnal hemoglobinuria (PNH); cold agglutinin disease (CAD); warm antibody autoimmune hemolytic anemias (wAIHAs); sickle cell disease; transplant-associated thrombotic microangiopathies; rheumatoid arthritis (RA); systemic lupus erythematosus (SLE); autoimmune and autoinflammatory kidney diseases; autoimmune myocarditis; multiple sclerosis; traumatic brain and spinal cord injury; cerebral, intestinal and renal ischemia-reperfusion (IR) injury; spontaneous and recurrent pregnancy loss; anti-phospholipid syndrome (APS); Parkinson's disease; Alzheimer's disease; neurodegenerative inflammatory conditions underpinned by aberrant synaptic remodeling, microglial activity and cognitive decline; asthma; anti-nuclear cytoplasmic antigen-associated pauci-immune vasculitis (Wegener's syndrome); non-lupus autoimmune skin diseases; post-traumatic shock; cancer; periodontitis; gingivitis; atherosclerosis; asthma, chronic obstructive pulmonary disease (COPD), allergic inflammation, emphysema, bronchitis, bronchiectasis, cystic fibrosis, tuberculosis, pneumonia, neonatal or adult respiratory distress syndrome (RDS), rhinitis and sinusitis.

8. The method of claim 6, wherein the pharmaceutical composition is administered intravenously or subcutaneously at a therapeutically effective dose of between about 0.125 mg/kg and about 10 mg/kg.

9. The method of claim 6, wherein the pharmaceutical composition is administered intramuscularly at a therapeutically effective dose of between about 0.25 mg/kg and about 50 mg/kg.

10. The method of claim 6, wherein the pharmaceutical composition is administered intravitreally at a therapeutically effective dose of between about 1 µg and about 10 mg.

11. The method of claim 6, wherein the pharmaceutical composition is administered periodontally at a therapeutically effective dose of between about 1 µg and about 1,000 µg.

12. The method of claim 6, wherein the pharmaceutical composition is administered orally at a therapeutically effective dose of between about 1 mg and about 20 mg.

13. The method of claim 6, wherein the pharmaceutical composition is administered in regular intervals ranging from once every 12 hours to once every 3 months.

14. The method of claim 6, wherein the pharmaceutical composition is administered intravenously or subcutaneously to the individual at a first therapeutically effective dose of between about 0.125 mg/kg and about 10 mg/kg, and wherein the pharmaceutical composition is further administered: (i) intramuscularly at a second therapeutically effective maintenance dose of between about 0.25 mg/kg and about 50 mg/kg; or (ii) orally at a second therapeutically effective maintenance dose of between about 1 mg/kg and about 20 mg/kg.

15. The method of claim 6 wherein the individual is a human or a non-human primate.

* * * * *

UNITED STATES PATENT AND TRADEMARK OFFICE
CERTIFICATE OF CORRECTION

PATENT NO. : 10,800,812 B2
APPLICATION NO. : 16/774934
DATED : October 13, 2020
INVENTOR(S) : John D. Lambris It is certified that error appears in the above-identified patent and that said Letters Patent is hereby corrected as shown below:

In the Specification

In Column 17, Line 24, the reference to the table, which states "Table 2" should be corrected to --Table 3--;

In Column 17, Line 29, the reference to the table which states "Table 2" should be corrected to --Table 3--;

In Column 20, Lines 40-43, the sequence which states "DTyr-Ile-[Cys-Val-Trp(Me)-Gln-Asn-Trp-Sar-Ala-His-Arg-Cys]-mIle-NH$_2$" should be corrected to --DTyr-Ile-[Cys-Val-Trp(Me)-Gln-Asp-Trp-Sar-Ala-His-Arg-Cys]-mIle-NH$_2$--;

In Column 20, Lines 44-48, the sequence which states "DTyr-Ile-[Cys-Val-Trp(Me)-Gln-Asn-Trp-Sar-Ala-His-Arg-Cys]-mIle-Lys-NH$_2$" should be corrected to --DTyr-Ile-[Cys-Val-Trp(Me)-Gln- Asp-Trp-Sar-Ala-His-Arg-Cys]-mIle-Lys-NH$_2$--;

In Column 20, Lines 49-53, the sequence which states "DTyr-Ile-[Cys-Val-Trp(Me)-Gln-Asn-Trp-Sar-Ala-His-Arg-Cys]-mIle-Lys-Lys-NH$_2$" should be corrected to --DTyr-Ile-[Cys-Val-Trp(Me)-Gln-Asp-Trp-Sar-Ala-His-Arg-Cys]-mIle-Lys-Lys-NH$_2$--;

In Column 20, Lines 54-58, the sequence which states "DTyr-Ile-[Cys-Val-Trp(Me)-Gln-Asn-Trp-Sar-Ala-His-Arg-Cys]-mIle-Lys-Lys-Lys-NH$_2$" should be corrected to --DTyr-Ile-[Cys-Val-Trp(Me)-Gln-Asp-Trp-Sar-Ala-His-Arg-Cys]-mIle-Lys-Lys-Lys-NH$_2$--;

In Column 45, Lines 66-67, the sequence which states "Cp40 (DTyr-Ile-[Cys-Val-Trp(Me)-Gln-Asn-Trp-Sar-Ala-His-Arg-Cys]-mIle-NH$_2$" should be corrected to --Cp40 (DTyr-Ile-[Cys-Val-Trp(Me)-Gln-Asp-Trp-Sar-Ala-His-Arg-Cys]-mIle-NH$_2$--;

Signed and Sealed this
Twentieth Day of July, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,800,812 B2

In Column 50, Lines 63-65, the sequence which states "DTyr-Ile-[Cys-Val-Trp(Me)-Gln-Asn-Trp-Sar-Ala-His-[13C6;15N4]Arg-Cys]-mIle-NH$_2$" should be corrected to --DTyr-Ile-[Cys-Val-Trp(Me)-Gln-Asp-Trp-Sar-Ala-His-[13C6;15N4]Arg-Cys]-mIle-NH$_2$--; and In Column 52, Line 40, the reference to the figure which states "FIG. 3B" should be changed to --FIG. 6B--.

SEQUENCE LISTING

```
<160> NUMBER OF SEQ ID NOS: 10

<210> SEQ ID NO 1
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: DISULFID
<222> LOCATION: (2)..(12)

<400> SEQUENCE: 1

Ile Cys Val Val Gln Asp Trp Gly His His Arg Cys Thr
1               5                   10

<210> SEQ ID NO 2
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is missing or is Gly.
<220> FEATURE:
<221> NAME/KEY: VARIANT
<222> LOCATION: (2)..(2)
<223> OTHER INFORMATION: Xaa is Ile, Val, Leu, Ac-Ile, Ac-Val, or
```

```
        Ac-Leu.
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
<221> NAME/KEY: VARIANT
<222> LOCATION: (8)..(8)
<223> OTHER INFORMATION: Xaa is Trp or an analog of Trp
<220> FEATURE:
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (14)..(14)
<223> OTHER INFORMATION: Xaa is L-Thr, D-Thr, Ile, Val, or Gly.
<220> FEATURE:
<221> NAME/KEY: MOD_RES
<222> LOCATION: (14)..(14)
<223> OTHER INFORMATION: AMIDATION (optional)
<220> FEATURE:
<221> NAME/KEY: VARIANT
<222> LOCATION: (15)..(15)
<223> OTHER INFORMATION: Xaa is missing or is Asn or Ala.
<220> FEATURE:
<221> NAME/KEY: MOD_RES
<222> LOCATION: (15)..(15)
<223> OTHER INFORMATION: AMIDATION (optional)
<220> FEATURE:
<221> NAME/KEY: VARIANT
<222> LOCATION: (16)..(16)
<223> OTHER INFORMATION: Xaa is missing or is Asn.
<220> FEATURE:
<221> NAME/KEY: MOD_RES
<222> LOCATION: (16)..(16)
<223> OTHER INFORMATION: AMIDATION (optional)

<400> SEQUENCE: 2

Xaa Xaa Cys Val Xaa Gln Asp Xaa Gly Xaa His Arg Cys Xaa Xaa Xaa
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is missing or is Gly.
<220> FEATURE:
<221> NAME/KEY: VARIANT
<222> LOCATION: (2)..(2)
<223> OTHER INFORMATION: Xaa is Ile, Val, Leu, Ac-Ile, Ac-Val, or
      Ac-Leu.
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp.
<220> FEATURE:
<221> NAME/KEY: VARIANT
<222> LOCATION: (8)..(8)
<223> OTHER INFORMATION: Xaa is Trp or an analog of Trp.
<220> FEATURE:
<221> NAME/KEY: MOD_RES
<222> LOCATION: (9)..(9)
<223> OTHER INFORMATION: N-METHYLATION
<220> FEATURE:
<221> NAME/KEY: VARIANT
```

```
<222> LOCATION: (10)..(10)
<223> OTHER INFORMATION: Xaa is His, Ala, Phe, or Trp.
<220> FEATURE:
<221> NAME/KEY: VARIANT
<222> LOCATION: (14)..(14)
<223> OTHER INFORMATION: Xaa is Thr, Ile, Leu, Nle, N-methyl Thr, or
      N-methyl Ile.
<220> FEATURE:
<221> NAME/KEY: MOD_RES
<222> LOCATION: (14)..(14)
<223> OTHER INFORMATION: AMIDATION (optional)

<400> SEQUENCE: 3

Xaa Xaa Cys Val Xaa Gln Asp Xaa Gly Xaa His Arg Cys Xaa
1               5                   10

<210> SEQ ID NO 4
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (13)..(13)
<223> OTHER INFORMATION: METHYLATION
<220> FEATURE:
<221> NAME/KEY: MOD_RES
<222> LOCATION: (13)..(13)
<223> OTHER INFORMATION: AMIDATION

<400> SEQUENCE: 4

Ile Cys Val Trp Gln Asp Trp Gly Ala His Arg Cys Ile
1               5                   10

<210> SEQ ID NO 5
<211> LENGTH: 14
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is missing or is Tyr, D-Tyr, or Sar.
<220> FEATURE:
<221> NAME/KEY: VARIANT
<222> LOCATION: (2)..(2)
<223> OTHER INFORMATION: Xaa is Ile, Gly, or Ac-Trp.
<220> FEATURE:
<221> NAME/KEY: DISULFID
<222> LOCATION: (3)..(13)
<223> OTHER INFORMATION: optional disulfide bond or thioether bond
<220> FEATURE:
<221> NAME/KEY: THIOETH
<222> LOCATION: (3)..(13)
<223> OTHER INFORMATION: optional disulfide bond or thioether bond
<220> FEATURE:
<221> NAME/KEY: VARIANT
<222> LOCATION: (5)..(5)
```

```
<223> OTHER INFORMATION: Xaa is Trp or an analog of Trp.
<220> FEATURE:
<221> NAME/KEY: VARIANT
<222> LOCATION: (7)..(7)
<223> OTHER INFORMATION: Xaa is Asp or Asn.
<220> FEATURE:
<221> NAME/KEY: VARIANT
<222> LOCATION: (8)..(8)
<223> OTHER INFORMATION: Xaa is Trp or an analog of Trp.
<220> FEATURE:
<221> NAME/KEY: MOD_RES
<222> LOCATION: (9)..(9)
<223> OTHER INFORMATION: N-Methylation (optional)
<220> FEATURE:
<221> NAME/KEY: VARIANT
<222> LOCATION: (10)..(10)
<223> OTHER INFORMATION: Xaa is His, Ala, Phe, or Trp.
<220> FEATURE:
<221> NAME/KEY: VARIANT
<222> LOCATION: (12)..(12)
<223> OTHER INFORMATION: Xaa is Arg or Orn.
<220> FEATURE:
<221> NAME/KEY: VARIANT
<222> LOCATION: (14)..(14)
<223> OTHER INFORMATION: Xaa is Thr, Ile, Leu, Nle, N-methyl Thr, or
      N-methyl Ile.
<220> FEATURE:
<221> NAME/KEY: MOD_RES
<222> LOCATION: (14)..(14)
<223> OTHER INFORMATION: AMIDATION (optional)

<400> SEQUENCE: 5

Xaa Xaa Cys Val Xaa Gln Xaa Xaa Gly Xaa His Xaa Cys Xaa
1               5                   10

<210> SEQ ID NO 6
<211> LENGTH: 14
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 6

Gly Ile Cys Val Trp Gln Asp Trp Gly Ala His Arg Cys Ile
1               5                   10

<210> SEQ ID NO 7
<211> LENGTH: 14
<212> TYPE: PRT
<213> ORGANISM: Artificial Sequence
<220> FEATURE:
<223> OTHER INFORMATION: synthetic sequence
```

```
<220> FEATURE:
<221> NAME/KEY: VARIANT
<222> LOCATION: (1)..(1)
<223> OTHER INFORMATION: Xaa is D-Tyr
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 7

Xaa Ile Cys Val Trp Gln Asp Trp Gly Ala His Arg Cys Ile
 1               5                  10

<210> SEQ ID NO 8
<211> LENGTH: 15
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is D-Tyr
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (15)..(15)
<223> OTHER INFORMATION: AMIDATION

<400> SEQUENCE: 8

Xaa Ile Cys Val Trp Gln Asp Trp Gly Ala His Arg Cys Ile Lys
 1               5                  10                  15

<210> SEQ ID NO 9
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is D-Tyr
<220> FEATURE:
<221> NAME/KEY: DISULFID
<222> LOCATION: (3)..(13)
```

```
-continued

<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 9

Xaa Ile Cys Val Trp Gln Asp Trp Gly Ala His Arg Cys Ile Lys Lys
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is D-Tyr
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (17)..(17)
<223> OTHER INFORMATION: AMIDATION

<400> SEQUENCE: 10

Xaa Ile Cys Val Trp Gln Asp Trp Gly Ala His Arg Cys Ile Lys Lys
1               5                   10                  15
Lys
```